US011701363B2

(12) United States Patent
Perrine et al.

(10) Patent No.: US 11,701,363 B2
(45) Date of Patent: Jul. 18, 2023

(54) METHODS FOR TREATING VIRAL DISORDERS

(71) Applicant: TRUSTEES OF BOSTON UNIVERSITY, Boston, MA (US)

(72) Inventors: Susan Park Perrine, Weston, MA (US); Douglas Faller, Weston, MA (US)

(73) Assignee: Trustees of Boston University, Boston, MA (US)

(*) Notice: Subject to any disclaimer, the term of this patent is extended or adjusted under 35 U.S.C. 154(b) by 0 days.

(21) Appl. No.: 16/518,226

(22) Filed: Jul. 22, 2019

(65) Prior Publication Data

US 2020/0016161 A1 Jan. 16, 2020

Related U.S. Application Data

(63) Continuation of application No. 14/819,024, filed on Aug. 5, 2015, now abandoned, which is a
(Continued)

(51) Int. Cl.
*A61K 31/522* (2006.01)
*A61K 31/00* (2006.01)
(Continued)

(52) U.S. Cl.
CPC ............ *A61K 31/522* (2013.01); *A61K 31/00* (2013.01); *A61K 31/166* (2013.01);
(Continued)

(58) Field of Classification Search
CPC .. A61K 31/522; A61K 31/198; A61K 31/166; A61K 31/185; A61K 31/223;
(Continued)

(56) References Cited

U.S. PATENT DOCUMENTS 3,471,513 A 10/1969 Chinn
3,904,612 A 9/1975 Nagasawa et al.
(Continued)

FOREIGN PATENT DOCUMENTS

CA 1209037 A 8/1986
CA 2303268 A1 4/1995
(Continued)

OTHER PUBLICATIONS

Bowers, Total Synthesis and Biological Mode of Action of Largazole: A Potent Class I Histone Deacetylase Inhibitor, J. Am. Chem. Soc., 2008, 130, pp. 11219-11222 (Year: 2008).*
(Continued)

*Primary Examiner* — Savitha M Rao
*Assistant Examiner* — Andrew P Lee
(74) *Attorney, Agent, or Firm* — Nixon Peabody LLP; Ronald I. Eisenstein; Susanna C. Benn

(57) ABSTRACT

Disclosed are methods of treating viral disorders via the administration of an inducing agent and an anti-viral agent. In one embodiment, the inducing agent and the anti-viral agent are administered for about five days, and the anti-viral agent is subsequently administered without the inducing agent for an additional period of about sixteen days for a total cycle of about 21 days.

15 Claims, 19 Drawing Sheets

Specification includes a Sequence Listing.

Related U.S. Application Data continuation of application No. 14/624,852, filed on Feb. 18, 2015, now abandoned, which is a continuation of application No. 13/915,092, filed on Jun. 11, 2013, now Pat. No. 8,993,581, which is a continuation of application No. 12/890,042, filed on Sep. 24, 2010, now abandoned.

(60) Provisional application No. 61/295,663, filed on Jan. 15, 2010, provisional application No. 61/245,529, filed on Sep. 24, 2009.

(51) Int. Cl.

| | | |
|---|---|---|
| *A61K 31/166* | (2006.01) | |
| *A61K 31/185* | (2006.01) | |
| *A61K 31/198* | (2006.01) | |
| *A61K 31/223* | (2006.01) | |
| *A61K 31/12* | (2006.01) | |
| *A61K 38/15* | (2006.01) | |
| *A61K 45/06* | (2006.01) | |
| *A61K 38/12* | (2006.01) | |

(52) U.S. Cl.
CPC .......... *A61K 31/185* (2013.01); *A61K 31/198* (2013.01); *A61K 31/223* (2013.01); *A61K 38/12* (2013.01); *A61K 38/15* (2013.01); *A61K 45/06* (2013.01)

(58) Field of Classification Search
CPC ........ A61K 38/12; A61K 38/15; A61K 31/00; A61K 45/06; A61P 35/00; A61P 31/12
See application file for complete search history.

(56) References Cited

U.S. PATENT DOCUMENTS

| | | |
|---|---|---|
| 4,008,323 A | 2/1977 | Cousse |
| 4,011,336 A | 3/1977 | Amann |
| 4,026,896 A | 5/1977 | Harita |
| 4,031,243 A | 6/1977 | Aparicio |
| 4,058,558 A | 11/1977 | Cousse |
| 4,131,617 A | 12/1978 | Esanu |
| 4,176,193 A | 11/1979 | Esanu |
| 4,234,599 A | 11/1980 | Van Scott |
| 4,613,616 A | 9/1986 | Winston |
| 4,671,901 A | 6/1987 | Green |
| 4,699,926 A | 10/1987 | Abraham |
| 4,704,402 A | 11/1987 | Abraham |
| 4,723,958 A | 2/1988 | Pope |
| 4,731,381 A | 3/1988 | Abraham |
| 4,732,914 A | 3/1988 | Morton |
| 4,735,967 A | 4/1988 | Neesby |
| 4,747,825 A | 5/1988 | Linkie |
| 4,751,244 A | 6/1988 | Abraham |
| 4,766,116 A | 8/1988 | Tatsuoka |
| 4,820,711 A | 4/1989 | Pearlman |
| 4,822,821 A | 4/1989 | Perrine |
| 4,849,426 A | 7/1989 | Pearlman |
| 4,851,229 A | 7/1989 | Macgruder |
| 4,853,388 A | 8/1989 | Pearlman |
| 4,880,624 A | 11/1989 | Metcalf |
| 4,894,364 A | 1/1990 | Greer |
| 4,925,873 A | 5/1990 | Friedhoff |
| 4,948,592 A | 8/1990 | Ayer |
| 4,952,560 A | 8/1990 | Kigasawa |
| 4,958,592 A | 9/1990 | Anthony |
| 4,965,251 A | 10/1990 | Stamatoyannopoulos |
| 4,997,815 A | 3/1991 | Perrine |
| 5,023,251 A | 6/1991 | Sattler |
| 5,025,029 A | 6/1991 | Perrine |
| 5,032,307 A | 7/1991 | Yu |
| 5,039,703 A | 8/1991 | Breuer |
| 5,081,124 A | 1/1992 | Hughes |
| 5,100,647 A | 3/1992 | Agus |
| 5,137,734 A | 8/1992 | Spieglman |
| 5,185,436 A | 2/1993 | Villa |
| 5,199,942 A | 4/1993 | Gillis |
| 5,208,333 A | 5/1993 | Paul |
| 5,216,004 A | 6/1993 | Perrine |
| 5,258,367 A | 11/1993 | Bazer |
| 5,270,458 A | 12/1993 | Lemischka |
| 5,366,996 A | 11/1994 | Elford |
| 5,378,716 A | 1/1995 | Hamanaka |
| 5,403,590 A | 4/1995 | Forse |
| 5,403,867 A | 4/1995 | Okumura |
| 5,468,731 A | 11/1995 | Matsuo |
| 5,635,532 A | 6/1997 | Samid |
| 5,654,333 A | 8/1997 | Samid |
| 5,661,179 A | 8/1997 | Samid |
| 5,674,898 A | 10/1997 | Cheng |
| 5,674,912 A | 10/1997 | Martin |
| 5,679,707 A | 10/1997 | Okumura |
| 5,710,175 A | 1/1998 | Samid |
| 5,750,571 A | 5/1998 | Cheng |
| 5,780,451 A | 7/1998 | DeMichele |
| 5,843,994 A | 12/1998 | Samid |
| 5,846,528 A | 12/1998 | Podsakoff |
| 5,852,056 A | 12/1998 | Samid |
| 5,858,365 A | 1/1999 | Faller |
| 5,883,123 A | 3/1999 | Tung |
| 5,912,269 A | 6/1999 | Tung |
| 5,932,545 A | 8/1999 | Henkin |
| 5,939,456 A | 8/1999 | Perrine |
| 5,945,407 A | 8/1999 | Bemis |
| 5,952,314 A | 9/1999 | DeMichele |
| 6,011,000 A | 1/2000 | Perrine |
| 6,030,961 A | 2/2000 | Nudelman |
| 6,046,689 A | 3/2000 | Nudelman |
| 6,197,743 B1 | 3/2001 | Faller |
| 6,231,880 B1 | 5/2001 | Perrine |
| 6,403,647 B1 | 6/2002 | Perrine |
| 6,451,334 B2 | 9/2002 | Perrine |
| 6,677,302 B2 | 1/2004 | Faller |
| 7,192,715 B2 | 3/2007 | Harley |
| 7,265,153 B2 | 9/2007 | Faller |
| 8,242,172 B2 | 8/2012 | Perrine |
| 2001/0009922 A1 | 7/2001 | Faller |
| 2001/0027215 A1 | 10/2001 | Perrine |
| 2003/0018069 A1 | 1/2003 | Faller |
| 2003/0077297 A1 | 4/2003 | Chen |
| 2005/0272644 A1 | 12/2005 | Chung |
| 2006/0074046 A1 | 4/2006 | Redkar |
| 2007/0232528 A1 | 10/2007 | Hanshermann |
| 2008/0027136 A1 | 1/2008 | Faller |
| 2008/0057086 A1 | 3/2008 | Etter |
| 2008/0175849 A1 | 7/2008 | Smith |
| 2008/0254026 A1 | 10/2008 | Long |
| 2009/0082444 A1 | 3/2009 | Perrine |
| 2009/0130134 A1 | 5/2009 | Pancre |
| 2011/0033946 A1 | 2/2011 | Berenson |

FOREIGN PATENT DOCUMENTS

| | | |
|---|---|---|
| CA | 2173976 A1 | 2/2008 |
| EP | 0069659 A1 | 1/1983 |
| EP | 0224599 A1 | 6/1987 |
| EP | 0320726 A2 | 6/1989 |
| EP | 0324574 A2 | 7/1989 |
| EP | 0350287 A2 | 1/1990 |
| EP | 0371789 B1 | 6/1990 |
| EP | 0546261 A1 | 6/1990 |
| EP | 0320726 A3 | 8/1990 |
| EP | 0324574 A3 | 12/1990 |
| EP | 0546261 A3 | 8/1993 |
| EP | 0617966 A1 | 10/1994 |
| GB | 2126082 A | 3/1984 |
| JP | 61-89335 | 7/1975 |
| JP | 61-180740 A | 8/1986 |
| WO | 199001071 A1 | 10/1990 |
| WO | 199101719 A1 | 2/1991 |
| WO | 199203155 A1 | 3/1992 |
| WO | 199204913 A1 | 4/1992 |

(56) References Cited

FOREIGN PATENT DOCUMENTS

| WO | 199307866 A2 | 4/1993 |
|---|---|---|
| WO | 199318761 A1 | 9/1993 |
| WO | 199404671 A1 | 3/1994 |
| WO | 199510271 A2 | 4/1995 |
| WO | 199511699 A1 | 5/1995 |
| WO | 199510271 A3 | 6/1995 |
| WO | 199602244 A1 | 2/1996 |
| WO | 199627369 | 9/1996 |
| WO | 199627369 | 11/1996 |
| WO | 199704761 A1 | 2/1997 |
| WO | 199804290 A2 | 2/1998 |
| WO | 199804290 A3 | 8/1998 |
| WO | 199840078 A1 | 9/1998 |
| WO | 199856370 A2 | 12/1998 |
| WO | 199856370 A3 | 4/1999 |
| WO | 2007133653 A2 | 11/2007 |
| WO | 2009067543 A2 | 5/2009 |

OTHER PUBLICATIONS

Perrine et al., "Benign sickle-cell anaemia", Lancet 2(7788) 1163-1167 (1972).
Perrine et al., "Butryic acid analogues augment gamma globin gene expression in neonatal erythroid progenitors", Biochem Biophys Res Commun 148(2) 694-700 (1987).
Perrine et al., "Butyrate derivatives. New agents for stimulating fetal globin production in the beta-globin disorders", Am J Pediatr Hematol Oncol 16(1) 67-71 (1994).
Perrine et al., "Butyrate infusions in the ovine fetus delay the biologic clock for globin gene switching", Proc Natl Acad Sci USA 85(22) 8540-8542 (1988).
Perrine et al., "Butyrate-induced reactivation of the fetal globin genes: A molecular treatment for theβ-hemoglobinophaties", Cellular and Molecular Life Sciences 49(2) 133-137 (1993).
Perrine et al., "HQK-1001 Has Additive HbF-Inducing Activity in Combination with Hydroxyurea and Decitabine", Blood 114(22) 977 (2009).
Perrine et al., "Induction of fetal globin in beta-thalassemia: Cellular obstacles and molecular progress", Ann N Y Acad Sci 1054; 257-265 (2005).
Perrine et al., "Isobutyramide, an orally bioavailable butyrate analogue, stimulates fetal globin gene expression in vitro and in vivo", Br J Haematol 88(3) 555-561 (1994).
Perrine et al., "Natural history of sickle cell anemia in Saudi Arabs. A study of 270 subjects", Ann Intren Med 88(1) 1-6 (1978).
Perrine et al., "Phase 1 clinical testing of HQK-1001, a novel oral fetal globin gene inducer", Abstract from ASH Annual Meeting and Exposition (2008).
Perrine et al., "Phase 1 clinical testing of HQK-1001, a novel oral fetal globin gene inducer", Slides presented at AHS Annual Meeting and Exposition (2008).
Perrine et al., "Rh-Activin increases erythroid progenitor growth and HbF in childhood red cell failure syndromes and hemoglobinopathies", Blood 74(7) Suppl 1, Abstract p. 114 (1989).
Perrine et al., "Sodium butyrate enhances fetal globin gene expression in erythroid progenitors of patients with Hb SS and beta thalassemia", Blood 74(1) 454-459 (1989).
Perrine, "Fetal globin induction—can it cure beta thalassemia?", Hematology Am Cod Hematol Educ Program 38-44 (2005).
Planchon et al., "Differential effects of butyrate derivatives on human breast cancer cells grown as organotypic nodules in vitro and as xenografts in vivo", In Vivo 6(6) 605-610 (1992).
Planchon et al., "Morphology and intermediate filament composition of human mammary epithelial cells treated with stable butyrate derivative", Anticancer Res 12(6B 2315-2320 (1992).
Planchon et al., "New stable butyrate derivatives alter proliferation and differentiation in human mammary cells", Int J Cancer 48(3) 443-449 (1991).
Platt et al., "Mortality in sickle cell disease. Life expectancy and risk factors for early death", N Engl J Med 330(23) 1639-1644 (1994).
Platt et al., "Pain in sickle cell disease. Rates and risk factors.", N Engl J Med 325(1) 11-16 (1991).
Pootrakul et al., "A correlation of erythrokinetics, ineffective erythropoiesis, and erythroid precursor apoptosis in thai patients with thalassemia", Blood 96(7) 2606-2612 (2000).
Pouillart et al., "Enhancement by stable butyrate derivatives of antitumor and antiviral actions of interferon", Int J Cancer 51(4) 596-601 (1992).
Powars et al., "Is there a threshold level of fetal hemoglobin that ameliorates morbidity in sickle cell anemia?", Blood 63(4) 921-926 (1984).
Prasad et al., "Butyric acid: a small fatty acid with diverse biological functions", Life Sci 27(15) 1351-1358 (1980).
Prochownik et al., "Butyric acid: a small fatty acid with diverse biological functions", Nature 322(6082) 848-850 (1986).
Rachmilewitz et al., "The role of recombinant human erythropoietin in the treatment of thalassemia", Ann N Y Acad Sci 850; 129-138 (1998).
Reiss et al., "Induction of tumor cell differentiation as a therapeutic approach: preclinical models for hematopoietic and solid neoplasms", Cancer Treat Rep 70(1) 201-218 (1986).
Rephaeli et al., "Anti-lekemic effect of butyrate in-vitro and in-vivo and the development of a potent butyrate prodrug", Blood 76; 115a (1990).
Reynolds, "The Extra Pharmacopoeia", 29th Edition 1359 (1989).
Richie et al., "Reactivation of DNA Viruses in Association With Histone Deacetylase Inhibitor Therapy: A Case Series Report", No. 2009 Haematological, 94 pp. 1618-1622.
Rickinson et al., "Epstein-Barr Virus" In Fields Virology 2(3) 2397-2446 (1996).
Rius et al., "The induction of vimentin gene expression by sodium butyrate in human promonocytic leukemia U937 cells", Exp Cell Res 188(1) 129-134 (1990).
Rodgers et al., "Augmentation by erythropoietin of the fetal-hemoglobin response to hydroxyurea in sickle cell disease", N Engl J Med 328(2) 73-80 (1993).
Roediger et al., "Selective reduction of fatty acid oxidation in colonocytes: correlation with ulcerative colitis", Lipids 25(10) 646-652 (1990).
Rowe et al., "Colonic short-chain fatty acids: fuel from the lumen?", Gastroenterology 103(1) 336-338 (1992).
Rowinsky et al., "Prolonged infusion of hexamethylene bisacetamide: a phase I and pharmacological study", Cancer Res 47(21) 5788-5795 (1987).
Rubenstein et al., "A pilot clinical trial of oral sodium 4-phenylbutyrate (Buphenyl) in deltaF508-homozygous cystic fibrosis patients: partial restoration of nasal epithelial CFTR function", Am J Respir Crit Care Med 157(2) 484-490 (1998).
Rubenstein et al., "In vitro pharmacologic restoration of CFTR-mediated chloride transport with sodium 4-phenylbutyrate in cystic fibrosis epithelial cells containing delta F508-CFTR", J Clin Invest 100(10) 2457-2465 (1997).
Rund et al., "Beta-thalassemia", N Engl J Med 353(11) 1135-1146 (2005).
Sachs et al., "Cell differentiation and bypassing of genetic defects in the suppression of malignancy", Cencer Res 47(8) 1981-1986 (1987).
Sacktor et al., "The epidemiology of human immunodeficiency virus-associated neurological disease in the era of highly active antiretroviral therapy", J Neurovirol 2;115-121 (2002).
Sadaie et al., "Induction of developmentally programmed cell death and activation of HIV by sodium butyrate", Virology 202(1) 513-518 (1994).
Safaya et al., "Augmentation of gamma-globin gene promoter activity by carboxylic acids and components of the human beta-globin locus control region", Blood 84(11) 3929-3935 (1994).
Schafer et al., "Failure is an option: learning from unsuccessful proof-of-concept trials",. Drug Discov Today 13(21-22) 913-916 (2008).
Scheppach et al., "Effect of butyrate enemas on the colonic mucosa in distal ulcerative colitis", Gastroenterology 103(1) 51-56 (1992).
Scherr et al., "School contact among persons with Hodgkin's disease", Am J Epidemiol 120(1) 29-38 (1984).

(56) References Cited

OTHER PUBLICATIONS

Seifter et al., "An outlier theory of cancer curability. Tumor cell differentiation as a therapeutic goal", An J Med 83(4) 757-760 (1987).
Sher et al., "Rapid healing of chronic leg ulcers during arginine butyrate therapy in patients with sickle cell disease and thalassemia", Blood 84(7) 2378-2380 (1994).
Shibata et al., "Epstein-Barr virus-associated non-Hodgkin's lymphoma in patients infected with the human immunodeficiency virus", Blood 81(8) 2102-2109 (1993).
Singer et al., "Fetal haemoglobin augmentation in E/beta(0) thalassaemia: clinical and haematological outcome", Br J Haematol 131(3) 378-388 (2005).
Slamon et al., "Expression of cellular oncogenes in human malignancies", Science 224(4646) 256-262 (1984).
Speck et al., "Infection of breast epithelial cells with Epstein-Barr virus via cell-to-cell contact", J Natl Cancer Inst 92 (22) 1849-1851 (2000).
Sripichai et al., "A scoring system for the classification of beta-thalassemia/Hb E disease severity" Am J Hematol 83(6) 482-484 (2008).
Stamatoyannopoulos et al., "Fetal hemoglobin induction by acetate, a product of butyrate catabolism", Blood 84(9) 3198-3204 (1994).
Stamatoyannopoulos et al., "The Regulation of Hemoglobin Switching", Johns Hopkins Univ Pr. (1991).
Steinberg et al., "Effect of hydroxyurea on mortality and morbidity in adult sickle cell anemia: risks and benefits up to 9 years of treatment", JAMA 289(13) 1645-1651 (2003).
Steinberg et al., "Fetal hemoglobin in sickle cell anemia: determinants of response to hydroxyurea. Multicenter Study of Hydroxyurea", Blood 89(3) 1078-1088 (1997).
Steinberg et al., "Predicting clinical severity in sickle cell anaemia", Br J Haematol 129(4) 465-481 (2005).
Steingberg et al., "Pharmacologic modulation of fetal hemoglobin", Medicine (Baltimore) 80(5) 328-344 (2001).
Su et al., "Aggressive peripheral T-cell lymphomas containing Epstein-Barr viral DNA: a clinicopathologic and molecular analysis", Blood 77(4) 799-808 (1991).
Sutherland et al., "Induction of the expression of HLA class I antigens on K562 by interferons and sodium butyrate", Hum Immunol 12(2) 65-73 (1985).
Swinnen et al., "Overview of posttransplant B-cell lymphoproliferative disorders", Semin Oncol 26(Suppl 14) 21-25 (1999).
Takahashi et al., "Differentiation of cultured Friend leukemia cells induced by short-chain fatty acids", Gan 66(5)577-580 (1975).
Tang et al., "Memory of butyrate induction by the Moloney murine sarcoma virus enhancer-promoter element", Biochem Biophys Res Commun 189(1) 141-147 (1992).
Testa et al., "Apoptotic mechanisms in the control of erythropoiesis", Leukemia 18(7) 1176-1199 (2004).
The Merck Index of Chemicals and Drugs, 7th Edition, 1960:434.
Torrealba-de Ron et al., "Perturbations in the erythroid marrow progenitor cell pools may play a role in the augmentation of HbF by 5-azacytidine", Blood 63(1) 201-210 (1984).
Toussirot et al., "Epstein-Barr virus in autoimmune diseases", Best Pract Res Clin Rheumatol 22(5) 883-896 (2008).
Tsao et al., "Differential effects of sodium butyrate, dimethyl sulfoxide, and retinoic acid on membrane-associated antigen, enzymes, and glycoproteins of human rectal adenocarcinoma cells", Cancer Res 42(3) 1052-1058 (1982).
Tuan et al., "Different 3' end points of deletions causing delta beta-thalassemia and hereditary persistence of fetal hemoglobin: implications for the control of gamma-globin gene expression in man", Proc Natl Acad Scie USA 80(22) 6937-6941 (1983).
Ulrich et al., "Function of normal and mutated gamma-globin gene promoters in electroporated K562 erythroleukemia cells", Blood 75(4) 990-999 (1990).
Vichinsky et al., "Changes in the epidemiology of thalassemia in North America: a new minority disease", Pediatrics 116(6) e818-825 (2005).

Vichinsky, "Hemoglobin E Syndromes", Hematology Am Soc Hematol Educ Program 79-83 (2007).
Vichinsky, "Changing patterns of thalassemia worldwide", Ann N Y Acad Sci 1054; 18-24 (2005).
Vile et al., "Systemic gene therapy of murine melanoma using tissue specific expression of the HSVtk gene involves an immune component", Cancer Res 54(23) 6228-6234 (1994).
Volkov et al., "Cinnamic acid in analytical chemistry. X Determinant of scandium as cinnamate and its separation from the rare earth elements and yttrium", Zh Anal Khim 22(3) 340-345 (1967).
Walsh et al., "Combination of drug and gene delivery by gelatin nanospheres for the treatment of cystic fibrosis", Proceedings of the Controlled Release Society 24; 75-76 (1997).
Wasserman et al., "Differential effects of sodium butyrate and dimethylsulfoxide on gamma-glutamyl transpeptidase and alkaline phosphatase activities in MCF-7 breast cancer cells", Pathobiology 55(4) 189-193 (1987).
Watkins et al., "Choleretic effect of structural analogs of valproic acid in the rat", Res Commun Chem Pathol Pharmacol 39(3) 355-366 (1983).
Watson et al., "Butyrate acid in the treatment of cancer", 746-748 (1933).
Weatherakk et al., "A model for the persistence or reactivation of fetal haemoglobin production", Lancet 2(7987) 660-663 (1976).
Weiss et al., "Detection of Epstein-Barr viral genomes in Reed-Sternberg cells of Hodgkin's disease", N Engl J Med 320(8) 502-506 (1989).
Weiss et al., "Epstein-Barr viral DNA in tissues of Hodgkin's disease", Am J Pathol 129(1) 86-91 (1987).
Weiss et al., "Epstein-Barr virus and Hodgkin's disease. A correlative in situ hybridization and polymerase chain reaction study", Am J Pathol 139(6) 1259-1265 (1991).
Wightman et al., "HDAC inhibitors in HIV", Immunol Cell Biol 90(1) 47-54 (2012).
Williams et al., "Identification of a ligand for the c-kit proto-", 63(1) 167-174 (1990).
Winichagoon et al., "Beta-Thalassemia in Thailand", Annals of the New York Academy of Sciences 612; 31-42 (1990).
Wittstruck et al., "A nuclear magnetic resonance study of transmission of electronic effects. Ethylbenzenes, dihydrocinnamic acids, and cis-and trans-cinnamic acids", Journal of the American Chemical Society 89(15) 3803-3809 (1967). Abstract Only.
Wood et al., "Hb F synthesis in sickle cell anaemia: a comparison of Saudi Arab cases with those of African origin", Br J Haematol 45(3) 431-445 (1980).
Wu et al., "Detection of EBV gene expression in Reed-Sternberg cells of Hodgkin's disease", Inte J Cancer 46(5) 801-804 (1990).
Yeivin et al., "Sodium butyrate selectively induces transcription of promoters adjacent to the MoMSV viral enhancer", Gene 116(2) 159-164 (1992).
Young et al., "Phase I trial and clinical pharmacological evaluation of hexamethylene bisacetamide administration by ten-day continuous intravenous infusion at twenty-eight-day intervals", Cancer Res 48(24 Pt 1) 7304-7309 (1988).
Zeitlin et al., "Evidence of CFTR function in cystic fibrosis after systemic administration of 4-phenylbutyrate", Mol Ther 6(1) 119-126 (2002).
Zhang et al., "Effect of (E)-5-(2-bromovinyl)-2'-deoxyuridine on several parameters of Epstein-Barr virus infection", J Gene Virol 65(Pt 1) 37-46 (1984).
Zituik et al., "The silencing of gamma-globin gene exin a beta-globin locus yac can be arrested by an alpha-aminobutyric acid", Abstract of ASH Annual Meeting, Seattl, Washington Dec 105, 1995.
Zsebo et al., "Identification, purification, and biological characterization of hematopoietic stem cell factor from buffalo rat liver—conditioned medium", Cell 63(1) 195-201 (1990).
Zsebo et al., "Stem cell factor is encoded at the SI locus of the mouse and is the ligand for the c-kit tyrosine kinase receptor", Cell 63(1) 213-214 (1990).
Zur Hausen et al., "EBV DNA in biopsies of Burkitt tumours and anaplastic carcinomas of the nasopharynx", 228(5276) 1056-1058 (1970).

(56) References Cited

OTHER PUBLICATIONS

Chany et al., "Effect of coordinated therapeutic assays using C. parvum, interferon and arginine butyrate on spontaneous disease and survival of AKR mice", Int J Cancer 32(3) 379-383 (1983).
Faller et al., "Arginine Butyrate-induced susceptibility to ganciclovir in Epstein Barr virus (EBV)-associated lymphomas", Proceedings of the American Association for Cancer Research 37; 411-412 (1996).
Fibach et al., "Enhanced fetal hemoglobin production by phenylacetate and 4-phenylbutyrate in erythroid precursors derived from normal donors and patients with sickle cell anemia and beta-thalassemia", Blood 82(7) 2203-2209 (1993).
Flyer et al., "Retrovirus-induced changes in major histocompatibility complex antigen expression influence susceptibility to lysis by cytotoxic T lymphocytes", J Immunol 135(4) 2287-2292 (1985).
Forrester et al., "Molecular analysis of the human beta-globin locus activation region", Proc Natl Acad Sci USA 86(14) 5439-5443 (1989).
Foss et al., "Biomodulatory Effects of Butyric-Acid Derivatives on Leukemia and Lymphoma-Cells", Blood 82(10) Abstract Only (1993).
Franco et al., "The effect of fetal hemoglobin on the survival characteristics of sickle cells", Blood 108(3) 1073-1076 (2006).
Frankie et al., "Experiences with alpha-aminoisobutyric acid in the treatment of wounds", Zentralbl Chir 79(18) 769-776 (1954).
Fraser et al., "Each hypersensitive site of the human beta-globin locus control region confers a different developmental pattern of expression on the globin genes", Genes Dev 7(1) 106-113 (1993).
Fritsch et al., "Characterisation of deletions which affect the expression of fetal globin genes in man", Nature 279(5714) 598-603 (1979).
Fucharoen et al., "Alpha- and Beta-Thalassemia in Thailand", Ann N Y Acad Sci 30(850) 412-414 (1998).
Fucharoen et al., "Clinical and hematologic aspects of hemoglobin E beta-thalassemia", Curr Opin Hematol 7(2) 106-112 (2000).
Fucharoen et al., "Haemoglobinopathies in southeast Asia", Indian J Med Res 134; 498-506 (2011).
Fucharoen et al., "Thalassemia in SouthEast Asia: problems and strategy for prevention and control", Southeast Asian J Trop Med Public Health 23(4) 647-655 (1992).
Gabbianelli et al., "Granulocyte-macrophage colony-stimulating factor reactivates fetal hemoglobin synthesis in erythroblast clones from normal adults", Blood 74(8) 2657-2667 (1989).
Garre et al., "Regulation of acetylcholinesterase expression in the K-562 cell line", Cancer Res 44(9) 3749-3751 (1984).
Garsetti et al., "Butyric acid-induced differentiation of HL-60 cells increases the expression of a single lysophospholipase", Biochem 288(Pt 3) 831-837 (1992).
Gaudet et al., "Differential regulation of arylamine and arylalkylamine N-acetyltransferases in human retinoblastoma (Y-79) cells", Neurochem Int 22(3) 271-275 (1993).
Gerharz et al., "Modulation of invasive potential in different clonal subpopulations of a rat rhabdomyosarcoma cell line (BA-HAN-1) by differentiation induction", Clin Exp Metastasis 11(1) 55-67 (1993).
Ghanayem et al., "Structure-activity relationships for the in vitro hematotoxicity of N-alkoxyacetic acids, the toxic metabolites of glycol ethers", Chem Biol Interact 70(3-4) 339-352 (1989).
Gilbert et al., "A phase I dose escalation and bioavailability study of oral sodium phenylbutyrate in patients with refractory solid tumor malignancies", Clin Cancer Res 7(8) 2292-2300 (2001).
Ginder et al., "Activation of a chicken embryonic globin gene in adult erythroid cells by 5-azacytidine and sodium butyrate". Proc Natl Acad Sci USA 81(13) 3954-3958 (1984).
Gladwin et al., "Pulmonary hypertension as a risk factor for death in patients with sickle cell disease", N Engl J Med 350(9) 886-895 (2004).
Gladwin et al., "Unraveling the hemolytic subphenotype of sickle cell disease", Blood 106(9) 2925-2926 (2005).

Glaser et al., "Epstein-Barr virus-associated Hodgkin's disease: epidemiologic characteristics in international data", Int J Cancer 70(4) 375-382 (1997).
Golub et al., "Induction of dormant HIV-1 by sodium butyrate: involvement of the TATA box in the activation of the HIV-1 promoter", AIDS 5(6) 663-668 (1991).
Gredmark et al., "Active cytomegalovirus replication in patients with coronary disease", Scand Cardiovasc J 41(4) 230-234 (2007).
Greenspan et al., "Replication of Epstein-Barr virus within the epithelial cells of oral "hairy" leukoplakia, an AIDS-associated lesion", N Engl J Med 313(25) 1564-1571 (1985).
Griffin et al., "Relation of Burkitt's tumor-associated herpes-type virus to infectious mononucleosis", Rev Med Virol 8 (2) 61-66 (1998).
Gross et al., "B cell lymphoproliferative disorders following hematopoietic stem cell transplantation: risk factors, treatment and outcome", Bone Marrow Transplantation 23(3) 251-258 (1999).
Grossi et al., "Effects of monosaccharide esters of butyric acid on the synthesis of hemoglobin T chain and erythroleukemis cell line", Abstract of ASH Annual Meeting, Seattle, WA Dec. 1995.
Grufferman et al., "Hodgkin's disease in siblings", N Engl J Med 296(5) 248-250 (1977).
Guilbaud et al., "Effects of differentiation-inducing agents on maturation of human MCF-7 breast cancer cells", J Cell Physiol 145(1) 162-172 (1990).
Gum et al., "Effects of sodium butyrate on human colonic adenocarcinoma cells. Induction of placental-like alkaline phosphatase", J Biol Chem 262(3) 1092-1097 (1987).
Hahn et al., "Therapeutic outcome of Epstein-Barr virus positive T/NK cell lymphoma in the upper aerodigestive tract", Yonsei Med J 43(2) 175-182 (2002).
Hanto et al., "Epstein-Barr virus (EBV) induced polyclonal and monoclonal B-cell lymphoproliferative diseases occurring after renal transplantation. Clinical, pathologic, and virologic findings and implications for therapy", Annals of Surgery 198(3) 356-369 (1983).
Harabuchi et al., "Epstein-Barr virus in nasal T-cell lymphomas in patients with lethal midline granuloma", Lancet 335(8682) 128-130 (1990).
Harig et al., "Treatment of diversion colitis with short-chain-fatty acid irrigation", N Engl J Med 320(1) 23-28 (1989).
Henle et al., "Epstein-barr virus and human malignancies", Cancer 34(S8) 1368-1374 (1974).
Herbst et al., "Epstein-Barr virus latent membrane protein expression in Hodgkin and Reed-Sternberg cells", Proc Natl Acad Sci USA 88(11) 4766-4770 (1991).
Hierro. "Efficacy and Saftey of Valganciclovir in Liver-Transplanted Children Infected with Epstein-Barr Virus", Liver Transplantation, 2008, 13, pp. 1185-1193.
Ho et al., "Presence of Epstein-Barr virus DNA in nasal lymphomas of B and 'T' cell type", Hematol Oncol 8(5) 271-281 (1990).
Hock et al., "Retrovirus-mediated transfer and expression of drug resistance genes in human haematopoietic progenitor cells", Nature 275-277 (1986).
Hoessly et al., "Factors responsible for variable reported lineages of HL-60 cells induced to mature with butyric acid", Cancer Res 49(13) 3594-3597 (1989).
Hoey et al., "Molecular cloning and functional analysis of Drosophila TAF110 reveal properties expected of coactivators", Cell 72(2) 247-260 (1993).
Horig et al., "From bench to clinic and back: Perspective on the 1st IQPC Translational Research conference", J Transl Med 2(1) 44 (2004).
Hsu et al., "Epstein-barr virus-associated malignancies: epidemiologic patterns and etiologic implications", Crit Rev Oncol Hematol 34(1) 27-53 (2000).
Huang et al., "The hematopoietic growth factor KL is encoded by the SI locus and is the ligand of the c-kit receptor, the gene product of the W locus", Cell 63(1) 225-233 (1990).
Huber et al., "In vivo antitumor activity of 5-fluorocytosine on human colorectal carcinoma cells genetically modified to express cytosine deaminase", Cancer Res 53(19) 4619-4626 (1993).

(56) References Cited

OTHER PUBLICATIONS

Huber et al., "Metabolism of 5-fluorocytosine to 5-fluorouracil in human colorectal tumor cells transduced with the cytosine deaminase gene: significant antitumor effects when only a small percentage of tumor cells express cytosine deaminase", Proc Natl Acad Sci USA 91(17) 8302-8306 (1994).
Hurford et al., "Gene therapy of metastatic cancer by in vivo retroviral gene targeting", Nat Genet 10(4) 430-435 (1995).
Ikuta et al., "Alterations in protein-DNA interactions in the gamma-globin gene promoter in response to butyrate therapy", Blood 92(8) 2924-2933 (1998).
Burns et al., "Butyrate induces selective transcriptional activation of a hypomethylated embryonic globin gene in adult erythroid cells", Blood 72(5) 1536-1542 (1988).
Byrd et al., "Two types of transglutaminase in the PC12 pheochromocytoma cell line. Stimulation by sodium butyrate", J Biol Chem 262(24) 11699-11705 (1987).
Callery et al., "Identification of metabolites of the cell-differentiating agent hexamethylene bisacetamide in humans", Cancer Res 46910) 4900-4903 (1986).
Canceill et al., "Stereochimistry of the reduction of b-keto esters, p-keto amides, and b-keto nitriles by hydrides", Bull Soc Chim 6;2180-2187 (1970).
Caruso et al., "Regression of established macroscopic liver metastases after in situ transduction of a suicide gene", Proc Natl Acad Sci USA 90(15) 7024-7028 (1993).
Castaneda et al., "Enhancement of growth and survival and alterations in Bcl-family proteins in beta-thalassemic erythroid progenitors by novel short-chain fatty acid derivatives", Blood Cells Mol Dis 35(2) 217-226 (2005).
Chang et al., "An analysis of fetal hemoglobin variation in sickle cell disease: the relative contributions of the X-linked factor, beta-globin haplotypes, alpha-globin gene number, gender, and age", Blood 85(4) 1111-1117 (1995).
Chany et al., "Antitumor effect of arginine butyrate in conjunction with Corynebacterium parvum and interferon", Int J Cancer 30(4) 489-493 (1982).
Charache et al., "Hydroxyurea-induced augmentation of fetal hemoglobin production in patients with sickle cell anemia", Blood 69(1) 109-116 (1987).
Charache et al., "Treatment of sickle cell anemia with 5-azacytidine results in increased fetal hemoglobin production and is associated with nonrandom hypomethylation of DNA around the gamma-delta-beta-globin gene complex", Proc Natl Acad Sci USA 80(15) 4842-4846 (1983).
Chen et al., "Tributyrin: a prodrug of butyric acid for potential clinical application in differentiation therapy", Cancer Res 54(13) 3494-3499 (1994).
Cheng et al., "Functional activation of the cystic fibrosis trafficking mutant delta F508-CFTR by overexpression", Am J Physiol 268(4 Pt 1) L615-624 (1995).
Chu et al., "In situ detection of Epstein-Barr virus in breast cancer", Cancer Lett 124(1) 53-57 (1998).
Clegg et al., "Abnormal human haemoglobins. Separation and characterization of the alpha and beta chains by chromatography, and the determination of two new variants, hb Chesapeak and hb J (Bangkok)", J Mol Biol 19(1) 91-108 (1966).
Coates et al., "Persistence of Epstein-Barr virus in Reed-Sternberg cells throughout the course of Hodgkin's disease", J Pathol 164(4) 291-297 (1991).
Cohen et al., "Thalassemia" ASH Education Program Book 1(2004) 14-34 (2004).
Collins et al., "Oral sodium phenylbutyrate therapy in homozygous beta thalassemia: a clinical trial", Blood 85(1) 43-49 (1995).
Colombo et al., "Natural history and pathogenesis of hepatitis C virus related hepatocellular carcinoma", J Hepatol1;25-30 (1999).
Constantoulakis et al., "On the induction of fetal hemoglobin by butyrates: in vivo and in vitro studies with sodium butyrate and comparison of combination treatments with 5-AzaC and AraC", Blood 74(6) 1963-1971 (1989).

Cook et al., "Effect of sodium butyrate on alpha-fetoprotein gene expression in rat hepatoma cells in vitro", Cancer Res 45(7) 3215-3219 (1985).
Copeland et al., "Mast cell growth factor maps near the steel locus on mouse chromosome 10 and is deleted in a number of steel alleles", Cell 63(1) 175-183 (1990).
Cossman et al., "Induction of differentiation in a case of common acute lymphoblastic leukemia", N Engl J Med 307(20) 1251-1254 (1982).
Curtis et al., "Risk of lymphoproliferative disorders after bone marrow transplantation: a multi-institutional study", Blood 94(7) 2208-2216 (1999).
Dakshinamurty et al., "Ternary liquid equilibrium systems ethanol-water-methyl isobutyl carbinol and acetic acid-water-ethyl butyrate", J Chem Eng Data 17(3) 379-383 (1972).
Daniel et al., "Pharmacokinetic study of butyric acid administered in vivo as sodium and arginine butyrate salts", Clin Chim Acta 181(3) 255-263 (1989).
Dantchev et al., "Comportement De Certains Composes Pyrimidiques De Lacide Fumarique Et De Lacide Maleique a Legard De La Protection Des Globules Rouges Du Lapin Intoxique Par La Phenylhydrazine", C. R. Acad Sci Hebd Sceances Acad Sci D 264(11) 1467 (1967).
De Bruin et al., "Detection of Epstein-Barr virus nucleic acid sequences and protein in nodal T-cell lymphomas: relation between latent membrane protein-1 positivity and clinical course", Histopathology 23(6) 509-518 (1993).
De Bruin et al., "Presence of Epstein-Barr virus in extranodal T-cell lymphomas: differences in relation to site", Blood 83(6) 1612-1618 (1994).
De Vente et al., "Effects of adenosine and adenosine-analogs on adenylate cyclase activity in the rat adipocyte plasma membrane: comparison of the properties of the enzyme with Mn2+ and Mg2+ as divalent cations", Mol Cell Biochem 40(2) 65-73 (1981).
Dimaio et al., "Directed enzyme pro-drug gene therapy for pancreatic cancer in vivo", Surgery 116(2) 205-213 (1994).
Donaldson et al., "Cytotoxicity of the anticancer agents cisplatin and taxol during cell proliferation and the cell cycle", Int J Cancer 57(6) 847-855 (1994).
Douillard et al., "Phase I trial of interleukin-2 and high-dose arginine butyrate in metastatic colorectal cancer", Cancer Immunol Immunother 49(1) 56-61 (2000).
Dover et al., "Fetal hemoglobin levels in sickle cell disease and normal individuals are partially controlled by an X-linked gene located at Xp22.2", Blood 80(3) 816-824 (1992).
Dover et al., "Hydroxyurea induction of hemoglobin F production in sickle cell disease: relationship between cytotoxicity and F cell production", Blood 67(3) 735-738 (1986).
Dover et al., "Induction of fetal hemoglobin production in subjects with sickle cell anemia by oral sodium phenylbutyrate", Blood 84(1) 339-343 (1994).
Egorin et al., "Phase I clinical and pharmacokinetic study of hexamethylene bisacetamide (NSC 95580) administered as a five-day continuous infusion", Cancer Res 47(2) 617-623 (1987).
El Rassi et al., "Beta-thalassemia intermedia: an overview", Pediatr Ann 37(5) 322-328 (2008).
El-Beshlawy et al., "Fetal globin induction in beta-thalassemia", Hemoglobin 33(Suppl 1) S197-203 (2009).
Ellis et al., "Synthetic human beta-globin 5'HS2 constructs function as locus control regions only in multicopy transgene concatamers", EMBO 12(1) 127-134 (1993).
El-Nawawy et al., "Organic pesticides. II. (Arylthio) acetic acids, (arylenedithio) diacetic acids, and serveral of their S-alkylisothiuronium salts", Alexandria J. Agr Res 16(2) 173-183 (1970).
Endo et al., "Differential induction of adult and fetal globin gene expression in the human CML cell subline KU-812F/33", J Biochem 115(3) 540-544 (1994).
EP 10184726 Search Report dated Jan. 20, 2011.
Euopean Office Action dated Aug. 11, 2010 for Application No. 6021311.3.
European Search Report dated Jun. 16, 2005 for Application No. 94930734.2.

(56) References Cited

OTHER PUBLICATIONS

European Search Report dated Jun. 9, 2009 for Application No. 6021311.3.
Evans et al., "A population-based case-control study of EBV and other viral antibodies among persons with Hodgkin's disease and their siblings", Int J Cancer 34(5) 149-157 (1984).
Faller et al., "Arginine butyrate-induced susceptibility to ganciclovir in an Epstein-Barr Virus (EBV) associate lymphoma". Am. Soc. of Hematology [Blood] 86(10) 342a (1995).
Faller et al., "Phase I/II trial of arginne butyrate to induce viral TK gene expression in Epstein-Barr Virus (EBV)-associated lymphomas", Proc Am Assn for Cancer Research 41:544 (2000).
Fathallah et al., "Induction of fetal hemoglobin in the treatment of sickle cell disease", ASH Education Program Book 1(2006) 58-62 (2006).
Faucitano et al., "reaction of gases with irradiated organic solids Reaction of gases with irradiated organic solids", Ric Sci 37(12) 1149-1155 (1967).
Abbott et al., "Quantitative structure-anticonvulsant activity relationships of valproic acid, related carboxylic acids and tetrazoles", Neuropharmacology 27(3) 287-294 (1988).
Abe et al., "Sodium butyrate induction of milk-related antigens in human MCF-7 breast carcinoma cells", Cancer Res 44(10) 4574-4577 (1984).
Abraham et al., "Design, synthesis, and testing of potential antisickling agents. 1. Halogenated benzyloxy and phenoxy acids", J Med Chem 25(9) 1015-1017 (1982).
Abraham et al., "Synthesis of the minor fetal hemoglobin Fic in colonies of erythropoietic precursors isolated from human umbilical cord blood", Am J Hematol 12(3) 207-213 (1982).
Al-Khatti et al., "Erythropoietin stimulates F-reticulocyte formation in sickle cell anemia", Trans Assoc Am Physicians 101;54-61 (1988).
Anderson et al., "Molecular cloning of mast cell growth factor, a hematopoietin that is active in both membrane bound and soluble forms", Cell 63(1) 235-243 (1990).
Andrews et al., "A rapid micropreparation technique for extraction of DNA-binding proteins from limiting numbers of mammalian cells", Nucleic Acids Res 19(9) 2499 (1991).
Andrews et al., "Erythroid transcription factor NF-E2 is a haematopoietic-specific basic-leucine zipper protein", Nature 362(6422) 722-728 (1993).
Angastiniotis et al., "Global epidemiology of hemoglobin disorders", Ann N Y Acad Sci 850; 251-269 (1998).
Antoni et al., "NF-kappa B-dependent and -independent pathways of HIV activation in a chronically infected T cell line", Virology 202(2) 684-694 (1994).
Archin et al., "Antiretroviral intensification and valproic acid lack sustained effect on residual HIV-1 viremia or resting CD4+ cell infection", Plos One 5(2) e9390 (2010).
Archin et al., "Expression of latent HIV induced by the potent HDAC inhibitor suberoylanilide hydroxamic acid", AIDS Res Hum Retrociruses 25(2) 207-212 (2009).
Archin et al., "Expression of latent human immunodeficiency type 1 is induced by novel and selective histone deacetylase inhibitors", AIDS 23(14) 1799-1806 (2009).
Archin et al., "Valproic acid without intensified antiviral therapy has limited impact on persistent HIV infection of resting CD4+ T cells", AIDS 22(10) 1131-1135 (2008).
Armstrong et al., "Criteria for the definition of Epstein-Barr virus association in Hodgkin's disease", Leukemia 6(9) 869-874 (1992).
Atweh et al., "Pharmacological induction of fetal hemoglobin in sickle cell disease and beta-thalassemia", Semin Hematol 38(4) 367-373 (2001).
Atweh et al., "Sustained induction of fetal hemoglobin by pulse butyrate therapy in sickle cell disease", Blood 93(6) 1790-1797 (1999).
Augeron et al., "Emergence of permanently differentiated cell clones in a human colonic cancer cell line in culture after treatment with sodium butyrate". Cancer Res 44(9) 3961-3969 (1984).

Barbul et al., "Arginine enhances wound healing and lymphocyte immune responses in humans", Surgery 108(2) 331-336 (1990).
Barker et al., "The actions of cyclic AMP, its butyryl derivatives and Na butyrate on the proliferation of malignant trophoblast cells in vitro", Br J Cancer 35(3) 314-321 (1977).
Barton et al., "The erythroid protein cGATA-1 functions with a stage-specific factor to activate transcription of chromatin-assembled beta-globin genes", Gene & Develompent 7(9) 1796-1809 (1993).
Bartram et al., "Proliferation of human colonic mucosa as an intermediate biomarker of carcinogenesis: effects of butyrate, deoxycholate, calcium, ammonia, and pH", Cancer Res 53(14) 3283-3288 (1993).
Basson et al., "Butyrate-induced enterocyte differentiation and mucosal wound healing", Gastroenterology 104(4) supp A235 (1993).
Belcheva et al., "Up-regulation of delta opioid receptors in neuroblastoma hybrid cells: evidence for differences in the mechanisms of action of sodium butyrate and naltrexone", J Pharmacol Exp Ther 259(1) 302-309 (1991).
Berkovitch et al., "Pharmacokinetics of arginine butyrate in patients with hemoglobinopathy", Environ Tox and Pharm 2(4) 403-405 (1996).
Bernards et al., "Physical mapping of the globin gene deletion in hereditary persistence of foetal haemoglobin (HPFH)", Nucleic Acids Red 8(7) 1521-1534 (1980).
Bingham et al., "Patty's toxicology. vol. 2: toxicological issues related to metals, neurotoxicology and radiation metals and metal compounds", No. Ed. 5 John Wiley and Sons (2001).
Birgens et al., "The Thalassaemia Syndromes", Scand J Clin Lab Invest 67(1) 11-26 (2007).
Blau et al., "Fetal hemoglobin induction with butyric acid: efficacy and toxicity", Blood 81(2) 529-537 (1993).
Bloch et al., "Induced Cell Differentiation in Cancer Therapy", Cancer Treatment Reports 68; 318-328 (1984).
Bohacek et al., "Identification of novel small-molecule inducers of fetal hemoglobin using pharmacophore and PSEUDO' receptor models", Chem Biol Drug Des 67(5) 318-328 (2006).
Bohan et al., "Mutational analysis of sodium butyrate inducible elements in the human immunodeficiency virus type I long terminal repeat", Virology 172(2) 573-583 (1989).
Bohan et al., "Sodium butyrate activates human immunodeficiency virus long terminal repeat—directed expression", Biochem Biophys Res Commun 148(3) 899-905 (1987).
Bokori et al., "Swine experiment with a feed containing Sodium-n-butyrate", Chemical Abstracts 112(3) 1376-1381 (1990).
Bonnet et al., "Detection of Epstein-Barr virus in invasive breast cancers", J Nat Cancer Int 91(16) 1376-1381 (1999).
Boosalis et al., "Short-chain fatty acid derivatives stimulate cell proliferation and induce STAT-5 activation", Blood 97(10) 3259-3267 (2001).
Borgna-Pignatti et al., "Survival and complications in thalassemia", Ann N Y Acad Sci 1054(1) 40-47 (2005).
Borgna-Pignatti, "Modern treatment of thalassaemia intermedia", Br J Haematol 138(3) 291-304 (2007).
Boulikas, "Poly(ADP-ribose) synthesis in blocked and damaged cells and its relation to carcinogenesis", Anticancer Res 12(3) 885-898 (1992).
Bourantas et al., "Administration of high doses of recombinant human erythropoietin to patients with beta-thalassemia intermedia: a preliminary trial", Eur J Haematol 58(1) 22-25 (1997).
Bourgeade et al., "Effect of sodium butyrate on the antiviral and anticellular action of interferon in normal and MSV-transformed cells", Int J Cancer 24(3) 314-318 (1979).
Bourgeade et al., "Enhancement of interferon antitumor action by sodium", Cancer Res 39(11) 4720-4723 (1979).
Breitman et al., "Combinations of retinoic acid with either sodium butyrate, dimethyl sulfoxide, or hexamethylene bisacetamide synergistically induce differentiation of the human myeloid leukemia cell line HL60", Cancer Res 50(19) 6268-6273 (1990).
Breur et al., "Rectal irrigation with short-chain fatty acids for distal ulcerative colitis. Preliminary report", Dig Dis Sci 36(2) 185-187 (1991).

(56) References Cited

OTHER PUBLICATIONS

Briz et al., "Epstein-Barr virus associated B-cell lymphoma after autologous bone marrow transplantation for T-cell acute lymphoblastic leukaemia", Br J Haematol 98(2) 485-487 (1997).
Brooks et al., "Epstein-Barr virus and lymphomas", Cancer surv 33;99-123 (1999).
Brousset et al., "Detection of Epstein-Barr virus messenger RNA in Reed-Sternberg cells of Hodgkin's disease by in situ hybridization with biotinylated probes on specially processed modified acetone methyl benzoate xylene (ModAMeX) sections", Blood 77(8) 1781-1786 (1991).
Bugaut et al., "Biological effects of short-chain fatty acids in nonruminant mammals", Annu Rev Nutr 13; 217-241 (1993).
Bunn et al., "Pathogenesis and treatment of sickle cell disease", N Engl J Med 337(11) 762-769 (1997).
Burkitt et al., "A sarcoma involving the jaws in African children", Br J Surg 46(197) 218-223 (1958).
Maziarz et al., "Distinct effects of interferon-γ and MHC class 1 surface antigen levels on resistance of the K562 tumor cell line to natural killer-mediated lysis", Cellular Immunology 130(2) 329-338 (1990).
Maziarz et al., "The regulation of exogenous and endogenous class I MHC genes in a human tumor cell line, K562", Mol Immunol 27(2) 135-142 (1990).
McCafferty et al., "Inhibition of butyric acid-induced colitis in mice by 16,16-dimethyl prostaglandin E2", Agents Actions Spec No. C79-81 (1992).
McCafferty et al., "Short chain fatty acid-induced colitis in mice", Int J Tissue React 11(4) 165-168 (1989).
McClain et al., "Association of Epstein-Barr virus with leiomyosarcomas in young people with AIDS", N Engl J Med 332(1) 12-18 (1995).
McDonagh et al., "The upstream region of the human gamma-globin gene promoter. Identification and functional analysis of nuclear protein binding sites", I Biol Chem 266(18) 11965-11974 (1991).
Medeiros et al., "Localization of Epstein-Barr viral genomes in angiocentric immunoproliferative lesions", Am J Surg Pathol 16(5) 439-447 (1992).
Meijer et al., "Epstein-Barr virus and human T-cell lymphomas", Semin Cancer Biol 7(4) 191-196 (1996).
Migliaccio et al., "Influence of recombinant hematopoietins and of fetal bovine serum on the globin synthetic pattern of human BFUe", Blood 76(6) 1150-1157 (1990).
Miller et al., "Antibodies to butyrate-inducible antigens of Kaposi's sarcoma-associated herpesvirus in patients with HIV-1 infection", N engl J Med 334(20) 1292-1927 (1996).
Miller et al., "Clinical pharmacology of sodium butyrate in patients with acute leukemia", Eur J Cancer Clin Oncol 23(9) 1283-1287 (1987).
Miller et al., "Influence of steel factor on hemoglobin synthesis in sickle cell disease", Blood 79(7) 1861-1868 (1992).
Miller et al., "Toxicity of methoxyacetic acid in rats", Fundamental and Applied Toxicology 2(4) 158-160 (1982).
Modell et al., "Epidemiology of haemoglobin disorders in Europe: an overview", Scand J Clin Lab Invest 67(1) 39-69 (2007).
Moi et al., "Synergistic enhancement of globin gene expression by activator protein-1-like proteins", Proc Natl Acad Sci USA 87(22) 9000-9004 (1990).
Morita et al., "Effect of sodium butyrate on alkaline phosphatase in HRT-18, a human rectal cancer cell line", Cancer Res 42(11) 4540-4545 (1982).
Mueller et al., "Hodgkin's disease and Epstein-Barr virus. Altered antibody pattern before diagnosis", N Engl J Med 320(11) 689-695 (1989).
Nagai et al., "Studies on the synergistic action and anti-ulcerous activity of cortisone-GABOB", Arzneimittelforschung 21(1) 96-97 (1971).
Nagel et al., "F reticulocyte response in sickle cell anemia treated with recombinant human erythropoietin: a double-blind study", Blood 81(1) 9-14 (1993).

Nagel et al., "Structural bases of the inhibitory effects of hemoglobin F and hemoglobin A2 on the polymerization of hemoglobin S", Proc Natl Acad Sci USA 76(2) 670-672 (1979).
Naguib et al., "Effects of N,N-dimethylformamide and sodium butyrate on enzymes of pyrimidine metabolism in cultured human tumor cells", Leuk Res 11(10) 855-861 (1987).
Nathan et al., "Regulation of Fetal Hemoglobin Synthesis in the Hemoglobinopathies", Annals of the New York Academy of Sciences 445(1) 177-187 (1985).
Newman et al., "Induction of the insulin receptor and other differentiation markers by sodium butyrate in the Burkitt lymphoma cell, Raji", Biochem Biophys Res Commun 161(1) 101-106 (1989).
Newman et al., "Sodium n-butyrate enhancement of prostaglandin D2 antitumor efficacy", Biochem Pharmacol 34(20) 3771-3774 (1985).
Ney et al., "Tandem AP-1-binding sites within the human beta-globin dominant control region function as an inducible enhancer in erythroid cells", Genes Dev 4(6) 993-1006 (1990).
Niedobitek et al., "Epstein-Barr virus gene expression in Hodgkin's disease", Blood 78(6) 1628-1630 (1991).
Niedobitek et al.,"The role of Epstein—Barr virus in the pathogenesis of Hodgkin's disease", Annals of Oncology 7 (Suppl 4) S11-S17 (1996).
Nienhuis et al., "Pharmacological manipulation of fetal hemoglobin synthesis in patients with severe beta-thalassemia", Ann NY Acad Sci 445; 198-211 (1985).
Nisli et al., "Recombinant human erythropoietin trial in thalassemia intermedia", Journal of Tropical Pediatrics 42(6) 330-334 (1996).
Noguchi et al., "Inhibition of sickle hemoglobin gelation by amino acids and related compounds", Biochemistry 17(25) 5455-5459 (1978).
Noguchi et al., "Levels of fetal hemoglobin necessary for treatment of sickle cell disease", N Engl J Med 318(2) 96-99 (1988).
Novogrodsky et al., "Effect of polar organic compounds on leukemic cells. Butyrate-induced partial remission of acute myelogenous leukemia in a child", Cancer 51(1) 9-14 (1983).
Nudel et al., "Differential effects of chemical inducers on expression of beta globin genes in murine erythroleukemia cells". Proc Natl Acad Sci USA 74(3) 1100-1104 (1977).
Nudelman et al., "Novel anticancer prodrugs of butyric acid. 2", J Med Chem 35(4) 687-694 (1992).
Oldfield et al., "Gene therapy for the treatment of brain tumors using intra-tumoral transduction with the thymidine kinase gene and intravenous ganciclovir", Hum Gene Ther 4(1) 39-69 (1993).
Olivia et al., "Histone hyperacetylation can induce unfolding of the nucleosome core particle", Nucleic Acids Res 18(9) 2739-2747 (1990).
O'Malley et al., "Adenovirus-mediated gene therapy for human head and neck squamous cell cancer in a nude mouse model", Cancer Res 55(5) 1080-1085 (1995).
Opportunistic AIDS disorders (retrieved from the internet on Apr. 27, 2012/, URL: http://web.archive.org/web/20081224061406/http://biology.kenyon.edu/slonc/span-med/immune/opport.htm.
Ormandy et al., "Coordinate regulation of oestrogen and prolactin receptor expression by sodium butyrate in human breast cancer cells", Biochem Biophys Res Commun 182(2) 740-745 (1992).
Osato et al., "Epstein-Barr virus and gastric carcinoma", Seminars in Cancer Biology 7(4) 175-182 (1996).
Pace et al., "Short-chain fatty acid derivatives induce fetal globin expression and erythropoiesis in vivo", Blood 100(13) 4640-4648 (2002).
Pagano et al., "Epstein-Barr virus: the first human tumor virus and its role in cancer", Proc Assoc Am Physicians 111(6) 573-580 (1999).
Parise et al., "Liquid chromatography-mass spectrometric assay for quantitation of the short-chain fatty acid, 2,2-dimethylbutyrate (NSC 741804), in rat plasma", J Chromatogr B Analyt Technol Biomed Life Sci862(1-2) 168-174 (2008).
Partington et el., "Human globin gene transcription in injected Xenopus oocytes: enhancement by sodium butyrate", EMBO J 3(12) 2787-2792 (1984).
Patel et al., "Transcriptional activation potential of normal and tumor-associated myb isoforms does not correlate with their ability

(56) References Cited

OTHER PUBLICATIONS to block GCSF-induced terminal differentiation of murine myeloid precursor cells", Oncogene 13(6) 1197-1208 (1996).
PCT/US10/59584 Search Report and Written Opinon dated Feb. 11, 2011.
Perez et al., "Bryostatin-1 synergizes with histone deacetylase inhibitors to reactivate HIV-1 from latency", Curr HIV Res 8(6) 418-429 (2010).
Perrine et al., "A phase 1/2 trial of arginine butyrate and ganciclovir in patients with Epstein-Barr virus-associated lymphoid malignancies", Blood 109(6) 2571-2578 (2007).
Perrine et al., "A short-term trial of butyrate to stimulate fetal-globin-gene expression in the beta-globin disorders", N Engl J Med 328(2) 81-86 (1993).
Perrine et al., "An interleukin 2/sodium butyrate combination as immunotherapy for rat colon cancer peritoneal carcinomatosis", Gastroenterology 107(6) 1697-1708 (1994).
Inati et al., "Beta-thalassemia: the Lebanese experience", Clin Lab Haematol 28(4) 217-227 (2006).
International Search Report and written opinon dated Dec. 15, 2010 for PCT Application No. US10/50191.
International search report dated Jan. 2, 1995 for PCT Application No. US94/11565.
International Search report dated Oct. 12, 2000 for PCT Application No. US1999/03014.
International Search Report dated Mar. 2, 2010 PCT Application No. US20090/69035.
International Search Report dated Sep. 30, 2006 for PACT Application No. US 1996/02907.
Jaffe et al., "Classification of cytotoxic T-cell and natural killer cell lymphomas", Semin Hematol 40(3) 175-184 (2003).
Jane et al., "Hemoglobin switching in man and chicken is mediated by a heteromeric complex between the ubiquitous transcription factor CP2 and a developmentally specific protein", EMBO 14(1) 97-105 (1995).
Jiang et al., "cMYB is involved in the regulation of fetal hemoglobin production in adults", Blood 108(3) 1077-1083 (2006).
Jiwa et al., "Epstein-Barr virus DNA in Reed-Sternberg cells of Hodgkin's disease is frequently associated with CR2 (EBV receptor) expression", Histopathology 21(1) 51-57 (1992).
Johansson et al., "Epstein-Barr virus (EBV)-associated antibody patterns in malignant lymphoma and leukemia I. Hodgkin's disease", International Journal of Cancer 6(3) 450-462 (1970).
Johnson et al., "L-carnitine for treatment of distal ulcerative colitis", Gastroenterology 103(5) 1709-1710 (1992).
Jones et al., "T-cell lymphomas containing Epstein-Barr viral DNA in patients with chronic Epstein-Barr virus infections", N Engl J Med 318(12) 733-741 (1988).
Kanavaros et al., "Nasal T-cell lymphoma: a clinicopathologic entity associated with peculiar phenotype and with Epstein-Barr virus", Blood 81(10) 2688-2695 (1993).
Karlsson et al., "Developmental regulation of human globin genes", Annu Rev Biochem 54;1071-1108 (1985).
Kato et al., "Deconstructing sickle cell disease: reappraisal of the role of hemolysis in the development of clinical subphenotypes", Blood Rev 21(1) 37-47 (2007).
Kattamis et al., "Treatment of thalassemia with hydroxyurea: an indispensable alternative therapy", J Pediatr Hematol Oncol 29(11) 729-730 (2007).
Kawa et al., "Epstein-Barr virus-associated disease in humans", International Journal of Hematology 71(2) 108-117 (2000).
Keedy et al., "A limited group of class I histone deacetylases acts to repress human immunodeficiency virus type 1 expression", Journal of Virology 83(10) 4749-4756 (2009).
Kim et al., "Modification of thermosensitivity of HeLa cells by sodium butyrate, dibutyryl cyclic adenosine 3':5'-monophosphate, and retinoic acid", Cancer Res 44(2) 697-702 (1984).
Kirk et al., "Arginine stimulates wound healing and immune function in elderly human beings", Surgery 114(2) 155-159 (1993).

Kleer et al., "Detection of Epstein-Barr virus in rapidly growing fibroadenomas of the breast in immunosuppressed hosts", Mod Pathol 15(7) 759-764 (2002).
Koeffler et al., "Induction of differentiation of human acute myelogenous leukemia cells: therapeutic implications", Blood 62(4) 709-712 (1983).
Konstan et al., "Effect of high-dose ibuprofen in patients with cystic fibrosis", N Engl J Med 332(14) 848-854 (1995).
Korbjuhn et al., "Frequent latent Epstein-Barr virus infection of neoplastic T cells and bystander B cells in human immunodeficiency virus-negative European peripheral pleomorphic T-cell lymphomas", Blood 82(1) 217-223 (1993).
Koren et al., "Response to hydroxyurea therapy in β-thalassemia", American Journal of Hematology 83(5) 366-370 (2008).
Krantis et al., "Augmentation of cysteamine-induced ulceration of rat duodenum by systemically administered gamma-aminobutyric acid (GABA).", Dig Dis Sci 34(8) 1211-1216 (1989).
Kwong et al., "Natural killer cell lymphoma/leukemia: pathology and treatment", Hematol Oncol 15(2) 71-79 (1997).
Labie et al., "Common haplotype dependency of high G gamma-globin gene expression and high Hb F levels in beta-thalassemia and sickle cell anemia patients", Proc Natl. Acad. Sci USA 82(7) 2111-2114 (1985).
Langdon et al., "Effect of sodium butyrate and other differentiation inducers on poorly differentiated human ovarian adenocarcinoma cell lines", Cancer Res 48(21) 6161-6165 (1988).
Lea et al., "Butyramide and monobutyrin: growth inhibitory and differentiating agents", Anticancer Res 13(1) 145-149 (1993).
Leavitt et al., "Butyric acid suppression of the in vitro neoplastic state of Syrian hamster cells", Nature 271(5642) 262-265 (1978).
Leder et al., "Differentiation of erythroleukemic cells in the presence of inhibitors of DNA synthesis", Science 190(4217) 893-894 (1975).
Lee et al., "The association of Epstein-Barr virus with smooth-muscle tumors occurring after organ transplantation", N Engl J Med 332(1) 19-25 (1995).
Leoncini et al., "Epstein-Barr virus and gastric cancer: data and unanswered questions", Int J Cancer 53(6) 898-901 (1993).
Letvin et al., "Augmentation of fetal-hemoglobin production in anemic monkeys by hydroxyurea", N Engl J med 310(14) 869-873 (1984).
Ley et al., "5-Azacytidine increases gamma-globin synthesis and reduces the proportion of dense cells in patients with sickle cell anemia", Blood 62(2) 370-380 (1983).
Ley et al., "5-azacytidine selectively increases gamma-globin synthesis in a patient with beta+ thalassemia", N Engl J Med 307(24) 1469-1475 (1982).
Liakopoulou et al., "Induction of fetal hemoglobin by propionic and butyric acid derivatives: correlations between chemical structure and potency of Hb F induction", Blood Cells, Molecules and Disease 29(1) 48-56 (2002).
Liakopoulou et al., "Stimulation of fetal hemoglobin production by short chain fatty acids", Blood 86(8) 3227-3235 (1995).
Liakopoulou et al., "Structural features of short chain fatty acid-derived inducers of fetal hemoglobin", Abstract of ASH Annual Meeting, Seattle, WA Dec. 1995.
Lilbert et al., "Common vascular changes in the jugular vein of saline controls in continuous infusion in the beagle dog", Toxicol Pathol 32(6) 694-700 (2004).
Little et al., "Metabolic persistence of fetal hemoglobin", Blood 85(7) 1712-1718 (1995).
Lokeshwar et al., "Enhancement of radiation response of prostatic carcinoma by taxol: therapeutic potential for late-stage malignancy", Anticancer Res 15(1) 93-98 (1995).
Magrath et al., "Breast cancer: a new Epstein-Barr virus-associated disease?", J Natl Cancer Inst 91(16) 1349-1350 (1999).
Maia et al., "Chronic, active Epstein-Barr virus infection", Current Opinion 7(1) 59-63 (2000).
Mankidy et al., "Short-chain fatty acids induce γ-globin gene expression by displacement of a HDAC3-NCoR repressor complex", Blood 108(9) 3179-3186 (2006).

(56) References Cited

OTHER PUBLICATIONS

Mares et al., "Evaluation of gas chromatograph packings for the separation of butyric acid from serum-catalyzed hydrolysis of ethyl butyrate", Anal Biochem 90(2) 824-928 (1978).

Matalon et al., "The histone deacetylase inhibitor ITF2357 decreases surface CXCR4 and CCR5 expression on CD4(+) T-cells and monocytes and is superior to valproic acid for latent HIV-1 expression in vitro", J Acquir Immune Defic Syndr 54(1) 1-9 (2010).

Mathias et al., "Ineffective erythropoiesis in beta-thalassemia major is due to apoptosis at the polychromatophilic normoblast stage", Exp Hematol 28(12) 1343-1352 (2000).

\* cited by examiner

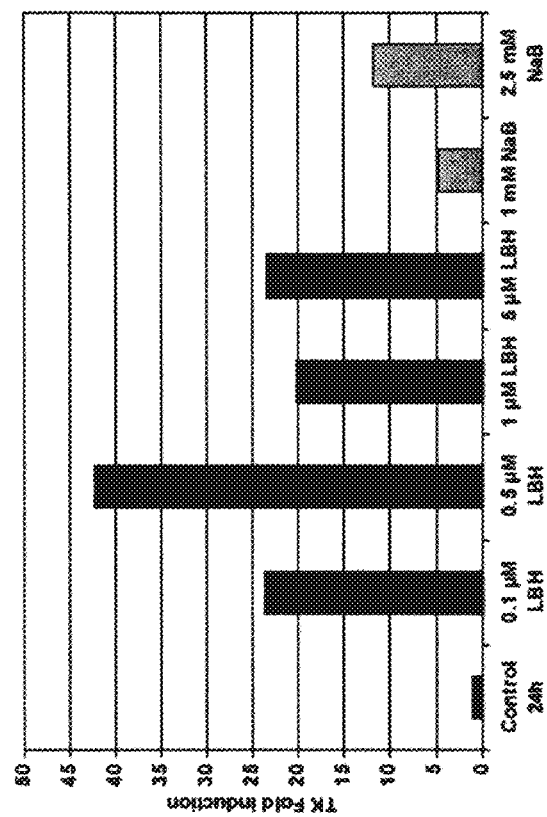
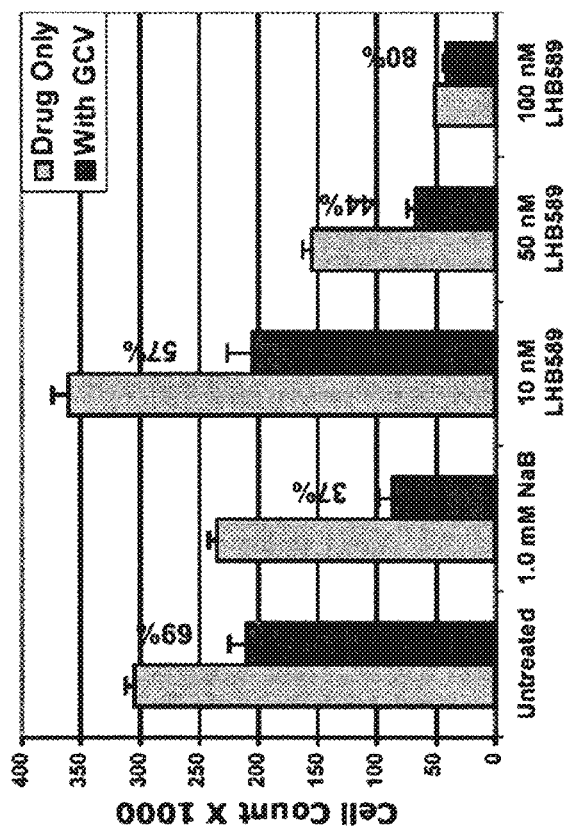
FIG. 6A
FIG. 6B ab6-113b largazole
ab6-113a largazole thiol
ab6-123a largazole thiol peptide isostere
ab6-123b largazole peptide isostere
ab6-164b largazole analog with MS 275 zinc-binding arm Largazole and Analogs

METHODS FOR TREATING VIRAL DISORDERS

CROSS-REFERENCE TO RELATED APPLICATIONS

This application is a continuation application of co-depending U.S. patent application Ser. No. 14/819,024 filed Aug. 5, 2015; which is a continuation application of U.S. patent application Ser. No. 14/624,852 filed Feb. 18, 2015; which is a continuation application of U.S. patent application Ser. No. 13/915,092 filed Jun. 11, 2013, now U.S. Pat. No. 8,993,581, issued Mar. 31, 2015; which is a continuation application of U.S. patent application Ser. No. 12/890,042 filed on Sep. 24, 2010, now abandoned; which claims the benefit under 35 U.S.C. § 119(e) of U.S. Provisional Application No. 61/245,529, filed Sep. 24, 2009, and U.S. Provisional Application No. 61/295,663, filed Jan. 15, 2010, the contents of each of which are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Aug. 5, 2015, is named 701586-069032_SL.txt and is 1,244 bytes in size.

BACKGROUND OF THE INVENTION

A growing number of cellular disorders such as neoplastic malignancies have been found to contain viral genetic sequences or virus particles in the anomalous cells. For a large number of these disorders, the presence of the virus is believed to be a causative or at least contributory instrument. Representative members of many of the known families of viruses have been found in such cells including members of the herpes family of viruses, the polyomaviruses, and the hepatitis viruses. Epstein-Barr virus (EBV), a 172 kb herpes virus, is often found intimately associated with both mature and immature B cells. EBV is a common and worldwide pathogen. Childhood infection is asymptomatic. About 50% of individuals with delayed exposure develop a self-limited, lymphoproliferative syndrome referred to as infectious mononucleosis. EBV is also detected in 2 endemic tumors, African Burkitt's lymphoma (BL) (Henle, G., et al. 1985 Proc. Natl. Acad. Sci. USA 58:94-101) and nasopharyngeal carcinoma (NPC) (Henle, W., et al. 1985 Adv. Viral Onco. 5:201-38), as well as gastric carcinoma, breast cancers and sarcomas. Recently, some T-cell and B-cell lymphomas, as well as about 50% of Hodgkin's lymphomas, have been found to contain EBV (Weiss, L. M., et al. 1989 N Engl. J Med. 320:502).

EBV undergoes lytic replication after initial infection of oropharyngeal epithelia. The linear form genome is duplicated, packaged into the viral capsid, and extruded from the cell by budding or lysis. One hundred viral proteins are synthesized during this lytic stage of the virus life cycle. In contrast, normal B cells incubated with EBV in vitro are efficiently immortalized and develop into continuously growing lymphoblastoid cell lines (LCLs). The cellular events that regulate these distinct outcomes are as yet unclear. In immortalized cells, the genome circularizes, amplifies, and replicates coordinate with, and dependent upon, cell division. Because no viral particles are produced, infection is considered to be latent, and EBV persists in the cells for life. Outgrowth of latently infected B cells is prevented by T cell immune surveillance. In immortalizing latent infection, only 11 gene products are detected, including 6 nuclear antigens (EBNA-1, -2, -LP, -3A, -3B, -3Q), 3 membrane proteins (LMP-1, LMP-2A, LMP-2B) and two small, non-poly(A) RNAs (EBER-1 and EBER-2) (Miller, G., et al. 1990 Epstein-Barr Virus: Biology, Pathogenesis and Medical Aspects, Raven Press, N.Y.). In EBV(+) tumors such as Burkitt's lymphoma, neoplastic genetic events have often superseded the requirement for viral immortalizing functions, and gene expression may be limited to EBNA-1 (Rowe, M., et al. 1987 EMBO J. 6:2743-51). Virus tropism is deteimined by complement receptor type 2 which mediates attachment of the envelope protein gp350/2204 to B and some T lymphocytes, follicular dendritic cells and epithelial cells.

African Burkitt's lymphoma is characterized by rapid growth of the tumor at non-lymphoid sites such as the jaw or the retroperitoneum. The tumor is of B cell origin and is closely related to the small non-cleaved cells of normal lymphoid follicles. Biopsy specimens from African Burkitt's lymphoma invariably contain the EBV genome and are positive for EBNA (Magrath, I. 1986 Epstein-Barr Virus and Associated Diseases, pp. 631-43, M. Ninjhoff Publishing, Boston). This contrasts with the non-African Burkitt's lymphoma, in which only 15% to 20% of the tumors contain the EBV genome. EBV has a worldwide distribution and infects most (more than 90%) individuals before adulthood. The clustering of Burkitt's lymphoma in the equatorial belt of East Africa remains unexplained. It has been hypothesized that alterations of the immune system, possibly due to hyperstimulation by endemic malaria, may play an important role in the outcome of an EBV infection to individuals in this region (Moss, D. J., et al. 1983 Int. J. Cancer 31: 727-32). Individuals from this region show impairment in virus-specific cytotoxic T-cell activity. Normally, it is the T-cell response to EBV infection that limits B-cell proliferation, and this T-cell response is directly stimulated by EBV (zur Hausen, H., et al. 1970 Nature 228: 1056-58). It has been postulated that the failure of the T-cell immune response to control this proliferation could lead to excessive B-cell proliferation and, as such, provide a suitable background for further mutation, oncogenic transformation, and lymphomagenesis.

A scenario has been suggested for the involvement of EBV in the etiology of African Burkitt's lymphoma (Klein, G. 1979 Proc. Natl. Acad. Sci. USA 76:2442-46). The first step involves the EBV-induced immortalization of B lymphocytes in a primary infection. The second step involves the stimulated proliferation of EB V(+) B cells. This step is facilitated in the geographic areas where Burkitt's lymphoma is endemic (presumably because of the presence of malaria), through B-cell triggering and the suppression of T-cells involved in the control of the proliferation of EBV-infected cells. This pool of cells becomes increased in size as a target cell population for random chromosomal rearrangements. The third and final step is the reciprocal translocation involving a chromosomal locus with an immunoglobulin gene and the c-myc gene on chromosome 8. This leads to the deregulation of the c-myc gene, to the development of the malignant clone, and to the appearance of a tumor mass (Klein, G., et al. 1985 Nature 315: 190). Alternative scenarios have been proposed, in which the order of the steps is rearranged such that the B-cell activation by malaria precedes the chromosomal translocation and is followed by EBV infection. Regardless, the components of these two scenarios each account for the geographic distribution of Burkitt's lymphoma, the critical involvement of EBV in lymphomagenesis, and the eventual selection and clonal outgrowth of a population of cells with the critical translocation involving the deregulation of the c-myc gene on chromosome 8.

For more than 20 years, a role for EBV in the pathogenesis of Hodgkin's disease (HD) was postulated based on epidemiologic evidence linking Hodgkin's patients with EBV seropositivity and elevated EBV titers (Evans, A. S., et al. 1984 *Int. J. Cancer* 34: 149). A number of studies have found an increase (2-5 fold) in the incidence of HD after infectious mononucleosis. However, some Hodgkin's patients were seronegative for EBV, and the association between EBV and Hodgkin's disease remained speculative until 1987. In that year, molecular genetic analysis demonstrated that some Hodgkin's tissues contained monoclonal EBV DNA and that the virus was localized to Reed-Sternberg (RS) cells (the malignant cells in HD). Subsequent immunohistochemical and serologic data support an association between EBV and Hodgkin's disease and confirm the localization of the virus to cytologically malignant-appearing RS cells and variants (Jiwa, N. M., et al. 1992 *Histopathology* 21:51). EBV also infects variable numbers of small B and T lymphocytes in the reactive inflammatory cell infiltrate that composes the bulk of Hodgkin's tissues (Weiss, L. M., et al. 1991 *Am. J. Path.* 139: 1259). Clonal and non-clonal EBV genomes are present in Hodgkin's disease. Expression of the oncogene LMP (latent membrane protein) is seen in RS cells. In HD, the region of the (viral) BNLF1 oncogene coding for the amino terminal and transmembrane domains (associated with oncogenic function) of LMP appears to be homogeneous, whereas the region coding for the intracytoplasmic (carboxyl terminal) domain of LMP is heterogeneous. Cytological similarities between RS cells and immunoblasts of known EBV-induced infectious mononucleosis and EBV-induced AIDS-related lymphomas are consistent with the hypothesis that the EBV-BNLFI oncogene is an inducer of morphological features of RS cells. Whether chromosomal integration of EBV DNA is an important factor in activation of such a transforming activity remains to be elucidated. Therefore, the RS cells appear to be derived from lymphocytes beyond the pre-B-cell or common thymocyte stage, which may or may not subsequently become infected by EBV.

The high prevalence of EBV in Hodgkin's disease implies an etiologic role for the virus in some cases of Hodgkin's tumorigenesis. This pathogenetic theory is supported by the monoclonality of EBV DNA in these tumors (Gulley, M. L., et al. 1994 *Blood* 83: 1595-602). In one series, monoclonal EBV DNA was detected in all 17 cases having EBNA1-positive RS cells. Because tumor-associated viral DNA is monoclonal, it is likely that virus infection preceded clonal expansion. This reinforces the hypothesis that the virus is not an innocent bystander, but, rather, plays a role in the pathogenesis of the Hodgkin's disease and the other tumor types in which it is found (Neri, A., et al. 1991 *Blood* 77: 1092). The observation of EBNA1 expression in the RS cells of clonally-infected cases indicates that the clonal virus is localized to these cells and suggests that Hodgkin's disease results from the transformation of an EBV-competent cell. Other studies suggest that this virus is a modulating rather than an etiologic agent in a considerable proportion of HD cases.

Investigations into the biology of EBV infection have shown that only one viral particle successfully infects a given cell. Once the viral DNA is established inside the cell, it circularizes and reproduces itself to yield multiple identical copies of viral DNA (Hurley, E. A., et al. 1988 *J. Exp. Med.* 168:2059). In this way, tumors derived from infected cells can have multiple copies of EBV per cell, while maintaining clonal viral DNA structure. The average amount of clonal EBV DNA in Hodgkin's disease tissues varied from 0.5 to 5 copies per cell. Because RS cells comprised only a small fraction (<1%) of all HD tissue cells, the content of EBV DNA in each RS cell is estimated to be at least 100 times higher than the measured average copy number per cell, or at least 50 copies of viral DNA per RS cell. This is comparable with, or greater than, the viral burden in infected non-Hodgkin's lymphomas. The high copy number of EBV in RS cells may relate to the pathobiology of this complex lymphomatous disorder. In agreement with these studies, EBV DNA is abundant and monoclonal in infected RS cells. The presence of EBV in RS cells was strongly and independently linked to mixed cellularity histology and Hispanic ethnicity.

Clonally-integrated EBV is found in association with T-cell lymphomas, as well as B-cell lymphomas. Currently, three populations of tissue-restricted T lymphocytes have been recognized: mucosa-associated, cutaneous, and nodal T lymphocytes. T-cell lymphomas arising from different sites, but with similar morphology, may show differences in lymphomagenesis and in expression of oncogenes, adhesion molecules, presence of certain DNA/RNA viral sequences, and in clinical presentation and behavior. Primary cutaneous CD30(+) large cell, T-cell lymphomas often remain localized to the skin for a long time, express a unique cutaneous lymphocyte antigen (CLA), known as the skin-homing receptor, have been postulated to be associated with the presence of human T-cell leukemia/lymphoma virus type I (HTLV 1), and have a good clinical course (Beljaards, R. C., et al. 1993 *Cancer* 71:2097). In contrast, morphologically similar T-cell lymphomas of nodal origin often behave more aggressively, are CLA-negative, and have been associated with the presence of EBV (de Bruin, P. C., et al. 1993 *Histopathology* 23: 127). There was no relation between primary cutaneous T-cell lymphoma and EBV.

Infection of T cells by EBV most likely occurs via CR2 or CR2-like receptors (Tsoukas, C. D., et al. 1993 *Inununol. Today* 14:56). The close contact between T cells and the upper respiratory tract epithelium, known for its reservoir function for EBV, probably make T cells in this region more vulnerable for EBV infection. The finding that EBV can be found in almost all tumor cells in most cases of primary extra-nodal, and especially nasal, T-cell lymphoma, in contrast to primary nodal T-cell lymphoma, where the number of EB V-infected neoplastic cells varies greatly between the cases, argues for an etiologic role for EBV in these cases. Moreover, these cases often express LMP-1, known for its transforming and oncogenic properties in vitro and are reported to be monoclonal for EBV (Su, I., et al. 1991 *Blood* 77:799). Thus, there are site-restricted etiologic differences between morphologically identical T-cell lymphomas, of which EBV might be one of many factors.

EBV-induced lymphoproliferative disease or lymphoma has an immunodeficiency incidence in U.S. of about 10,000 B-cell, EBV(+) lymphoma patients per year. EBV is very commonly associated with lymphomas in patients with acquired or congenital immunodeficiencies. These lymphomas can be distinguished from the classical Burkitt's lymphomas in that the tumors may be polyclonal. Tumors also do not demonstrate the characteristic chromosomal abnormalities of Burkitt's lymphoma described earlier. The pathogenesis of these lymphomas involves a deficiency in the effector mechanisms needed to control EBV-transformed cells. The prototypic model for this disease has been the X-linked lymphoproliferative (XLP) syndrome (Purtilo, D. T., et al. 1982 *Am. J. Med.* 73:49-56). Patients with XLP who develop acute infectious mononucleosis exhibit the usual atypical lymphocytosis and polyclonal elevation of serum immunoglobulins and increases in specific antibody to VCA and to EA. During these infections, patients with XLP fail to mount and sustain an anti-EBNA response after acute EBV infection. The unique vulnerability of males with XLP to EBV infection is most likely due to an inherited immune regulatory defect that results in the failure to govern the cytotoxic T cells and NK cells required to cope with EBV.

The herpes virus family members are capable of bypassing the butyrate-mediated block, which is probably due to the role of viral early genes in DNA synthesis, such as the viral DNA polymerase, DNA-binding protein, and helicase genes (Shadan, F. F., et al. 1994 *J. Virol.* 68:4785-96). Butyrate treatment has been reported to result in the induction of the major CMV major immediate-early protein (IEP) by activating the IEI promoter via cellular factors in a human epithelial thyroid papilloma carcinoma cell line and in cultured endothelial cells under conditions that are conducive to terminal differentiation (Villarreal, L. P. 1991 *Microbiol. Rev.* 55:512-42). Similarly, EBV early antigen is induced by butyrate in the P3HR-1 cell line, as well as in Raji and NC37 cell lines. These results indicate that butyrate exerts some of its effects on viral growth at the level of gene transcription. This conclusion is also supported by the observation that butyrate activates the long terminal repeat-directed expression of human immunodeficiency virus and induces the Moloney murine sarcoma virus via a putative butyrate response enhancer-promoter element (Bohan, C., et al. 1987 *Biochem. Biophys. Res. Commun.* 148:899-907; Tang, D. C., et al. 1992 *Biochem. Biophys. Res. Commun.* 189: 141-47; Yeivin, A., et al. 1992 *Gene* 116: 159-64). Therefore, butyrate appears to be associated with a general induction of early viral proteins. Butyrate has been reported to exert additional cytostatic effects such as G2/M blockage and anti-viral activity against RNA viruses.

Unlike other members of the herpes virus family, EBV is resistant to the antiviral agent ganciclovir, because of low levels of viral thymidine kinase. Acyclovir and ganciclovir have also been used to treat AIDS patients, many of whom had an active EBV infection. During treatment, regression of hairy leukoplakia, an EBV disorder, was inadvertently observed while latent EBV infection was unaffected. Additional studies demonstrated that even when virus production is minimal, expression of many EBV genes active during the lytic cycle, such as thymidine kinase, can be induced. Therefore, exposure of EBV-transformed B-cells or tumor cells to arginine butyrate induces EBV-TK and renders them sensitive to ganciclovir.

Like herpes simplex virus (HSV) and varicella-zoster virus (VZV), EBV encodes a thymidine kinase enzyme localized to the BamHI, X fragment of the genome. In a rate-limiting step, the TK converts nucleoside analogs to their monophosphate form. Cellular enzymes complete their conversion to biologically-active triphosphates. A viral DNA polymerase preferentially incorporates the toxic metabolites into viral DNA, leading to premature termination of the nascent DNA. ACV is a purine nucleoside analog with a linear side chain replacing the cyclic sugar of guanosine. GCV differs from ACV in the addition of a hydroxymethyl group to the side chain. However, ACV and GCV differ in functional assays. Whereas HSV TK preferentially phosphorylates ACV, EBV-TK preferentially phosphorylates GCV. Furthermore, because GCV triphosphate accumulates to higher levels and persists for longer periods in infected cells than ACV, GCV produces more interference with cellular DNA synthesis than occurs with ACV. In one study, selective toxicity of GCV for cells expressing HSV-TK was utilized to promote tumor killing in the CNS. Rapidly dividing murine glioma cells were infected in vivo with an amphotropic retrovirus containing HSV-TK. Animals were treated with GCV, which killed TK+tumor cells, sparing adjacent normal cells that replicated too slowly for efficient infection and viral TK expression.

EBV-induced lymphomas are associated with immunosuppression. Patients with iatrogenic immunodeficiencies, such as organ transplant recipients, are also at an increased risk for lymphomas, and these lymphomas often contain EBV DNA and EBNA. Also, patients with AIDS are at a higher risk for developing polyclonal lymphomas associated with EBV. EBV-associated lymphoproliferative disease (EBV-LPD) is characterized by actively proliferating EBV (+) B-cells, frequently without overt malignant change. These immunoblastic lymphoma-like lesions have been identified in a variety of transplant patients, in patients with congenital immunodeficiency, and in patients infected with HIV (Cohen, J. I. 1991 *Medicine* 70: 137-60). These so called post-transplant lymphoproliferative disorders (PTLD) are observed after all transplants, including kidney, bone marrow, heart, liver, and lung transplantation. This increased incidence of EBV-LPD in this setting is likely due to the aggressive immunosuppression required after these transplants.

Although there are case reports of administration of inducing agents such as butyrates to patients for the treatment of malignancies (Novogrodsky, A., et al. 1983 *Cancer* 51:9-14; Miller, A. A., et al. 1987 *Eur. J. Cancer Clin. Oncol.* 23: 1283-89), as well as of administration of anti-viral agents for the treatment of viral disorders, there are no treatments requiring the administration of both agents and involving a short course regimen.

Thus, there remains a need for effective regimens for treatment of viral-associated disorders.

SUMMARY OF THE INVENTION

In one aspect, the invention is directed to a method for treating a viral disorder in a subject, comprising providing said subject with at least one cycle of therapy, said cycle of therapy comprising: i) administering to the subject over a first period an inducing agent to induce expression of a viral gene product in a virus-infected cell of the subject and an anti-viral agent whose anti-viral activity is directed to the viral gene product expressed, wherein said first period of time is less than or equal to one-half of the length of the cycle, and further wherein said inducing agent and said anti-viral agent are administered in the same or separate compositions; and ii) administering said anti-viral agent to the subject for a second period, wherein said second period is the remainder of the cycle. The first wherein period may be less than or equal to about 5 days, and the second period may be at least about 5 days and less than or equal to about 16 days. In various aspects, the method is a method for killing virus-infected cells in vivo.

In another embodiment of a method of the invention, the subject is provided less than or equal to about six cycles of therapy. In yet another embodiment of a method of the invention, the subject is provided more than or equal to six cycles of therapy. In still another embodiment of a method of the invention, the inducing agent is administered to the subject via continuous infusion over the first period of time, which, in another embodiment, is less than or equal to about five days. In still another embodiment of a method of the invention, the inducing agent is administered to the subject via once daily infusion over the first period of time, which, in another embodiment, is less than or equal to about five days. In still another embodiment of a method of the invention, the inducing agent is administered to the subject at least once over the first period of time, which, in another embodiment, is less than or equal to about five days.

In another embodiment of a method of the invention, the anti-viral agent is administered intravenously to the subject about one to about two times per day over the first period of time of the cycle and orally about one to about two times per day over the remainder of the cycle. In still another embodiment of a method of the invention, the inducing agent is administered at a dose of about 0.1 to about 2000 mg/kg/day or about 1 to about 100 mg/m²/day. In still another embodiment of a method of the invention the inducing agent is administered at a dose of about 1000 mg/kg/day. In still another embodiment of a method of the invention, the inducing agent is administered at a dose of about 5 mg/m²/wk.

In another embodiment of a method of the invention, the inducing agent is selected from the group consisting of a short-chain fatty acid, a short-chain fatty acid derivative, a histone deacetylase (HDAC) inhibitor, a DNA methyltransferase inhibitor, a proteasome inhibitor, a phorbol ester, an oxidized phorbol ester, ceramide, bryostatin, a cytokine, and combinations thereof. In another aspect, the inducing agent is selected from arginine butyrate, PMA (phorbol myristate acetate), TSA (trichostatin A), 2,2-dimethyl butyrate, panobinostat (LHB589), apicidin, MS-275, and largazole. In yet another embodiment of a method of the invention, the inducing agent is arginine butyrate.

In another embodiment of a method of the invention, the anti-viral agent is selected from the group consisting of an interferon, an amino acid analog, a nucleoside analog, an integrase inhibitor, a protease inhibitor, a polymerase inhibitor, and a transcriptase inhibitor. In still another embodiment of a method of the invention, the anti-viral agent is acyclovir (ACV), ganciclovir (GCV), famcyclovir, penciclovir, foscarnet, ribavirin, zalcitabine (ddC), zidovudine (AZT), stavudine (D4T), Iarnivudine (3TC), didanosine (ddI), cytarabine, dideoxyadenosine, edoxudine, floxuridine, idozuridine, inosine pranobex, 2'-deoxy-5-(methylamino) uridine, trifluridine or vidarabine. In still another embodiment of a method of the invention, the anti-viral agent is ganciclovir.

In another embodiment of a method of the invention, the inducing agent and the anti-viral agent are administered separately.

In another aspect, the invention provides a method for killing virus-infected cells in vivo, comprising providing a subject with at least one cycle of therapy, said cycle of therapy comprising: i) administering to the subject over a first period of time a pharmaceutical composition comprising an inducing agent to induce expression of a viral gene product in a virus-infected cell of the subject and an anti-viral agent whose anti-viral activity is directed to the viral gene product expressed, wherein said first period of time is less than or equal to one-half of the length of the cycle; and ii) continuing the administration of the anti-viral agent to the subject for the remainder of the cycle, thus killing the virus-infected cells in vivo. The administration periods may be about 5 days and about 16 days, for a cycle of about 21 days, in various embodiments.

In another embodiment of a method of the invention, the virus-infected cells are lymphocytes. In still another embodiment of a method of the invention, the virus-infected cells contain an integrated or episomal latent virus. In still another embodiment of a method of the invention, the virus-infected cells contain a herpes virus, a human T cell or B cell leukemia virus, an adenovirus, or a hepatitis virus. In still another embodiment of a method of the invention, the herpes virus is an Epstein-Barr virus (EBV) or a Kaposi's-associated human herpes virus. In still another embodiment of a method of the invention, the leukemia virus is a human immunodeficiency virus (HIV) or a human T-cell leukemia/lymphoma virus (HTLV).

In various embodiments, the viral disorder is a neoplasia associated with viral infection. Alternatively, the neoplasia is selected from the group consisting of lymphoma, Hodgkin disease, Burkitts lymphoma, post-transplantation lymphoproliferative disease, viral associated lymphoproliferative disease, hemophagocytic syndrome, nasopharyngeal carcinoma, gastric carcinoma, or breast cancer.

In various embodiments, the viral disorder is a non-malignant viral disorder.

In another embodiment of a method of the invention, the viral gene product regulates viral gene expression. In yet another embodiment of a method of the invention, the viral gene product is a viral enzyme, an oncogene or proto-oncogene, a transcription factor, a protease, a polymerase, a reverse transcriptase, a cell surface receptor, a structural protein, a major histocompatibility antigen, a growth factor, or a combination thereof. In yet another embodiment of a method of the invention, the viral enzyme is a thymidine or protein kinase. In yet another embodiment of a method of the invention, the gene product expressed sensitizes the infected-cells to the anti-viral agent. In various embodiments, induction of gene products that target the cell for destruction by the immune system are excluded such that the therapeutic action is essentially through the activity of the anti-viral agent.

In another aspect, the invention provides a method for treating a cellular disorder resulting from and/or associated with viral infection in a subject, comprising providing said subject with at least one cycle of therapy, said cycle of therapy comprising: i) administering to the subject over a first period of time a pharmaceutical composition comprising an activator and an anti-viral agent, wherein the activator is administered in an amount sufficient to activate expression of a latent virus episomal or integrated into proliferating cells of the subject, wherein said first period of time is less than or equal to one-half of the length of the cycle; and ii) continuing the administration of the anti-viral agent to the subject for the remainder of the cycle, thus treating the cellular disorder resulting from and/or associated with viral infection in the subject.

In another aspect, the invention provides a method for treating an HIV-associated disorder in a subject, comprising providing said subject with at least one cycle of therapy, said cycle of therapy comprising: i) administering to the subject over a first period of time: a) an anti-viral agent, and b) an inducing agent in an amount sufficient to induce expression of a viral gene product selected from the group consisting of EBV-thymidine kinase and HIV reverse transcriptase; and ii) continuing the administration of the anti-viral agent to the subject for the remainder of the cycle.

Other objects and advantages of the invention are set forth in part in the description of the invention that follows and, in part, will be apparent from this description or may be learned from the practice of the invention.

BRIEF DESCRIPTION OF THE DRAWINGS

FIGS. 1A and 1B show pre- and post-treatment, respectively.

FIGS. 2A and 2B show results from various concentrations of GCV and PCV.

FIG. 3A shows cell count results after using NaB. FIG. 3B shows results from VA. FIG. 3C shows fold of TK expression induced.

FIG. 4A shows cell count results after using scriptaid. FIG. 4B shows fold of TK expression induced.

FIG. 5A shows cell count results after using SAHA. FIG. 5B shows fold of TK expression induced.

FIGS. 6A-6B illustrate results from analysis of efficacy of anti-virals using LHB589 (Panobinostat) as an inducing agent. FIG. 6A shows cell count results after using LHB589. FIG. 6B shows fold of TK expression induced.

FIG. 8 shows cell count results after using oxamflatin.

FIG. 9 shows cell count results after using apicidin.

FIG. 10A shows cell count results after using MS-275. FIG. 10B shows fold of TK expression induced. FIG. 10C shows cell count results after treating cells in combination for shorter time periods.

FIGS. 12A, 12B, 12C, 12D and 12E show cell count results after using various largazole compounds. FIG. 12F shows fold of TK expression induced from various largazole compounds.

DETAILED DESCRIPTION OF THE INVENTION

Figure 1B:
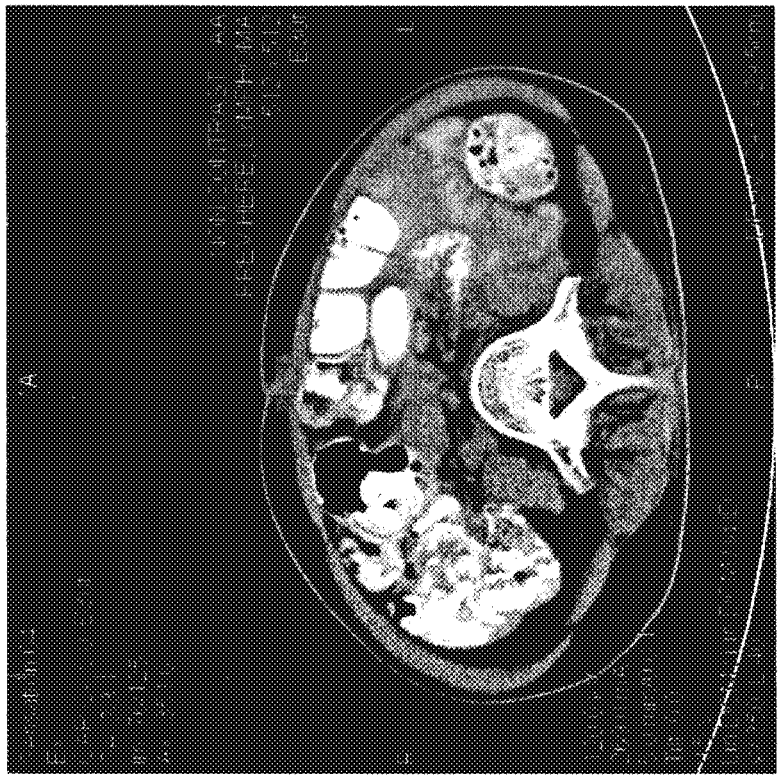
FIGS. 1A-1B illustrate CT scans of tumor reduction after treatment with arginine butyrate (AB) and GCV.

As embodied and broadly described herein, the present invention is directed to methods for the treatment and prevention of viral diseases and disorders. It has now been found that the relevant effect of an inducing agent lasts long after it has been administered and, even after the inducing agent is no longer detectable in the subject's plasma. In the currently described treatment regimen, one contemplated dose is 1000 mg/kg/day for 5 days (i.e., 5000 mg/kg) of inducing agent. It is surprising, for example, in virus-associated neoplastic disorders, that the dose of drug and the time span of its administration can be cut down dramatically—both the total amount of inducing agent administered, and the time span over which it is given.

In one aspect, the invention provides methods for treating virus-associated disorders. The methods comprise providing a subject with at least one cycle of therapy comprising administering over a first period of time a therapeutic agent, such as an anti-viral agent, and an inducing agent that stimulates the expression of a specific gene, such as a virus-associated gene, that renders the infected cell susceptible to further therapeutic treatment via a therapeutic agent such as an anti-viral agent, and subsequently, continuing to administer the therapeutic agent for the remainder of the cycle. The inducing agent is administered in a short course regimen (i.e., over the first period of time less than or equal to one half of the length of the cycle of therapy over which the therapeutic agent is given).

The inducing agents may induce expression of certain viral gene products. Gene products that can be induced by agents of the invention include, but are not limited to, viral proteins such as viral thymidine kinase and the BGLF4 protein kinase of EBV-infected cells. Expression of these products can be used in the treatment and prevention of viral disorders.

The therapeutic agents may comprise anti-viral agents that, for example, in combination with certain inducing agents, destroy virus-infected cells. Effective anti-viral agents that can be used include substrate analogs such as nucleoside analogs, polymerase inhibitors, and transcriptase inhibitors. Cells that demonstrate induced expression or proliferation are targeted and destroyed.

Another embodiment of the invention is directed to a method for destroying, killing or otherwise severely crippling virus-infected cells by treating said cells with an inducing agent, to induce the activity of a gene product, and an anti-viral agent whose anti-viral activity is directed to the activity of the gene product induced, over a first period of time less than or equal to one half of the duration of a cycle of therapy, followed by treatment with the anti-viral agent alone over the remainder of the cycle of therapy. The combination portion of the treatment course is, thus, a short course regimen.

Preferably, the gene product is a viral enzyme that relates to a basic and necessary process of the virus such as virus adsorption, cell penetration, fusion, uncoating, reverse transcription, integration, DNA replication, viral interference, viral transcription, the switch from early to late expression, the latent or lytic phases, the switch from a latent to lytic phase, defective-interfering particle production, virus assembly, capsid packaging, the generation of virus-specific membrane, virus budding and virus secretion. The activity of one or more of these processes may be enhanced by one or more of the inducing agents, and the enhanced activity is then targeted by one or more anti-viral agents. The combination treatment as part of the cycle of therapy is more effective than conventional treatment with anti-viral agents alone or simply allows for the administration of therapeutically effective amounts of the anti-viral agent that are less than what would be considered effective with conventional treatment regimens.

Another embodiment of the invention is directed to a method for treating a viral disorder in a patient comprised of administering an activator and an anti-viral agent to the patient, wherein the activator is administered in an amount sufficient to activate expression of a latent virus integrated into proliferating cells of the patient. The treatment regimen is as described above for the methods of the invention. Useful activators include phorbol ester, an oxidized phorbol ester, ceramide, bryostatin, an inducing agent, or a combination thereof. The activator should be administered in an amount sufficient to activate, for example, protein kinase C, an oncogene, a thymidine kinase or other viral kinases, AP-1, AP-2, Sp-1 or NF-KB.

A. Definitions

The terms "viral" and "virus-associated" with reference to disorders are used interchangeably throughout the instant specification.

The term "treating", as used herein, refers to altering the disease course of the subject being treated. Therapeutic effects of treatment include, without limitation, preventing occurrence or recurrence of disease, alleviation of symptom (s), diminishment of direct or indirect pathological consequences of the disease, decreasing the rate of disease progression, amelioration or palliation of the disease state, and remission or improved prognosis.

The term "pharmaceutically acceptable excipient", as used herein, refers to carriers and vehicles that are compatible with the active ingredient (for example, a compound of the invention) of a pharmaceutical composition of the invention (and preferably capable of stabilizing it) and not deleterious to the subject to be treated. For example, solubilizing agents that form specific, more soluble complexes with the compounds of the invention can be utilized as pharmaceutical excipients for delivery of the compounds. Suitable carriers and vehicles are known to those of extraordinary skill in the art. The term "excipient" as used herein will encompass all such carriers, adjuvants, diluents, solvents, or other inactive additives. Suitable pharmaceutically acceptable excipients include, but are not limited to, water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical compositions of the invention can also be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like, which do not deleteriously react with the active compounds of the invention.

The term "subject" as used herein refers to a vertebrate, preferably a mammal, more preferably a primate, still more preferably a human. Mammals include, without limitation, humans, primates, wild animals, feral animals, farm animals, sports animals, and pets.

The term "obtaining" as in "obtaining the composition" is intended to include purchasing, synthesizing, or otherwise acquiring the composition (or agent(s) of the composition).

The terms "comprises", "comprising", are intended to have the broad meaning ascribed to them and can mean "includes", "including" and the like.

The invention can be understood more fully by reference to the following detailed description and illustrative examples, which are intended to exemplify non-limiting embodiments of the invention.

B. Viruses and Viral (Including Virus-Associated) Disorders

The methods and compositions of the provided invention can be used to treat and/or prevent viral infections. The virus causing the infection can be a member of the herpes virus family, a human immunodeficiency virus, parvovirus, or coxsackie virus. A member of the herpes virus family can be herpes simplex virus, herpes genitalis virus, varicella zoster virus, Epstein-Barr virus, human herpesvirus 6, or cytomegalovirus.

The methods and compositions described herein can be used to treat and/or prevent infections caused by any virus, including, for example, Abelson leukemia virus, Abelson murine leukemia virus, Abelson's virus, Acute laryngotracheobronchitis virus, Adelaide River virus, Adeno associated virus group, Adenovirus, African horse sickness virus, African swine fever virus, AIDS virus, Aleutian mink disease parvovirus, Alpharetrovirus, Alphavirus, ALV related virus, Amapari virus, Aphthovirus, Aquareovirus, Arbovirus, Arbovirus C, arbovirus group A, arbovirus group B, Arenavirus group, Argentine hemorrhagic fever virus, Argentine hemorrhagic fever virus, Arterivirus, Astrovirus, Ateline herpesvirus group, Aujezky's disease virus, Aura virus, Ausduk disease virus, Australian bat lyssavirus, Aviadenovirus, avian erythroblastosis virus, avian infectious bronchitis virus, avian leukemia virus, avian leukosis virus, avian lymphomatosis virus, avian myeloblastosis virus, avian paramyxovirus, avian pneumoencephalitis virus, avian reticuloendotheliosis virus, avian sarcoma virus, avian type C retrovirus group, Avihepadnavirus, Avipoxvirus, B virus, B19 virus, Babanki virus, baboon herpesvirus, baculovirus, Barmah Forest virus, Bebaru virus, Berrimah virus, Betaretrovirus, Birnavirus, Bittner virus, BK virus, Black Creek Canal virus, bluetongue virus, Bolivian hemorrhagic fever virus, Borna disease virus, border disease of sheep virus, borna virus, bovine alphaherpesvirus 1, bovine alphaherpesvirus 2, bovine coronavirus, bovine ephemeral fever virus, bovine immunodeficiency virus, bovine leukemia virus, bovine leukosis virus, bovine mammillitis virus, bovine papillomavirus, bovine papular stomatitis virus, bovine parvovirus, bovine syncytial virus, bovine type C oncovirus, bovine viral diarrhea virus, Buggy Creek virus, bullet shaped virus group, Bunyamwera virus supergroup, Bunyavirus, Burkitt's lymphoma virus, Bwamba Fever, CA virus, Calicivirus, California encephalitis virus, camelpox virus, canarypox virus, canid herpesvirus, canine coronavirus, canine distemper virus, canine herpesvirus, canine minute virus, canine parvovirus, Cano Delgadito virus, caprine arthritis virus, caprine encephalitis virus, Caprine Herpes Virus, Capripox virus, Cardiovirus, caviid herpesvirus 1, Cercopithecid herpesvirus 1, cercopithecine herpesvirus 1, Cercopithecine herpesvirus 2, Chandipura virus, Changuinola virus, channel catfish virus, Charleville virus, chickenpox virus, Chikungunya virus, chimpanzee herpesvirus, chub reovirus, chum salmon virus, Cocal virus, Coho salmon reovirus, coital exanthema virus, Colorado tick fever virus, Coltivirus, Columbia SK virus, common cold virus, contagious ecthyma virus, contagious pustular dermatitis virus, Coronavirus, Corriparta virus, coryza virus, cowpox virus, coxsackie virus, CPV (cytoplasmic polyhedrosis virus), cricket paralysis virus, Crimean-Congo hemorrhagic fever virus, croup associated virus, Cryptovirus, Cypovirus, Cytomegalovirus, cytomegalovirus group, cytoplasmic polyhedrosis virus, deer papillomavirus, deltaretrovirus, dengue virus, Densovirus, Dependovirus, Dhori virus, diploma virus, *Drosophila* C virus, duck hepatitis B virus, duck hepatitis virus 1, duck hepatitis virus 2, duovirus, Duvenhage virus, Deformed wing virus DWV, eastern equine encephalitis virus, eastern equine encephalomyelitis virus, EB virus, Ebola virus, Ebola-like virus, echo virus, echovirus, echovirus 10, echovirus 28, echovirus 9, ectromelia virus, EEE virus, EIA virus, EIA virus, encephalitis virus, encephalomyocarditis group virus, encephalomyocarditis virus, Enterovirus, enzyme elevating virus, enzyme elevating virus (LDH), epidemic hemorrhagic fever virus, epizootic hemorrhagic disease virus, Epstein-Barr virus, equid alphaherpesvirus 1, equid alphaherpesvirus 4, equid herpesvirus 2, equine abortion virus, equine arteritis virus, equine encephalosis virus, equine infectious anemia virus, equine morbillivirus, equine rhinopneumonitis virus, equine rhinovirus, Eubenangu virus, European elk papillomavirus, European swine fever virus, Everglades virus, Eyach virus, felid herpesvirus 1, feline calicivirus, feline fibrosarcoma virus, feline herpesvirus, feline immunodeficiency virus, feline infectious peritonitis virus, feline leukemia/sarcoma virus, feline leukemia virus, feline panleukopenia virus, feline parvovirus, feline sarcoma virus, feline syncytial virus, Filovirus, Flanders virus, Flavivirus, foot and mouth disease virus, Fort Morgan virus, Four Corners hantavirus, fowl adenovirus 1, fowlpox virus, Friend virus, Gammaretrovirus, GB hepatitis virus, GB virus, German measles virus, Getah virus, gibbon ape leukemia virus, glandular fever virus, goatpox virus, golden shinner virus, Gonometa virus, goose parvovirus, granulosis virus, Gross' virus, ground squirrel hepatitis B virus, group A arbovirus, Guanarito virus, guinea pig cytomegalovirus, guinea pig type C virus, Hantaan virus, Hantavirus, hard clam reovirus, hare fibroma virus, HCMV (human cytomegalovirus), hemadsorption virus 2, hemagglutinating virus of Japan, hemorrhagic fever virus, hendra virus, Henipaviruses, Hepadnavirus, hepatitis A virus, hepatitis B virus group, hepatitis C virus, hepatitis D virus, hepatitis delta virus, hepatitis E virus, hepatitis F virus, hepatitis G virus, hepatitis nonA nonB virus, hepatitis virus, hepatitis virus (nonhuman), hepatoencephalomyelitis reovirus 3, Hepatovirus, heron hepatitis B virus, herpes B virus, herpes simplex virus, herpes simplex virus 1, herpes simplex virus 2, herpesvirus, herpesvirus 7, Herpesvirus ateles, Herpesvirus *hominis*, Herpesvirus infection, Herpesvirus saimiri, Herpesvirus suis, Herpesvirus varicellae, Highlands J virus, Hirame rhabdovirus, hog cholera virus, human adenovirus 2, human alphaherpesvirus 1, human alphaherpesvirus 2, human alphaherpesvirus 3, human B lymphotropic virus, human betaherpesvirus 5, human coronavirus, human cytomegalovirus group, human foamy virus, human gammaherpesvirus 4, human gammaherpesvirus 6, human hepatitis A virus, human herpesvirus 1 group, human herpesvirus 2 group, human herpesvirus 3 group, human herpesvirus 4 group, human herpesvirus 6, human herpesvirus 8, human immunodeficiency virus, human immunodeficiency virus 1, human immunodeficiency virus 2, human papillomavirus, human T cell leukemia virus, human T cell leukemia virus I, human T cell leukemia virus II, human T cell leukemia virus III, human T cell lymphoma virus I, human T cell lymphoma virus II, human T cell lymphotropic virus type 1, human T cell lymphotropic virus type 2, human T lymphotropic virus I, human T lymphotropic virus II, human T lymphotropic virus III, Ichnovirus, infantile gastroenteritis virus, infectious bovine rhinotracheitis virus, infectious haematopoietic necrosis virus, infectious pancreatic necrosis virus, influenza virus A, influenza virus B, influenza virus C, influenza virus D, influenza virus pr8, insect iridescent virus, insect virus, iridovirus, Japanese B virus, Japanese encephalitis virus, JC virus, Junin virus, Kaposi's sarcoma-associated herpesvirus, Kemerovo virus, Kilham's rat virus, Klamath virus, Kolongo virus, Korean hemorrhagic fever virus, kumba virus, Kysanur forest disease virus, Kyzylagach virus, La Crosse virus, lactic dehydrogenase elevating virus, lactic dehydrogenase virus, Lagos bat virus, Langur virus, lapine parvovirus, Lassa fever virus, Lassa virus, latent rat virus, LCM virus, Leaky virus, Lentivirus, Leporipoxvirus, leukemia virus, leukovirus, lumpy skin disease virus, lymphadenopathy associated virus, Lymphocryptovirus, lymphocytic choriomeningitis virus, lymphoproliferative virus group, Machupo virus, mad itch virus, mammalian type B oncovirus group, mammalian type B retroviruses, mammalian type C retrovirus group, mammalian type D retroviruses, mammary tumor virus, Mapuera virus, Marburg virus, Marburg-like virus, Mason Pfizer monkey virus, Mastadenovirus, Mayaro virus, ME virus, measles virus, Menangle virus, Mengo virus, Mengovirus, Middelburg virus, milkers nodule virus, mink enteritis virus, minute virus of mice, MLV related virus, MM virus, Mokola virus, Molluscipoxvirus, Molluscum contagiosum virus, monkey B virus, monkeypox virus, Mononegavirales, Morbillivirus, Mount Elgon bat virus, mouse cytomegalovirus, mouse encephalomyelitis virus, mouse hepatitis virus, mouse K virus, mouse leukemia virus, mouse mammary tumor virus, mouse minute virus, mouse pneumonia virus, mouse poliomyelitis virus, mouse polyomavirus, mouse sarcoma virus, mousepox virus, Mozambique virus, Mucambo virus, mucosal disease virus, mumps virus, murid betaherpesvirus 1, murid cytomegalovirus 2, murine cytomegalovirus group, murine encephalomyelitis virus, murine hepatitis virus, murine leukemia virus, murine nodule inducing virus, murine polyomavirus, murine sarcoma virus, Muromegalovirus, Murray Valley encephalitis virus, myxoma virus, Myxovirus, Myxovirus multiforme, Myxovirus parotitidis, Nairobi sheep disease virus, Nairovirus, Nanirnavirus, Nariva virus, Ndumo virus, Neethling virus, Nelson Bay virus, neurotropic virus, New World Arenavirus, newborn pneumonitis virus, Newcastle disease virus, Nipah virus, noncytopathogenic virus, Norwalk virus, nuclear polyhedrosis virus (NPV), nipple neck virus, O'nyong'nyong virus, Ockelbo virus, oncogenic virus, oncogenic viruslike particle, oncornavirus, Orbivirus, Orf virus, Oropouche virus, Orthohepadnavirus, Orthomyxovirus, Orthopoxvirus, Orthoreovirus, Orungo, ovine papillomavirus, ovine catarrhal fever virus, owl monkey herpesvirus, Palyam virus, Papillomavirus, Papillomavirus sylvilagi, Papovavirus, parainfluenza virus, parainfluenza virus type 1, parainfluenza virus type 2, parainfluenza virus type 3, parainfluenza virus type 4, Paramyxovirus, Parapoxvirus, paravaccinia virus, Parvovirus, Parvovirus B19, parvovirus group, Pestivirus, Phlebovirus, phocine distemper virus, Picodnavirus, Picornavirus, pig cytomegalovirus-pigeonpox virus, Piry virus, Pixuna virus, pneumonia virus of mice, Pneumovirus, poliomyelitis virus, poliovirus, Polydnavirus, polyhedral virus, polyoma virus, Polyomavirus, Polyomavirus *bovis*, Polyomavirus *cercopitheci*, Polyomavirus *hominis* 2, Polyomavirus *maccacae* 1, Polyomavirus *muris* 1, Polyomavirus *muris* 2, Polyomavirus *papionis* 1, Polyomavirus *papionis* 2, Polyomavirus *sylvilagi*, Pongine herpesvirus 1, porcine epidemic diarrhea virus, porcine hemagglutinating encephalomyelitis virus, porcine parvovirus, porcine transmissible gastroenteritis virus, porcine type C virus, pox virus, poxvirus, poxvirus variolae, Prospect Hill virus, Provirus, pseudocowpox virus, pseudorabies virus, psittacinepox virus, quailpox virus, rabbit fibroma virus, rabbit kidney vaculolating virus, rabbit papillomavirus, rabies virus, raccoon parvovirus, raccoonpox virus, Ranikhet virus, rat cytomegalovirus, rat parvovirus, rat virus, Rauscher's virus, recombinant vaccinia virus, recombinant virus, reovirus, reovirus 1, reovirus 2, reovirus 3, reptilian type C virus, respiratory infection virus, respiratory syncytial virus, respiratory virus, reticuloendotheliosis virus, Rhabdovirus, Rhabdovirus carpia, Rhadinovirus, Rhinovirus, Rhizidiovirus, Rift Valley fever virus, Riley's virus, rinderpest virus, RNA tumor virus, Ross River virus, Rotavirus, rougeole virus, Rous sarcoma virus, rubella virus, rubeola virus, Rubivirus, Russian autumn encephalitis virus, SA 11 simian virus, SA2 virus, Sabia virus, Sagiyama virus, Saimirine herpesvirus 1, salivary gland virus, sandfly fever virus group, Sandjimba virus, SARS virus, SDAV (sialodacryoadenitis virus), sealpox virus, Semliki Forest Virus, Seoul virus, sheeppox virus, Shope fibroma virus, Shope papilloma virus, simian foamy virus, simian hepatitis A virus, simian human immunodeficiency virus, simian immunodeficiency virus, simian parainfluenza virus, simian T cell lymphotrophic virus, simian virus, simian virus 40, Simplexvirus, Sin Nombre virus, Sindbis virus, smallpox virus, South American hemorrhagic fever viruses, sparrowpox virus, Spumavirus, squirrel fibroma virus, squirrel monkey retrovirus, SSV 1 virus group, STLV (simian T lymphotropic virus) type I, STLV (simian T lymphotropic virus) type II, STLV (simian T lymphotropic virus) type III, stomatitis papulosa virus, submaxillary virus, suid alphaherpesvirus 1, suid herpesvirus 2, Suipoxvirus, swamp fever virus, swinepox virus, Swiss mouse leukemia virus, TAC virus, Tacaribe complex virus, Tacaribe virus, Tanapox virus, Taterapox virus, Tench reovirus, Theiler's encephalomyelitis virus, Theiler's virus, Thogoto virus, Thottapalayam virus, Tick borne encephalitis virus, Tioman virus, Togavirus, Torovirus, tumor virus, Tupaia virus, turkey rhinotracheitis virus, turkeypox virus, type C retroviruses, type D oncovirus, type D retrovirus group, ulcerative disease rhabdovirus, Una virus, Uukuniemi virus group, vaccinia virus, vacuolating virus, varicella zoster virus, Varicellovirus, Varicola virus, variola major virus, variola virus, Vasin Gishu disease virus, VEE virus, Venezuelan equine encephalitis virus, Venezuelan equine encephalomyelitis virus, Venezuelan hemorrhagic fever virus, vesicular stomatitis virus, Vesiculovirus, Vilyuisk virus, viper retrovirus, viral haemorrhagic septicemia virus, Visna Maedi virus, Visna virus, volepox virus, VSV (vesicular stomatitis virus), Wallal virus, Warrego virus, wart virus, WEE virus, West Nile virus, western equine encephalitis virus, western equine encephalomyelitis virus, Whataroa virus, Winter Vomiting Virus, woodchuck hepatitis B virus, woolly monkey sarcoma virus, wound tumor virus, WRSV virus, Yaba monkey tumor virus, Yaba virus, Yatapoxvirus, yellow fever virus, and the Yug Bogdanovac virus.

Types of virus infections and related disorders that can be treated include, for example, infections due to the herpes family of viruses such as EBV, CMV, HSV I, HSV II, VZV and Kaposi's-associated human herpes virus (type 8), human T cell or B cell leukemia and lymphoma viruses, adenovirus infections, hepatitis virus infections, pox virus infections, papilloma virus infections, polyoma virus infections, infections due to retroviruses such as the HTLV and HIV viruses, and infections that lead to cellular disorders resulting from and/or associated with viral infection such as, for example, Burkitt's lymphoma, EBV-induced malignancies, T and B cell lymhoproliferative disorders and leukemias, and other viral-induced malignancies. Other neoplasias that can be treated include virus-induced tumors, malignancies, cancers, or diseases that result in a relatively autonomous growth of cells. Neoplastic disorders include leukemias, lymphomas, sarcomas, carcinomas such as a squamous cell carcinoma, a neural cell tumor, seminomas, melanomas, germ cell tumors, undifferentiated tumors, neuroblastomas (which are also considered carcinomas by some), mixed cell tumors, or other malignancies. Neoplastic disorders prophylactically or therapeutically treatable with compositions of the invention include small cell lung cancers and other lung cancers, rhabdomyosarcomas, chorio carcinomas, glioblastoma multiformas (brain tumors), bowel and gastric carcinomas, leukemias, ovarian cancers, prostate cancers, osteosarcomas, or cancers that have metastasized. Diseases of the immune system that are treatable include Hodgkins' disease, the non-Hodgkin's lymphomas including the follicular and nodular lymphomas, adult T and B cell and NK lymphoproliferative disorders such as leukemias and lymphomas (benign and malignant), hairy-cell leukemia, hairy leukoplakia, acute myelogenous, lymphoblastic or other leukemias, chronic myelogenous leukemia, and myelodysplastic syndromes. Additional diseases that can be treated or prevented include breast cell carcinomas, melanomas and hematologic melanomas, ovarian cancers, pancreatic cancers, liver cancers, stomach cancers, colon cancers, bone cancers, squamous cell carcinomas, neurofibromas, testicular cell carcinomas, kidney and bladder cancers, cancer and benign tumors of the nervous system, and adenocarcinomas.

An embodiment of the invention is directed to methods for the treatment of a patient with a viral infection or a virus-associated neoplastic disorder comprising the administration of an inducing agent and an anti-viral agent according to a method of the invention. Treatable infectious diseases include viral infections caused by, without limitation, a hepatitis virus, a retrovirus such as HIV or HTLV, an influenza virus, a papilloma virus, a herpes virus (HSV I, HSV II, EBV), a polyoma virus, paramyxovirus, or corona virus, or a "slow viral disease" such as disease caused by lentiviruses, measles virus (subacute sclerosing panencephalitis), and transmissible spongiform encephalopathies.

Viruses may exist in infected cells as autonomous particles or be integrated, as, for example, in latent infections. Latent infections may be periodic, such as HSV-I and II or be continuously productive of virus or virus products, though at fairly low levels. Infections may also be lytic, with infectious particles secreted or otherwise extruded or expelled (virus burst) from cells. Infections may also be of parts of a virus such as, for example, by viral genes or by defective-interfering particles that are incapable of productive replication on their own, but may be capable of causing disease.

Cells that can be treated include any cell that becomes infected with a virus or a part of a virus and, preferably, infected by integration. Such cells include cells of the hematopoietic system, such as lymphocytes, erythrocytes and mylocytes, neural cells, and neural-supporting cells, cells of the digestive system, cells of the epithelial system. Cells that contain integrated viral genomes or only parts of viral genomes may also be effectively treated.

Anti-neoplastic activity includes cytotoxic (tumor cell death) activity, but also includes, for example, the ability to induce the differentiation of transformed cells including cells that comprise neoplasm due to infection (e.g. viral infections such as a human papilloma virus, herpes viruses including Herpes Simplex virus type I or II or Epstein-Barr virus, a hepatitis virus, a human T cell leukemia virus (HTLV) or another retrovirus), and other malignancies. Upon differentiation, these cells lose their aggressive nature, no longer metastasize, are no longer proliferating, and eventually die and/or are removed by the T cells, natural killer cells, and macrophages of the patient's immune system.

The process of cellular differentiation is stimulated or turned on by, for example, the stimulation and/or inhibition of gene specific transcription. Certain gene products are directly involved in cellular differentiation and can transform an actively dividing cell into a cell that has lost or has a decreased ability to proliferate. An associated change of the pattern of cellular gene expression can be observed. To control this process includes the ability to reverse a malignancy. Genes whose transcriptional regulation are altered in the presence of compositions described herein include the oncogenes myc, ras, myb, jun, fos, abl, and src. The activities of these gene products, as well as the activities of other oncogenes, are described in Slamon, J. D., et al. 1984 *Science* 224:256-62. Another example of anti-neoplastic activity includes the ability to regulate the life cycle of the cell, the ability to repress angiogenesis or tissue regeneration through the blockade or suppression of factor activity, production or release, the ability to regulate transcription or translation, or the ability to modulate transcription of genes under angiogenesis, growth factor or hormonal control.

Additional anti-neoplastic activities include the ability to regulate the cell cycle, for example, by affecting time in and passage through S phase, M phase, $G_1$ phase or $G_0$ phase, the ability to increase intracellular cAMP levels, the ability to inhibit or stimulate histone acetylation, the ability to methylate nucleic acids, and the ability to maintain or increase intracellular concentrations of anti-neoplastic agents. The neoplastic disorder may be any disease or malady that could be characterized as a neoplasm, a tumor, a malignancy, a cancer, or a disease that results in a relatively autonomous growth of cells. Neoplastic disorders prophylactically or therapeutically treatable via the methods of the invention include small cell lung cancers and other lung cancers, rhabdomyosarcomas, choriocarcinomas, glioblastoma multiformas (brain tumors), bowel and gastric carcinomas, leukemias, ovarian cancers, prostate cancers, osteosarcomas, or cancers that have metastasized. Diseases of the immune system that are treatable carrying out the methods of the invention include Hodgkins' lymphomas and the non-Hodgkin's lymphomas including the follicular lymphomas, nodular lymphomas, T- and NK-lymphomas, Burkitt's lymphoma, adult T-cell leukemias and lymphomas, hairy-cell leukemia, acute myelogenous, lymphoblastic, or other leukemias, chronic myelogenous leukemia, and myelodysplastic syndromes. Additional diseases treatable by the compositions include virally-induced cancers wherein the viral agent is EBV, HPV, HIV, CMV, HTLV-1 or HBV, breast cell carcinomas, melanomas and hematologic melanomas, ovarian cancers, pancreatic cancers, liver cancers, stomach cancers, colon cancers, bone cancers, squamous cell carcinomas, neurofibromas, testicular cell carcinomas, kidney and bladder cancers, tumors of the nervous system, and adenocarcinomas.

C. Inducing Agents

Inducing agents administered according to methods of the invention include, without limitation, short-chain fatty acid (SCFA) derivatives, histone deacetylase (HDAC) inhibitors, phorbol esters, and cytokines. Thus, inducing agents administered according to methods of the invention include SCFA derivatives, for example, without limitation, chemicals of the structure $R_1$-$R_2$-$R_3$ or, preferably, $R_1$—C(O)—$R_2$-$R_3$ wherein $R_1$ is $CH_x$, $H_x$, $NH_x$, $OH_x$, $SH_x$, $COH_x$, $CONH_x$, COOH or $COSH_x$; $R_2$ is $CH_x$ or a branched or linear alkyl chain; $R_3$ is $CONH_x$, $COSH_x$, COOH, $COOR_4$, $COR_4$ or $OR_4$; $R_4$ is $CH_x$, $H_x$, $NH_x$, $OH_x$, $SH_x$ or a branched or linear alkyl chain; phenyl-$R_5$-$R_6$-$R_7$, wherein phenyl is a six carbon benzyl ring or a hydrogenated, hydroxylated or halogenated six carbon ring; $R_5$ is $CH_x$, $NH_x$, $OH_x$, or $SH_x$; $R_6$ is $CH_x$, $NH_x$, $OH_x$, $SH_x$ or a branched or linear alkyl chain; $R_7$ is $CH_x$, $H_x$, $NH_x$, $OH_x$, $SH_x$, $CONH_x$, COOH, $COSH_x$, $COOR_8$, $COR_8$ or $OR_8$; $R_8$ is $CH_x$, $H_x$, $NH_x$, $OH_x$, $SH_x$ or a branched or linear alkyl chain; and phenyl-$R_9$-$R_{10}$ wherein $R_9$, is $CH_x$, $NH_x$, $OH_x$, $SH_x$ or a branched or linear alkyl chain; $R_{10}$ is $CH_x$, $H_x$, $NH_x$, $OH_x$, $SH_x$, $CONH_x$, COOH, $COSH_x$, $COOR_{11}$, $CUR_{11}$ or $OR_{11}$; and $R_{11}$ is $CR_x$, $H_x$, $NH_x$, $OH_x$, $SH_x$ or a branched or linear alkyl chain; wherein x is 0, 1, 2 or 3. Preferably, $R_4$ comprises between 1 to 8 carbon atoms and more preferably 1, 2, 3 or 4 carbon atoms. Preferably, $R_6$ comprises between 1 to 8 carbon atoms and more preferably 1, 2, 3 or 4 carbon atoms. Preferably, $R_8$ comprises between 1 to 8 carbon atoms and more preferably 1, 2, 3 or 4 carbon atoms.

Examples of chemical compounds of the structure $R_1$-$R_2$-$R_3$ or $R_1$—C(O)—$R_2$-$R_3$ include acids, amines, monoamides and diamides of butyric acid ($H_3C$—$CH_2$—$CH_2$—COOH), butyric acid ethyl ester ($CH_3CH_2CH_2COCH_2CH_3$), 4,4,4-trifluorobutyric acid ($CF_3CH_2CH_2COOH$), 2,2-diethyl butyric acid, 3,3-dimethyl butyric acid ($C_6H_{12}O_2$), 3,3-diethyl butyric acid, fumaric acid (HOOCCH=CHCOOH), fumaric acid monomethyl and monoethyl ester, fumaric acid monoamide ($C_4H_5O_2N$), fumaramide ($H_2NCOCHCHCONH_2$), succinic acid ($HOOCCH_2CH_2COOH$) (succinamic acid and succinamide), 2,3-dimethyl succinic acid and methoxy acetic acid ($CH_3CH_2OCH_3$).

Examples of chemical compounds of the structure phenyl-$R_5$-$R_6$-$R_7$ include acids, amines and amides of phenoxyacetic acid ($C_6H_5OCH_2COOH$; $C_6H_5OCH_2COONH_3$), 2- and 3-thiophenoxy propionic acid ($C_6H_5SCH(CH_3)COOH$; $C_6H_5SCH_2CH_2COOH$), 2- and 3-phenoxy propionic acid ($C_6H_5OCH(CH_3)COOH$; $C_6H_5OCH_2CH_2COOH$), 2- and 3-phenyl propionic acid ($C_6H_5CH(CH_3)COOH$; $C_6H_5CH_2CH_2COOH$), 4-chlorophenoxy-2-propionic acid ($ClC_6OCH_2CH_2CO_2H$), methoxy acetic acid ($H_3COCH_2CO_2H$), and 2-thiophenoxy acetic acid ($C_6H_5SCH_2COOH$).

Examples of chemical compounds of the structure phenyl-$R_9$-$R_{10}$ include acids, amines and amides of cinnamic acid ($C_6H_5CH$=CHCOOH), hydrocinnamic acid, dihydro cinnamic acid ($C_6H_5CH_2CH_2COOH$), a-methyl hydrocinnamic acid or dihydrocinnamic acid, 2,3-dimethyl hydrocinnamic or dihydrocinnamic acid, phenyl acetate ethyl ester ($C_6H_5CH(CH_3)CH_2COCH_2CH_3$), 2-phenoxypropionic acid ($C_6H_5OCH_2CO_2H$), phenoxy acetic acid ($CH_3CH(OC_6H_5)CO_2H$), and 3-phenyl butyric acid ($C_6H_5CH(CH_3)CH_2COOH$). Additional chemical compounds which may or may not be included in the above classification scheme include monobutyrin, tributyrin ($CH_2(OCOCH_2CH_2CH_3)CH(OCOCH_2CH_2CH_3)CH_2(OCOCH_2CH_2CH_3)$), ethyl-phenyl acetic acid ($CH_3CH_2C_6H_5CH_2COOH$), indol-3-propionic acid, indol-3-butyric acid, 1- and 2-methyl cyclopropane carboxylic acid ($C_5H_8O_2$ and $C_6H_8O_2$), mercaptoacetic acid ($C_2H_4O_2S$), N-acetylglycine ($C_4H_7O_3N$), squaric acid ($C_4H_2O_4$), 4-trifluorobutanol ($C_4H_7OF_3$), chloropropionic acid ($C_1CH_2CH_2CO_2H$), 3-trimethyl silyl-1-proposulfonic acid sodium ($C_6H_{15}O_3SS$), 2-oxopantansane ($C_5H_8O_3$), isobutyl hydroxylamine HCl ($C_4H_{12}OCl$), 2-methyl butanoic acid ($C_5H_{10}O_2$), o-benzoyl lactate, n-dimethylbutyric acid glycine amide, o-dimethyl butyric acid lactate, and diethyl butyric acid.

Inducing agents useful in pharmaceutical compositions for the treatment of virus-associated disorders include, without limitation, propionic acid, butyric acid, succinic acid, fumaric acid monoethyl ester, trifluorobutanol ($C_4H_7OF_3$), chloropropionic acid ($C_1CH_2CH_2COOH$), isopropionic acid, 2-oxypentasane ($CH_3CH_2CH_2C(O)COOH$), 2,2- or 3,3-dimethyl butyric acid ($C_6H_{12}O_2$), 2,2- or 3,3-diethyl butyric acid ($C_8H_{16}O_2$), butyric acid ethyl ester, 2-methyl butanoic acid ($C_5H_{10}O_2$), fumaric acid ($C_4H_4O_3$) and amides and salts thereof. Other examples include methoxy acetic acid ($H_3C(O)CH_2COOH$), methoxy propionic acid, N-acetylglycine ($H_3CC(O)NCH_2COOH$), mercaptoacetic acid ($HSCH_2COOH$), 1- or 2-methyl cyclopropane carboxylic acid ($C_5H_8O_2$), squaric acid ($C_4H_2O_4$), 2- or 3-phenoxy propionic acid, methoxy butyric acid, phenoxy acetic acid, 4-chloro-2-phenoxy 2-propionic acid, 2- or 3-phenoxy butyric acid, phenyl acetic acid, phenyl propionic acid, 3-phenyl butyric acid, ethyl-phenyl acetic acid, 4-chloro-2-phenoxy-2-propionic acid, n-dimethyl butyric acid glycine amide, o-benzoyl lactic acid, o-dimethyl butyric acid lactate, cinnamic acid, dihydrocinnamic acid ($C_6H_5CHCH_3COOH$), α-methyl-dihydrocinnamic acid, thiophenoxy acetic acid, and amines, amides and salts of these chemicals.

Inducing agents include retinoic acid, retinol, cytosine arabinoside, phorbols such as the phorbol diester 12-0-tetradecanoylphorbol 13-acetate (TPA), teleocidine B, indole alkaloids, cytotoxin, plant lectins from *Streptomyces*, glucocorticoids such as estrogen and progesterone, phytohemagglutinin (PHA), bryostatin, growth factors (e.g. PDGF, VEGF, EGF, FGF, NGF, TGF, BCGF), anti-sense nucleic acids (e.g. DNA, RNA or PNA), aptamers (nucleic acid oligonucleotides with secondary or tertiary structures which bind with high affinity and selectivity to a target molecule), erythropoietin (EPO), the interleukins (IL-1, IL-2, IL-3, etc.), cAMP and cAMP analogs such as dibutyrl cAMP, activin, inhibin, steel factor, interferon, the bone morphogenic proteins (BMBs), hydroxyurea and dimethyl sulfoxide (DMSO). Other inducing agents include interferons (e.g. α-, β-, γ-interferon), cytokines such as tumor necrosis factor (TNF), cell receptors, and growth factor antagonists, which may be purified or recombinantly produced.

Inducing agents administered according to the methods of the invention include histone deacetylase (HDAC) inhibitors (including those of the hydroxamic acid class and the benzamide class), DNA methyltransferase inhibitors, and proteasome inhibitors. HDAC inhibitors, a class of compounds that interfere with the function of histone deacetylase, include, without limitation, short-chain fatty acids (butyrate, phenylbutyrate, valproate, AN-9, etc., as described above), hydroxamic acids (for example m-carboxycinnamic acid, bishydroxamic acid, suberic bishydroxamic acid, Trichostatin A (7-[4-(dimethylamino)phenyl]-N-hydroxy-4,6-dimethyl-7-oxohepta-2,4-dienamide), SAHA (suberoyl anilide hydroxamic acid)/Vorinostat, oxamflatin, ABHA, SB-55629, pyroxamide, propenamides, aroyl pyrrolyl hydroxamides, Belinostat/PXD101, Papobinostat, LAQ824 (((E)-N-hydroxy-3-[4-[[2-hydroxyethyl-[2-(1H-indol-3-yl)ethyl]amino]methyl]phenyl]prop-2-enamide), LBH589, TSA), Pivanex, spiruchostatins, cyclic tetrapeptides (for example, trapoxin A (cyclo((S)-phenylalanyl-(S)-phenylalanyl-(R)-pipecolinyl-(2S,9S)-2-amino-8-oxo-9,10-epoxydecanoyl),), trapoxin B (cyclo((S)-phenylalanyl-phenylalanyl-(R)-prolyl-2-amino-8-oxo-9,10-epoxydecanoyl)), HC-toxin, chlamydocin, diheteropeptin, WF-3161, Cy1-1, Cy1-2, azumamide A), cyclic peptides (for example, FK-228, FR901228), depsipeptides (for example, romidepsin, FK228 ((E)-(1S,4S,10S,21R)-7[(Z)-ethylideno]-4,21-diisopropyl-2-oxa-12,13-dithia-5,8,20,23-tetrazabicyclo[8,7,6]-tricos-16-ene-3,6,9,22-pentanone), FK228 analogs and derivatives, largazole, largazole analogs and derivatives), peptide antibiotics (apicidin), benzamides (MS275 (3-pyridinylmethyl [[4-[[(2-aminophenyl)amino]carbonyl]phenyl]methyl] carbamate, N-(2-Aminophenyl)-4-[N-(pyridine-3ylmethoxycarbonyl)aminomethyl]benzamide), CI994 (4-(Acetylamino)-N-(2-aminophenyl) benzamide), MGCD0103), electrophilic ketones (TPX, AOR, Depudecin), aliphatic acid compounds (for example, butyrate, phenylbutyrate, valproic acid), FR901375, nicotinamide, NAD derivatives, Sirtinol, splitomycin, dihydrocoumarin, naphthopyranone, 2-hydroxynaphthaldehydes, PCYC-0402, PCYC-0403, PCI-24781 (3-(dimethylaminomethyl)-N-[2-[4-(hydroxycarbamoyl)phenoxy]ethyl]-1-benzofuran-2-carboxamide), depudecin, tubacin, organosulfur compounds, and dimethyl sulfoxide (DMSO). Other compounds whch may also be administered as inducing agents, which include CHAPs, Scriptaid, Tubacin, JNJ16241199, A-161906, 6-(3-Chlorophenylureido)caproic hydroxamic acid, SB939, ITF2357 ({6-[(diethylamino) methyl]-2-naphthyl}methyl {4-[(hydroxyamino)carbonyl] phenyl}carbamate), 4SC-201, AR-42, OPB-801, RG2833, CUDC-101, JNJ-26481585 (C21H26N6O2), MK0683 (suberoylanilide hydroxamic acid), M344 (4-(Diethylamino)-N-[7-(hydroxyamino)-7-oxoheptyl]benzamide), BML-201 (N-(2-aminophenyl)-N'-phenyl-octanediamide), Droxinostat, and pivaloyloxymethyl butyrate.

Useful amines and amides include isobutylhydroxylamine: $HCl(C_4H_{12}OCl)$, fumaric acid monoamide ($C_4H_5O_2N$), fumaramide ($H_2NCOCHCHCONH_2$), succinamide and isobutyramide ($C_4H_9ON$). Salts can be sodium, potassium, calcium, ammonium, lithium or choline such as sodium 3-trimethyl silyl-1-proposulfonic acid ($C_6H_{15}O_3SiS:Na$). Reagents which may be electrostatically or covalently bonded with the inducing agent include amino acids such as arginine (arginine butyrate), glycine, alanine, asparagine, glutamine, histidine or lysine, nucleic acids including nucleosides or nucleotides, or substituents such as carbohydrates, saccharides, lipids, fatty acids, proteins or protein fragments. Combinations of these salts with the inducing agent can also produce useful new compounds from the interaction of the combination.

In one embodiment of a method according to the invention, the inducing agent is butyric acid in the form of arginine butyrate, and the antiviral agent is a nucleoside analog. Butyric acid is one of many naturally-occurring short-chain fatty acids that are generated in the small and large bowel by metabolism of carbohydrates. Butyrate is a four-carbon fatty acid with weakly acidic properties and is rapidly absorbed and metabolized. Butyrates have shown significant anti-tumor effects. Sodium butyrate (NAB) has been used clinically in patients with acute myelogenous leukemias and there has now been extensive experience with arginine butyrate, a salt of butyrate, in clinical studies for the treatment of J3-hemoglobinopathies, and more recently with refractory solid neoplasms (Foss, F. M., et al. 1994 *Proc. ASCO* 13:162; Sanders, D. A., et al. 1995 *Proc. ASCO*).

Butyrate and derivatives of butyrate including arginine butyrate have demonstrated several effects upon transformed cell lines in vitro that include decreased DNA replication leading to arrest of cell division in the $G_1$ phase, modification of cellular morphology, and alteration of gene expression consistent with differentiation of a given cell type examined (Klehr, D., et al. 1992 *Biochemistry* 31:3222-29). For example, human tumor cell lines as diverse as colon, breast, melanoma, hepatoma, squamous cell carcinoma of the cervix, endometrial, adenocarcinoma, teratocarcinoma cell lines, leukemic cells (HL-60), and normal human keratinocytes can all be induced to differentiate in the presence of butyrate concentrations ranging from 2-5 mM (Perrin, S. P., et al. 1987 *Biochem. Biophys. Res. Commun.* 148:694-700). The mechanism(s) of action proposed for these effects upon differentiation are varied and are not fully understood.

Chemical compounds are preferably optically pure with a specific conformation (plus {+} or minus {−}), absolute configuration (R or S), or relative configuration (D or L). Particular salts such as sodium, potassium, magnesium, calcium, choline, amino acid, ammonium or lithium, or combinations of salts may also be preferred, however, certain salts may be more advantageous than others. For example, chemical compounds that require high doses may introduce too much of a single salt to the patient. Sodium is generally an undesirable salt, because at high doses, sodium can increase fluid retention resulting in tissue destruction. In such instances, lower doses or combinations of different or alternative salts can be used. For example, compounds of the invention may be substituted with one or more halogens such as chlorine (Cl), fluorine (F), iodine (I), bromine (Br) or combinations of these halogens. As known to those of ordinary skill in the art, halogenation can increase the polarity, hydrophilicity, or lipophilicity of a chemical compound, which can be a desirable feature, for example, to transform a chemical compound into a composition that is more easily tolerated by the patient or more readily absorbed by the epithelial lining of the gastrointestinal tract. Such compositions could be orally administered to patients.

Therapeutically effective chemical compounds may be created by modifying any of the above chemical compounds so that after introduction into the patient, these compounds metabolize into active forms, such as the forms above, which have the desired effect on the patient. Compounds may also be created that are metabolized in a timed-release fashion allowing for a minimal number of introductions that are efficacious for longer periods of time. Combinations of chemical compounds can also produce useful new compounds from the interaction of the combination. Such compounds may also produce a synergistic effect when used in combination with other known or other compounds.

D. Antiviral Agents

Anti-viral agents that can be used in the compositions and methods of the provided invention can include, for example, substrates and substrate analogs, inhibitors and other agents that severely impair, debilitate or otherwise destroy virus-infected cells. Substrate analogs include amino acid and nucleoside analogs. Substrates can be conjugated with toxins or other viricidal substances. Inhibitors include integrase inhibitors, protease inhibitors, polymerase inhibitors and transcriptase inhibitors such as reverse transcriptase inhibitors.

Antiviral agents that can be used in the compositions and methods of the provided invention can include, for example, ganciclovir, valganciclovir, oseltamivir (Tamiflu), zanamivir (Relenza), abacavir, aciclovir, acyclovir, adefovir, amantadine, amprenavir, ampligen, arbidol, atazanavir, atripla, boceprevir, cidofovir, combivir, darunavir, delavirdine, didanosine, docosanol, edoxudine, efavirenz, emtricitabine, enfuvirtide, entecavir, famciclovir, fomivirsen, fosamprenavir, foscarnet, fosfonet, fusion inhibitors (e.g., enfuvirtide), ibacitabine, imunovir, idoxuridine, imiquimod, indinavir, inosine, integrase inhibitor, interferon type III, interferon type II, interferon type I, interferon, lamivudine, lopinavir, loviride, maraviroc, moroxydine, nelfinavir, nevirapine, nexavir, nucleoside analogues, peginterferon alfa-2a, penciclovir, peramivir, pleconaril, podophyllotoxin, protease inhibitor, raltegravir, reverse transcriptase inhibitor, ribavirin, rimantadine, ritonavir, pyrimidine antiviral, saquinavir, stavudine, synergistic enhancer (antiretroviral), tenofovir, tenofovir disoproxil, tipranavir, trifluridine, trizivir, tromantadine, truvada, valaciclovir (Valtrex), vicriviroc, vidarabine, viramidine, zalcitabine, and zidovudine.

Examples of nucleoside analogs include acyclovir (ACV), ganciclovir (GCV), famciclovir, foscarnet, ribavirin, zalcitabine (ddC), zidovudine (AZT), stavudine (D4T), lamivudine (3TC), didanosine (ddI), cytarabine, dideoxyadenosine, edoxudine, floxuridine, idozuridine, inosine pranobex, 2'-deoxy-5-(methylamino)uridine, trifluridine and vidarabine. Examples of a few protease inhibitors that show particular promise in human therapy include saquinivir, ritonavir and indinavir. Other anti-viral agents include interferons (e.g. α-, β-, γ-interferon), cytokines such as tumor necrosis factor (TNF), cell receptors and growth factor antagonists, which can be purified or recombinantly produced.

E. Induced Genes Including Viral-Associated Genes

Inducing agents (agents that induce expression) may act directly on the viral genome or indirectly through a cellular factor required for viral expression. For example, viral gene expression can be regulated through the regulation of the expression of viral transcription factors such as ZTA, RTA, tat, and tax, cellular transcription factors such as AP-1, AP-2, Sp1, NF-κB, and other transcriptional activators and/or repressors (factors), co-activators and co-repressors, histone acetylators and deacetylators, DNA methylases and demethylases, oncogenes or proto-oncogenes, or protein kinase C. These proteins act to regulate and thereby control expression of specific viral and/or other cellular genetic elements. According to the methods of the invention, control over their expression can lead to control over the infection. Other gene products, both viral and cellular in origin, whose expression can be regulated with inducing agents include proteases, polymerases, reverse transcriptases, cell-surface receptors, major histocompatibility antigens, growth factors, and combination of these products.

Additional genes whose expression or transcriptional regulation are altered in the presence of butyric acid include the oncogenes myc, ras, myb, abl and src. The activities of these gene products, as well as the activities of other oncogenes, are described in Slamon, J. D., et al. 1984 *Science* 224:256-62. Anti-proliferative activity also includes the ability to repress tumor angiogenesis through the blockade of angiogenesis factor activity, production or release, transcriptional regulation, or the ability to modulate transcription of genes under angiogenesis or growth factor or holinonal control. Either would be an effective therapy, particularly against both prostatic neoplasia and breast carcinomas. Further activities that effect transcription and/or cellular differentiation include increased intracellular cAMP levels, inhibition of histone acetylation, and inhibition of genomic methylation. Each of these activities is directly related to gene expression, and increased expression can sensitize infected cells to a specific anti-viral agent.

In some embodiments, inducing agents include arginine butyrate and/or other histone deacetylase inhibitors. Arginine butyrate induces EBV-TK activity in EBV-immortalized B-cells and patient-derived tumor cells. As latently-infected B-cells do not express TK, exposure of these cells to agents like arginine butyrate results in a modest induction of lytic replication and TK expression. TK expression can be used as a point for attack by anti-viral agents, allowing for treatment of latent infections.

Preliminary in vitro studies according to the invention demonstrate that induction of EBV-TK activity in EBV-immortalized B-cells and patient-derived tumor cells using these drugs is possible, and that these previously resistant cells are rendered susceptible to ganciclovir therapy. Treatment of patients with viral-associated tumors such as EBV with inducing agents such as arginine butyrate, to induce the expression of EBV-TK, and GCV, to eliminate EBV-TK expressing tumor cells, is an effective, non-toxic therapy. This therapeutic regimen does not depend on the associated viral genome being the cause of the tumor. Without wishing to be bound by theory, it is believed that just the presence of the EBV genome in latent form would make the tumor susceptible to this combination protocol.

Butyrate-associated induction of genes has been characterized for various cell types, and the genes are consistently in the class of differentiation markers of a cell. For example, in colon cancer cell lines, morphologic changes observed in the presence of butyrate correlate with increased expression of alkaline phosphatase, plasminogen activator, and CEA, all markers of differentiation. Hepatoma cell lines increase expression of alpha fetoprotein. Breast cancer cell lines express milk-related glycoproteins, epithelial membrane antigens, and increased lipid deposition. Sodium butyrate can also induce expression of cellular proteins associated with converting basal keratinacytes into committed epithelial cells.

Alteration of expression of certain transcription factors may affect regulation of gene expression and regulation of the cell cycle. In the breast cancer cell line MCF-7, butyrate induces a block in cellular proliferation that is associated with decreased expression of estrogen and prolactin hormone receptor mRNA expression, thus blocking the potential growth stimulation by estrogen and prolactin. These effects are associated with increased expression of the EGF receptor. Butyrate also has been shown to induce down-regulation of c-myc and p53 mRNA and to up-regulate expression of the c-fos transcription factor. In mouse fibroblasts, butyrate will block the cell cycle in the $G_1$ phase. When these cells are stimulated to proliferate with serum, TPA, or insulin, the immediate-early response transcription factors c-myc and c-jun are unregulated. However, the late $G_1$ phase downstream gene marker cdc-2 mRNA is not expressed, and cells are prevented from entering S phase.

The particular combination of inducing agent with anti-viral agent that is most effective against a specific disorder can be determined by one of ordinary skill in the art from empirical testing and, preferably, from a knowledge of each agent's mechanism of action. Three such examples are as follows. First, many of the RNA viruses such as HIV and other retroviruses require a reverse transcriptase to transcribe their genome into DNA. A few of the agents that induce expression or activity of retroviruses and their encoded genes, such as, for example, reverse transcriptase, are known to those of ordinary skill in the art. Anti-viral agents such as nucleoside analogs can be administered to the patient. Those substrate analogs will be specifically recognized by the reverse transcriptase that, when incorporated into the infected-cell genome, prevent viral replication and may also result in cell death. Second, many viruses require an active protease to assemble virus capsids to be packaged with viral genome. Protease inhibitors or proteases that alter cleavage patterns so that packaging cannot occur can be specifically targeted with an anti-viral agent that comprises an amino acid analog or toxic conjugate. Third, arginine butyrate and isobutyramide enhance expression of viral thymidine kinase and other viral protein kinases in EBV-infected lymphocytes. Ganciclovir or famcyclovir, in the presence of the viral thymidine kinase or other viral kinases, destroys the infected cell. Treatment of infected cells with both agents, according to the invention, will selectively destroy EBV virus-infected cells. In another aspect, of infected cells with both agents, according to the invention, will selectively disable or disrupt the viral activity within the cells in vivo.

F. Formulations, Routes of Administration, and Effective Doses

Administration of the compositions described herein may be by oral, parenteral, sublingual, rectal, or enteral administration, or pulmonary absorption or topical application. Compositions can be directly or indirectly administered to the patient. Indirect administration is performed, for example, by administering the composition to cells ex vivo and subsequently introducing the treated cells to the patient. The cells may be obtained from the patient to be treated or from a genetically related or unrelated patient. Related patients offer some advantage by lowering the immunogenic response to the cells to be introduced. For example, using techniques of antigen matching, immunologically compatible donors can be identified and utilized.

Both inducing and anti-viral agents can be purchased commercially and prepared as a mixed composition using techniques well-known to those of ordinary skill in the art.

Direct administration of a composition may be by oral, parenteral, sublingual, rectal such as suppository or enteral administration, or by pulmonary absorption or topical application. Parenteral administration may be by intravenous injection, subcutaneous injection, intramuscular injection, intra-arterial injection, intrathecal injection, intra-peritoneal injection, or direct injection or other administration to the site of the neoplasm. An infusion pump (to infuse, for example, the inducing agent into the subject's circulatory system during the first period of a cycle of therapy) is generally used intravenously, although subcutaneous, arterial, and epidural infusions are occasionally used. Injectable forms of administration are sometimes preferred for maximal effect. When long-term administration by injection is necessary, medi-ports, in-dwelling catheters, or automatic pumping mechanisms are also preferred, wherein direct and immediate access is provided to the arteries in and around the heart and other major organs and organ systems. The inducing agent and anti-viral agent may, in an embodiment of the invention, be administered through the same intravenous line.

An effective method of administration to a specific site may be by transdermal transfusion, such as with a transdermal patch, by direct contact to the cells or tissue, if accessible, such as a skin tumor, or by administration to an internal site through an incision or some other artificial opening into the body. Compositions may also be administered to the nasal passages as a spray. Diseases localized to the head and brain area are treatable in this fashion, as arteries of the nasal area provide a rapid and efficient access to the upper areas of the head. Sprays also provide immediate access to the pulmonary system and are the preferable methods for administering compositions to these areas.

Access to the gastrointestinal tract is gained using oral, enema, or injectable forms of administration. For example, administration of the anti-viral agent to the subject after the first period of a cycle of therapy (i.e., during the remainder of the cycle, during which only anti-viral agent without inducing agent is administered) is preferably oral. As a result, the subject can go through the reminder of the cycle of therapy at home. However, the patient may go through up to about ten, preferably less than or equal to six, cycles of therapy.

Administration of the anti-viral agent (amount and frequency) is well-known to or can be readily determined by the person of ordinary skill in the art.

As indicated above, orally active compositions are preferred for at least a portion of the cycle of therapy, as oral administration is usually the safest, most convenient, and economical mode of drug delivery. Oral administration can, however, be disadvantageous, because compositions are poorly absorbed through the gastrointestinal lining. Compounds that are poorly absorbed tend to be highly polar. Consequently, compounds that are effective, as described herein, may be made orally bioavailable by reducing or eliminating their polarity. This can often be accomplished by formulating a composition with a complimentary reagent that neutralizes its polarity, or by modifying the compound with a neutralizing chemical group. Oral bioavailability is also a problem, because drugs are exposed to the extremes of gastric pH and gastric enzymes. These problems can be overcome in a similar manner by modifying the molecular structure to be able to withstand very low pH conditions and resist the enzymes of the gastric mucosa such as by neutralizing an ionic group, by covalently bonding an ionic interaction, or by stabilizing or removing a disulfide bond or other relatively labile bond.

Compounds may also be used in combination with other agents to maximize the effect of the compositions administered in an additive or synergistic manner. Compositions may also comprise proteinaceous agents such as growth factors and/or cytokines, which are viral inducers. Such proteinaceous agents may also be aminated, glycosylated, acylated, neutralized, phosphorylated, or otherwise derivatized to form compositions that are more suitable for the method of administration to the patient or for increased stability during shipping or storage. Cytokines that may be effective in combination with the compositions described herein include growth factors such as B cell growth factor (BCGF), fibroblast-derived growth factor (FDGF), granulocyte/macrophage colony stimulating factor (GM-CSF), granulocyte colony stimulating factor (G-CSF), macrophage colony stimulating factor (M-CSF), epidermal growth factor (EGF), vascular endothelial growth factor (VEGF), platelet derived growth factor (PDGF) nerve growth factor (NGF), stem cell factor (SCF), and transforming growth factor (TGF). These growth factors plus a composition may further stimulate cellular differentiation and/or the expression of certain MHC antigens or tumor antigens. For example, BCGF plus a composition may be effective in treating certain B cell leukemias. NGF plus a composition may be useful in treating certain neuroblastomas and or nerve cell tumors. In a similar fashion, other agents such as differentiating agents may be useful in combination with a composition of the invention to prevent or treat a neoplastic disorder. Other differentiating agents include B cell differentiating factor (BCDF), erythropoietin (EPO), steel factor, activin, inhibin, the bone morphogenic proteins (BMPs), retinoic acid or retinoic acid derivatives such as retinol, the prostaglandins, and TPA.

Alternatively, other cytokines and related antigens in combination with a composition may also be useful to treat or prevent certain virus-associated cellular disorders, virus infections, and other viral disorders. Potentially useful cytokines include tumor necrosis factor (TNF), the interleukins IL-1, IL-2, 11-3, IL-4, IL-5, IL-6, etc., recombinant IL receptors, growth factors, colony stimulating factors, erythropoietin (EPO), the interferon (IFN) proteins IFN-$\alpha$, IFN-$\beta$, and IFN-$\gamma$; cyclic AMP including dibutyryl cyclic AMP, hemin, DMSO, hydroxyurea, hypoxanthine, glucocorticoid hormones, and cytosine arabinoside. Therapies using combinations of these agents would be safe and effective therapies against malignancies and other forms of cancer. Combinations of therapies may also be effective in inducing regression or elimination of a tumor or some other form of cellular disorder resulting from and/or associated with viral infection such as compositions of the invention plus radiation therapy, toxin or drug-conjugated antibody therapy using monoclonal or polyclonal antibodies directed against the transformed cells, or specific anti-sense therapy. Effects may be additive, logarithmic, or synergistic, and methods involving combinations of therapies may be simultaneous protocols, intermittent protocols or protocols that are empirically determined.

Compositions are preferably physiologically stable at therapeutically effective concentrations. Physiological stable compounds are compounds that do not break down or otherwise become ineffective upon introduction to a patient prior to having a desired effect. Compounds are structurally resistant to catabolism, and, thus, physiologically stable, or coupled by electrostatic or covalent bonds to specific reagents to increase physiological stability. Such reagents include amino acids such as arginine, glycine, alanine, asparagine, glutamine, histidine, or lysine, nucleic acids including nucleosides or nucleotides, or substituents such as carbohydrates, saccharides and polysaccharides, lipids, fatty acids, proteins, or protein fragments. Useful coupling partners include, for example, glycol, such as polyethylene glycol, glucose, glycerol, glycerin, and other related substances.

A combination therapy can include administering an agent that reduces side effects of treatments, for example, anti-cancer treatments. A combinational therapy can also include administering an agent that reduces the frequency of administration of other therapies. The agent can be an agent that decreases growth of tumor after the anti-cancer effects of other therapies have decreased. The additional agent or therapy can also be another anti-viral or anti-cancer agent or therapy.

Physiological stability can be measured from a number of parameters such as the half-life of the compound or the half-life of active metabolic products derived from the compound. Certain compounds of the invention have in vivo half-lives of greater than about fifteen minutes, greater than about one hour, greater than about two hours, and greater than about four hours, eight hours, twelve hours, or longer. Although a compound is stable using this criteria, physiological stability can also be measured by observing the duration of biological effects on the patient. Clinical symptoms that are important from the patient's perspective include a reduced frequency or duration, or elimination of the need for transfusions or chelation therapy. Preferably, a stable compound has an in vivo half-life of greater than about 15 minutes, a serum half-life of greater than about 15 minutes, or a biological effect which continues for greater than 15 minutes after treatment has been terminated or the serum level of the compound has decreased by more than half.

Preferably, compositions are also not significantly biotransformed, degraded, or excreted by catabolic processes associated with metabolism. Although there may be some biotransformation, degradation, or excretion, these functions are not significant, if the composition is able to exert its desired effect.

Compositions are also preferably safe at effective dosages. Safe compositions are compositions that are not substantially toxic (e.g. cytotoxic or myelotoxic), or mutagenic at required dosages, do not cause adverse reactions or side effects, and are well-tolerated. Although side effects may occur, compositions are substantially safe if the benefits achieved from their use outweigh disadvantages that may be attributable to side effects. Unwanted side effects include nausea, vomiting, hepatic or renal damage or failure, hypersensitivity, allergic reactions, cardiovascular problems, gastrointestinal disturbances, seizures, and other central nervous system difficulties, fever, bleeding or hemorrhaging, serum abnormalities, and respiratory difficulties.

Compositions useful for treating viral disorders preferably do not substantially affect the viability of a cell such as a normal mammalian cell. Normal cell viability, the viability of an untransformed or uninfected cell, can be determined from analyzing the effects of the composition on one or more biological processes of the cell.

Useful combination therapies will be understood and appreciated by those of skill in the art. Potential advantages of such combination therapies include the ability to use less of each of the individual active ingredients to minimize toxic side effects, synergistic improvements in efficacy, improved ease of administration or use, and/or reduced overall expense of compound preparation or formulation. For example, the inducing agent and anti-viral agent may be administered to the subject in combination with one or more cytokines selected from the group consisting, for example, of IL-3, GM-CSF, stem cell factor (SCF), and IL-6.

Administration of the inducing agent and the anti-viral agent to a subject according to a method of the invention may be for prophylaxis or therapeutic treatment of a confirmed or suspected viral disorder.

Administration may be to an adult, an adolescent, a child, a neonate, an infant or in utero.

Administration of the inducing agent and the anti-viral agent during the first period of a cycle of therapy according to a method of the invention may be in a single or in separate composition(s). Administration of either agent may be continuous or sporadic, as necessary. For example, the inducing agent may be administered to the subject via a continuous infusion throughout the first period of the cycle of therapy. Alternatively, the inducing agent may be administered to the subject per infusion over a single span of a few to several hours per day every day throughout the first period of the cycle of therapy. Alternatively, the inducing agent may be administered in a single parenteral bolus, or orally, daily for several days throughout the first part of the cycle, or weekly. Anti-viral agents are administered to the subject per known or readily determined regimens (for example, one to two intravenous administrations per day throughout the first period of the cycle of therapy, followed by one to two oral administrations per day throughout the remainder of the cycle of therapy). Patients with a suspected or diagnosed viral-associated disorder may only require one or a few cycles of therapy until the disorder has been effectively overcome.

Methods for the treatment of viral disorders may include augmenting the treatment methods of the invention with conventional chemotherapy, radiation therapy, antibody therapy, and/or other forms of therapy. Some conventional chemotherapeutic agents that would be useful in combination therapy with methods and compositions of the invention include the cyclophosphamides such as alkylating agents, the purine and pyrimidine analogs such as mercaptopurine, the vinca and vinca-like alkaloids, the etoposides or etoposide-like drugs, the antibiotics such as deoxyrubocin and bleomycin, the corticosteroids, the mutagens such as the nitrosoureas, antimetabolites including methotrexate, the platinum based cytotoxic drugs, the hormonal antagonists such as anti-insulin and anti-androgen, the anti-estrogens such as tamoxifen, and other agents such as doxorubicin, L-asparaginase, DTIC, mAMSA, procarbazine, hexamethylmelamine, and mitoxantrone. These agents could be given simultaneously or alternately as defined by a protocol designed to maximize effectiveness, but minimize toxicity to the patient's body.

Virus-infected cells may also be treated in vivo by administering the inducing agent and the anti-viral agent directly to the patient. For example, patients exposed to mutagens, carcinogens, radiation, or other cancer-producing agents may be continuously treated with compositions to inhibit the expected development of a neoplastic condition. Patients who have been genetically screened and determined to be at high risk for the future development of a neoplasia may also be administered compositions, possibly beginning at birth and possibly for life. Both prophylactic and therapeutic uses are readily acceptable, because these compounds are generally safe and non-toxic at effective dosages.

Detrimental interference with one or more of these cellular processes becomes significant when the process becomes abnormal. Examples of quantitatable and qualifiable biological processes include the processes of cell division, protein synthesis, nucleic acid (DNA or RNA) synthesis, nucleic acid (principally DNA) fragmentation, and apoptosis. Other processes include specific enzyme activities, the activities of the cellular transportation systems such as the transportation of amino acids by system A (neutral), system B (acidic) or system C (basic), and the expression of a cell surface protein. Each of these parameters is easily determined as significantly detrimental, for example, in tissue culture experiments, in animal experiments, or in clinical studies using techniques known to those of ordinary skill in the art. Abnormal cell division, for example, can be mitosis which occurs too rapidly, as in a malignancy, or unstably, resulting in programmed cell death or apoptosis, detected by increased DNA degradation. The determination of abnormal cell viability can be made on comparison with untreated control cells. Compositions preferably increase normal cell viability. Increased cell viability can be determined by those of ordinary skill in the art using, for example, DNA fragmentation analysis. A decreased amount of fragmentation indicates that cellular viability is boosted. Determinations of increased or decreased viability can also be concluded from an analysis of the results of multiple different assays. Where multiple tests provide conflicting results, accurate conclusions can still be drawn by those of ordinary skill based upon the cell type, the correctness or correlation of the tests with actual conditions, and the type of composition.

Compositions can be prepared in solution as a dispersion, mixture, liquid, spray, capsule, or as a dry solid such as a powder or pill, as appropriate or desired. Solid forms may be processed into tablets or capsules or mixed or dissolved with a liquid such as water, alcohol, saline or other salt solutions, glycerol, saccharides or polysaccharide, oil, or a relatively inert solid or liquid. Liquids, pills, capsules or tablets administered orally may also include flavoring agents to increase palatability. Additionally, all compositions may further comprise agents to increase shelf-life, such as preservatives, anti-oxidants, and other components necessary and suitable for manufacture and distribution of the composition. Compositions further comprise a pharmaceutically acceptable carrier or excipient. Carriers are chemical or multi-chemical compounds that do not significantly alter or affect the active ingredients of the compositions. Examples include water, alcohols such as glycerol and polyethylene glycol, glycerin, oils, salts such as sodium, potassium, magnesium, and ammonium, fatty acids, saccharides, or polysaccharides. Carriers may be single substances or chemical or physical combinations of these substances.

Compositions administered as part of the methods of the invention comprise an inducing agent to induce expression of a gene product in a virus-infected cell and an anti-viral agent whose anti-viral activity relates to or is directed to the expressed product. The gene product expressed may be a viral enzyme or a cellular enzyme or activity that is largely expressed in virus-infected cells. Expression products that can be targeted include enzymes involved with DNA replication, which may be either for repair or replication of the genome, assembly of complete virus particles, generation of viral membrane or walls, RNA transcription or protein translation, or combinations of these activities. Interference with these processes can be performed by inducing and then acting on an enzyme and, preferably, a critical enzyme in the process.

Administration Therapy

Preferably, compositions administered contain chemicals that are substantially non-toxic. Substantially non-toxic means that the composition, although possibly possessing some degree of toxicity, is not harmful to the long-term health of the patient. Although the active component of the composition may not be toxic at the required levels, there may also be problems associated with administering the necessary volume or amount of the final form of the composition to the patient. For example, if the composition contains a salt, although the active ingredient may be at a concentration that is safe and effective, there can be a harmful build-up of sodium, potassium, or another ion. With a reduced requirement for the composition or at least the active component of that composition, the likelihood of such problems can be reduced or even eliminated. Consequently, although patients may suffer minor or short term detrimental side-effects, the advantages of taking the composition outweigh the negative consequences.

Treatment of a patient may be therapeutic and/or prophylactic. Therapeutic treatment involves administration of an inducing agent and an anti-viral agent according to a method of the invention to a patient suffering from one or more symptoms of or having been diagnosed as being afflicted with a viral disorder. Relief and even partial relief from one or more of the symptoms may correspond to an increased life span or, simply, an increased quality of life. Further, treatments that alleviate a pathological symptom can allow for other treatments to be administered.

Prophylactic treatments involve administration of an inducing agent and an anti viral agent according to a method of the invention to a patient having a confirmed or suspected viral disorder without having any overt symptoms. Administration can begin at birth and continue, if necessary, for life. Both prophylactic and therapeutic uses are readily acceptable, because these compounds are generally safe and non-toxic.

Treatments Aids

Aids for the treatment of human viral disorders and virus-associated cellular and neoplastic disorders contain compositions described herein in predetermined amounts, which can be individualized in concentration or dose for a particular patient. Compositions, which may be liquids or solids, are placed into reservoirs or temporary storage areas within the aid. At predetermined intervals, a set amount of one or more compositions is administered to the patient. Compositions to be injected may be administered through, for example, infusion pumps, mediports, or in-dwelling catheters. Aids may further comprise mechanical controls or electrical controls devices, such as a programmable computer or computer chip, to regulate the quantity or frequency of administration to patients. Examples include both single and dual rate infusers and programmable infusers. Delivery of the composition may also be continuous for a set period of time. Aids may be fixed or portable, allowing the patient as much freedom as possible. The use of a portable aid allows the patient to receive at least a portion of the treatment regimen outside of the hospital.

Administration Schedule

Administration of one or more agents (e.g, a viral inducing agent and/or an antiviral) can be intermittent; for example, administration can be once every two days, every three days, every five days, once a week, once or twice a month, and the like. The amount, forms, and/or amounts of the different forms can be varied at different times of administration.

Pulsed administration of one or more pharmaceutical compositions can be used for the treatment or prevention of a viral-induced inflammatory disease. Pulsed administration can be more effective than continuous treatment as pulsed doses can be lower than would be expected from continuous administration of the same composition. Each pulse dose can be reduced and the total amount of drug administered over the course of treatment to the patient can be minimized.

With pulse therapy, in vivo levels of an agent can drop below that level required for effective continuous treatment. Pulsed administration can reduce the amount of the composition administered to the patient per dose or per total treatment regimen with an increased effectiveness. Pulsed administration can provide a saving in time, effort and expense and a lower effective dose can lessen the number and severity of complications that can be experienced by a subject. As such, pulsing can be more effective than continuous administration of the same composition.

Individual pulses can be delivered to a subject continuously over a period of several hours, such as about 2, 4, 6, 8, 10, 12, 14 or 16 hours, or several days, such as 2, 3, 4, 5, 6, or 7 days, or from about 1 hour to about 24 hours or from about 3 hours to about 9 hours. Alternatively, periodic doses can be administered in a single bolus or a small number of injections of the composition over a short period of time, for example, less than 1 or 2 hours. For example, arginine butyrate can be administered over a period of 4 days with infusions for about 8 hours per day or overnight, followed by a period of 7 days of no treatment.

The interval between pulses or the interval of no delivery can be greater than 24 hours or can be greater than 48 hours, and can be for even longer such as for 3, 4, 5, 6, 7, 8, 9 or 10 days, two, three or four weeks or even longer. The interval between pulses can be determined by one of ordinary skill in the art. The interval between pulses can be calculated by administering another dose of the composition when the composition or the active component of the composition is no longer detectable in the patient prior to delivery of the next pulse. Intervals can also be calculated from the in vivo half-life of the composition. Intervals can be calculated as greater than the in vivo half-life, or 2, 3, 4, 5 and even 10 times greater than the composition half-life. Intervals can be 25, 50, 100, 150, 200, 250 300 and even 500 times the half life of the chemical composition.

The number of pulses in a single therapeutic regimen can be as little as two, but can be from about 5 to 10, 10 to 20, 15 to 30 or more. Subjects (e.g., patients) can receive one or more agents (e.g., drugs) for life according to the methods of this invention. Compositions can be administered by most any means, and can be delivered to the patient as an injection (e.g. intravenous, subcutaneous, intraarterial), infusion or instillation, and more preferably by oral ingestion. Various methods and apparatus for pulsing compositions by infusion or other forms of delivery to the patient are disclosed in U.S. Pat. Nos. 4,747,825; 4,723,958; 4,948,592; 4,965,251 and 5,403,590.

In one embodiment, the inducing agent and the anti-viral agent are administered for about five days, and the anti-viral agent is subsequently administered without the inducing agent for an additional period of about sixteen days for a total cycle of about 21 days. Cycles of treatment may occur in immediate succession or with an interval of no treatment between cycles.

A pharmaceutical composition comprising a viral inducing agent can be administered to a subject before a pharmaceutical composition comprising an antiviral agent is administered to the subject. A pharmaceutical composition comprising a viral inducing agent can be co-administered to a subject with a pharmaceutical composition comprising an antiviral agent. A pharmaceutical composition comprising a viral inducing agent can be co-administered with a pharmaceutical composition comprising an antiviral agent and a pharmaceutical composition comprising one or more addition agents. The pharmaceutical compositions can be provided by pulsed administration. For example, a pharmaceutical composition comprising a viral inducing agent can be administered to a subject, followed by administration of a pharmaceutical composition comprising an antiviral agent to the subject after an interval of time has passed, and this order of administration the same or similar time interval can be repeated, for example, at least 1, 2, 3, 4, 5, 6, 7, 8, 9, or 10 or more times.

INCORPORATION BY REFERENCE

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference and may be employed in the practice of the invention. More generally, documents or references are cited in this text, either in a Reference List before the claims, or in the text itself; and, each of these documents or references ("herein cited references"), as well as each document or reference cited in each of the herein cited references (including any manufacturer's specifications, instructions, etc.), is hereby expressly incorporated herein by reference.

EXAMPLES

Example 1. Phase 1 Study of AB Plus Ganciclovir in Patients with EBV Associated Lymphoid Malignancies Fifteen patients with EBV-associated lymphoid malignancies, who had histologically confirmed lymphoid neoplasms that were EBV+, were treated with AB and GCV. Prior therapies (varying in different subjects) included rituximab, chemotherapy, chemoradiotherapy and bone marrow transplant. GCV was administered at a rate of 5 mg/kg intravenously (IV) over 1 hour twice per day, and continued throughout the cycle. AB was continuously infused at a starting dose of 500 mg/kg/day. Dose escalation was continued as follows until MTD was established:
Level 1: 500 mg/kg/day IV for 2 days
Level 2: 1000 mg/kg/day IV for 2 days
Level 3: 1500 mg/kg/day IV for 2 days
Level 4: 2000 mg/kg/day IV until day 21

A total of 15 patients were evaluated for anti-tumor response (Table 1). A complete response (CR) was defined as disappearance of detectable malignant disease on imaging or physical examination (e.g., for skin lesions or tonsillar masses). A partial response (PR) was defined as a 50% decrease in tumor size (the sum of the product of the largest perpendicular diameters) or measurable lesions chosen for analysis prior to beginning of treatment. For lesions which could only be measured in 1 dimension, such as skin (cutaneous T cell lymphoma), a greater than 50% decrease in the largest dimension qualified as a PR. For the 3 patients who died from co-morbidities, anti-tumor responses were confirmed pathologically at autopsy.

Four patients were classified as achieving CRs, including 2 with PTLD, 1 with extranodal NK/T cell lymphoma and 1 with peripheral T-cell lymphoma. Three of these patients died after completing therapy as a result of co-morbid conditions and complications presumed related to tumor regression. Autopsy examination of 2 subjects revealed apparent complete disappearance of tumor, while the third patient demonstrated significant necrosis of residual lymphoma at autopsy.

Six patients were classified as partial responses (PRs), including 3 with PTLD, 1 with diffuse large-cell B-cell lymphoma, 1 with extranodal NK/T-cell lymphoma and 1 with subcutaneous panniculitis-like T-cell lymphoma.

The remaining 5 patients were classified as non-responders (NR).

TABLE 1

Treatment Courses in Patients With EBV Associated Lymphoid Malignancies Treated with AB and GCV

| Patient Number | No. Cycles | HD/HTD[1] (mg/kg/day) | Outcome, 1 cycle | Adverse Events |
|---|---|---|---|---|
| 1 | <1, 15 d | 500 | CR | confusion; diarrhea; emesis; rejection of lung transplant* |

TABLE 1-continued

Treatment Courses in Patients With EBV Associated Lymphoid Malignancies Treated with AB and GCV

| Patient Number | No. Cycles | HD/HTD[1] (mg/kg/day) | Outcome, 1 cycle | Adverse Events |
|---|---|---|---|---|
| 2 | <1, 16 d | 1800 | CR | confusion; mucositis; headache; nausea; vomiting; abdominal pain |
| 3 | <1, 19 d | 2000 | PR | confusion; mucositis; headache; nausea/vomiting; tumor regression preceding bowel perforation* |
| 4 | 1 | 2000 | PR | confusion: nausea/vomiting; anorexia |
| 5 | 1 | 2000 | NR | confusion; restlessness; somnolence; nausea; vomiting; abdominal pain; vision change; orthostasis |
| 6 | 1 | 1000/1000 | NR | Headache; nausea/vomiting; abdominal pain; thrombocytopenia |
| 7 | 1 | 2000/1500 | CR | Lethargy/stupor/confusion; hypotonia/hypoesthesia; fungal infection/mucositis; tumor lysis leading to hemorrhage* |
| 8 | 1 | 1500/1000 | PR | Acoustic hallucinations; somnolence; hypokalemia; sepsis; Deep Vein Thrombosis |
| 9 | 1 | 2000/2000 | CR | Confusion; fatigue; elevated BUN; tumor lysis leading to pancreatitis/hepatitis* |
| 10 | 1 | 1000/800 | NR | Elevated BUN, encephalopathy |
| 11 | <1, 8 d | 1500/1500 | PR | Diarrhea; hepatomegaly |
| 12 | 1 | 2000/2000 | NR | Nausea; pneumonia; port infection |
| 13 | 3 | 938/938 | PR | Nausea; anorexia; weight loss; anemia; thrombocytopenia; lethargy; insomnia; hypokalemia |
| 14 | <1, 19 d | 1250/1250 | NR | Sinus, throat, back pain; thrombocytopenia; hypokalemia; lethargy |
| 15 | <1, 5 d | 1000/1000 | PR | Lethargy; increased dyspnea; polymicrobial pneumonia/acute respiratory distress syndrome |

*fatal AE;
[1]HD/HTD-highest dose/highest tolerated dose.

In summary 10 out of 15 patients showed a degree of response to treatment of AB in combination with the anti-viral ganciclovir.

Example 2. Phase II Trial of Low-Dose Arginine Butyrate and Ganciclovir/Valganciclovir in EBV(+) Lymphoid Malignancies It has previously been found that continuous infusion of inducing agent, for example, arginine butyrate, may not be necessary to maintain viral thymidine kinase expression and sensitization to anti-viral agents in EBV-associated tumors, but that, in fact, cells that survived initial exposure to the inducing agent plus the anti-viral agent remained susceptible to further cycles of combination treatment (Ghosh, S. K., et al. 2007 Blood Cells, Molecules, and Diseases 38:57-65, incorporated herein in its entirety). However, it was neither anticipated nor expected that after some first period of treatment with inducing agent and anti-viral agent, one could continue the anti-viral treatment effectively within a cycle of therapy without continued administration of the inducing agent (continued administration including continued periods of pulsing throughout).

A clinical trial was instituted utilizing a 5-day infusion of arginine butyrate and 21 days of ganciclovir/valganciclovir for EBV+lymphomas and Post-transplant Lymphoproliferative Disorder (PTLD). The first patient enrolled in the protocol (with Rituximab-refractory PTLD following a cord stem cell transplantation for Hodgkin Disease) tolerated the treatment regimen well, with resolution of cough within three days and a decrease in LDH levels.

Figure 1A:

Treatment with arginine butyrate (AB) was administered in a hospital/inpatient basis. The subject was a 32 year old with EBV-related post-transplant lymphoma who had failed multiple therapies (chemotherapy, Rituxan). The subject received AB 1,000 mg/kg/dose intravenously for 5 days (day 1-5). The dose was given continuously over 24 hours. AB was given through along IV line or port due to hypertonicity. Ganciclovir at 5 mg/kg IV over 1 hour was given twice a day for five days (day 1-5). Valganciclovir 900 mg was given orally twice per day for 16 days (day 6-21). At the end of the 21-day cycle, imaging studies were done to determine response and revealed elimination of nearly all tumor masses (FIG. 1). Four of six target lesions resolved completely, and two additional lesions decreased in size. (Table 2) The subject's symptoms of fever and cough resolved for first time in 9 weeks. Measure of the tumor marker serum LDH was reduced from 899 to 328 (normal). Additionally, EBV, CMV, and HH6 viral load became undetectable. These findings indicate that a shorter, more patient-accessible regimen of the virus-target therapeutic strategy is more efficacious.

TABLE 2

Quantification of tumor response evaluated by CT Scan. Tumor dimensions in cm.

| | Pre-Treatment | | Post-Treatment | |
|---|---|---|---|---|
| Location | Dimension 1 | Dimension 2 | Dimension 1 | Dimension 2 |
| R. Upper lobe | 0.7 | 0.7 | None | None |
| R. Mid Lobe | 1.1 | 1.1 | None | None |
| R. Lower Lobe | 1.4 | 0.8 | 0.8 | 0.6 |
| L. Upper Lobe | 0.9 | 0.8 | None | None |
| L. Lower Lobe | 0.9 | 0.6 | 0.6 | 0.5 |

TABLE 2-continued

Quantification of tumor response evaluated by CT Scan. Tumor dimensions in cm.

| Location | Pre-Treatment | | Post-Treatment | |
|---|---|---|---|---|
| | Dimension 1 | Dimension 2 | Dimension 1 | Dimension 2 |
| Lingular | 0.9 | 0.7 | None | None |
| Hepatic Seg. 6 | 1.1 | 1.1 | None | None |
| Hepatic Seg. 8 | 1.0 | 0.7 | None | None |
| L. Ant. Abd. Wall | 1.1 | 1.9 | None | None |
| R. Ant. Abd. Wall | 0.9 | 0.5 | 0.9 | 0.5 |

Example 3: Analysis of Efficacy of the Herpes Anti-Virals

There are 12 mammalian HDACs, and any one of which might be required for repression of TK gene during latency in tumors. HDAC isozyme-specific siRNAs were used to to knockdown individual HDACs in tumor lines expressing latent EBV to determine which one of them induces reactivation of TK from latency, rendering it susceptible to anti-virals.

The EBV-positive B lymphoma cell line P3HR1 was used throughout these assays. The P3HR1 cell line was originally derived from Burkitt's lymphoma patient. EBV maintains a latent state of replication in this cell line. Cells were maintained in RPMI 1640 with 10% fetal bovine serum containing 100 U penicillin per ml and 100 µg streptomycin per ml. The HDAC inhibitors used were from five different classes: a) short chain fatty acids, b) hydroxamic acids, c) benzamides, d) cyclic tetrapeptides, and e) largazoles.

To measure the relative level of TK mRNA in various total RNA preparations, reverse transcription and quantitative PCR using real time PCR technology was used. Five micrograms of total RNA was reverse-transcribed using random hexamer primers and Superscript III cDNA synthesis kit (Invitrogen). The cDNA was diluted to a final volume of 60 µl with sterile water, 8 µl of which was then used in each real time PCR reaction in an ABI 7500 Sequencher using SYBR-Green technology. Primers used for the amplification of TK were EBV-TK1-F: 5'-AGATGACGACGGCCTCTACCA-3'; EBV-TK1-R: 5'-CCTCCTTCTGTGCACGAAGT-3'. The ß-actin mRNA level in those samples were determined similarly using ß-actin-specific primers Actin/hu-F: 5'-GCTCGTCGTCGACAACGGCTC-3'; Actin/hu-R: 5'-CAAACATGATCTGGGTCATCTTCTC-3'. The relative level of TK expression in a sample was calculated following normalization of ß-actin expression level.

Figure 2A:
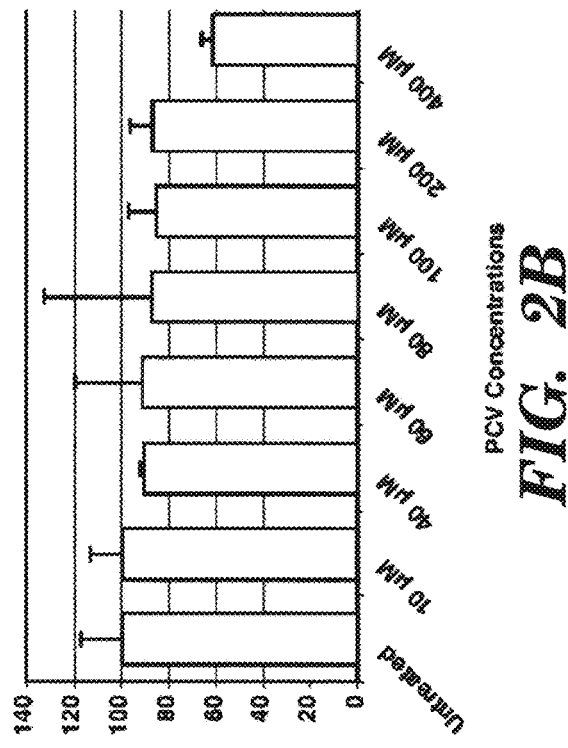
FIGS. 2A-2B illustrate results from toxicity assays with anti-herpesvirus drugs ganciclovir (GCV) and penciclovir (PCV).
Figure 2B:
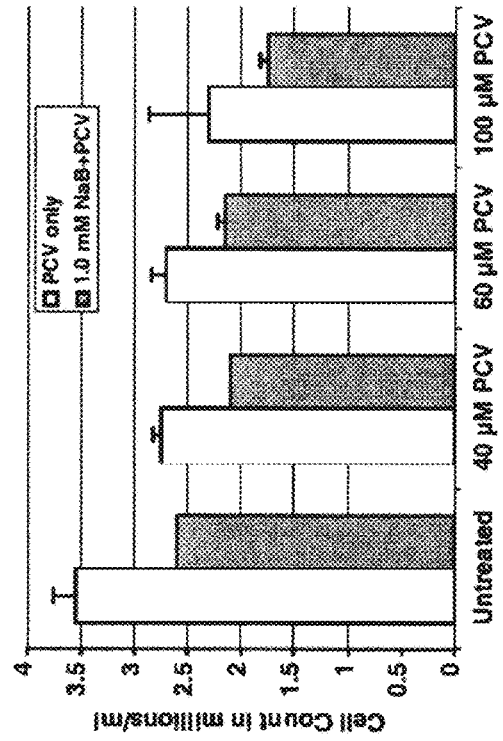
Figure 2C:
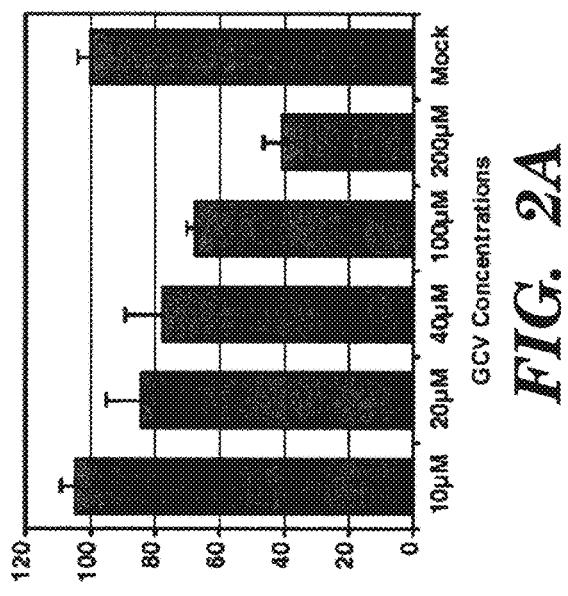
FIGS. 2C and 2D show results from GCV and PCV used in combination with NaB.
Figure 2D:
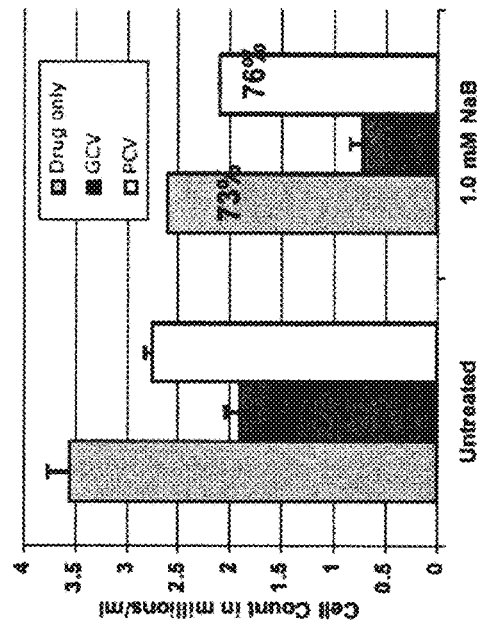

Toxicity assays with two anti-herpesvirus drugs, Gancicovir (GCV) and Penciclovir (PCV), treated to P3HR1 cells alone was conducted as a control. A total of $3\times10^5$ P3HR1 cells were incubated with various concentrations of GCV or PCV and incubated for 6 days. Viable cell counts were measured and toxicity was expressed as percentage of cell growth compared to untreated cells. As shown in FIGS. 2A and 2B, PCV was less toxic to the cells compared to GCV. The effect of 40 µM GCV and PCV in combination treatment approach with 1.0 mM Na-butyrate in P3HR1 cells was compared (FIG. 2C). Inhibition of cell growth with 40 µM PCV (76%) was much less than with 40 µM GCV (38%). This lower level of inhibition of cell growth with PCV did not change significantly when the drug was used at higher concentrations (FIG. 2D).

Example 4: Analysis of Efficacy of HDAC Inhibitors

A. Short Chain Fatty Acids

Figure 3A:
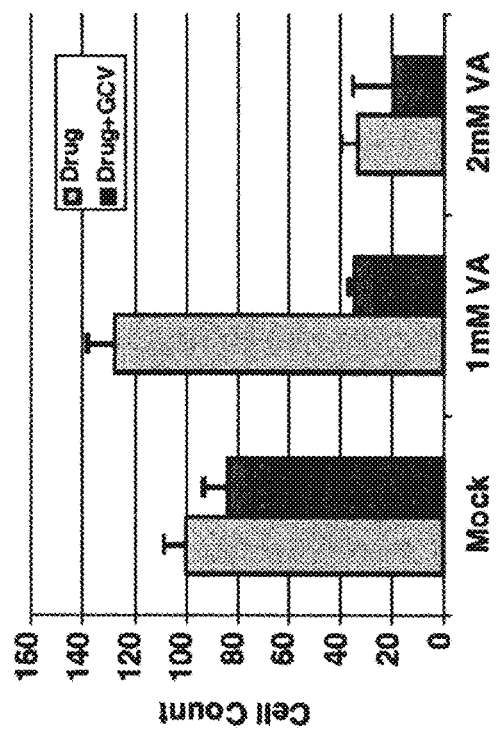
FIGS. 3A-3C illustrate the results from analysis of efficacy of anti-virals using short chain fatty acids as inducing agents.
Figure 3B:
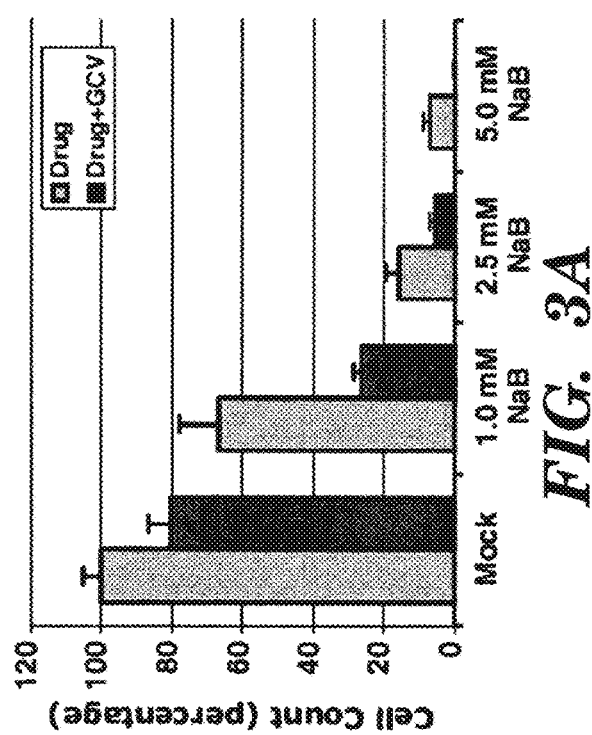
Figure 3C:
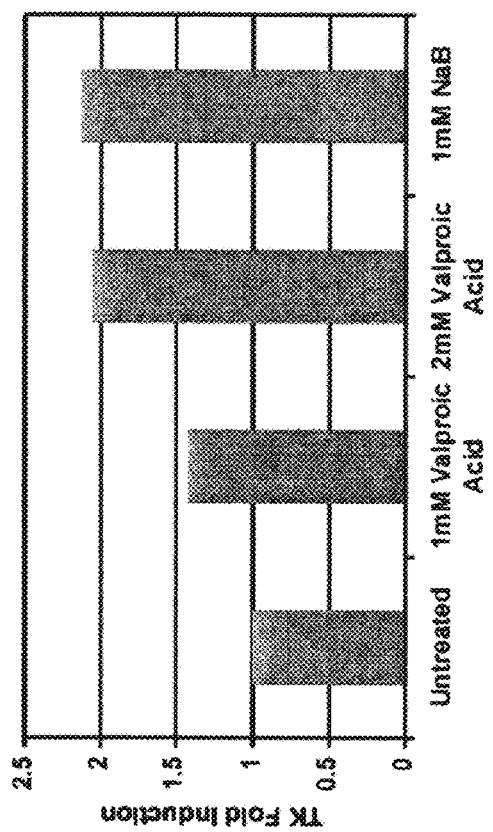

Two SCFA HDAC inhibitors, Na-butyrate (NaB) and valproic acid (VA) were tested. In a combination treatment approach, NaB+GCV reduced growth of EBV-positive P3HR1 cells significantly (up to 50% more) compared to cells treated with NaB or GCV alone (FIG. 3A). The optimal concentration of NaB for this purpose was found to be 1.0 mM. Responses from 1.0 mM NaB was used as a control for interpreting results in this experiment. At a higher concentration NaB alone reduces cell growth to a significant degree, and the synergistic effects of GCV are lost at those concentrations of NaB. The other HDACi used in this experiment, VA, also had very similar activity (FIG. 3B). Analysis of TK mRNA level by RT and real-time PCR however showed that VA was less efficient than NaB in inducing TK expression (FIG. 3C).

B. Hydroxamic Acids

A total of five different HDAC inhibitors from the hydroxamic acid group were examined as combination therapies. These inhibitors include scriptaid, SAHA, panobinostat-LHB589, belinostat-PXD101 and oxamflatin.

Figure 4A:
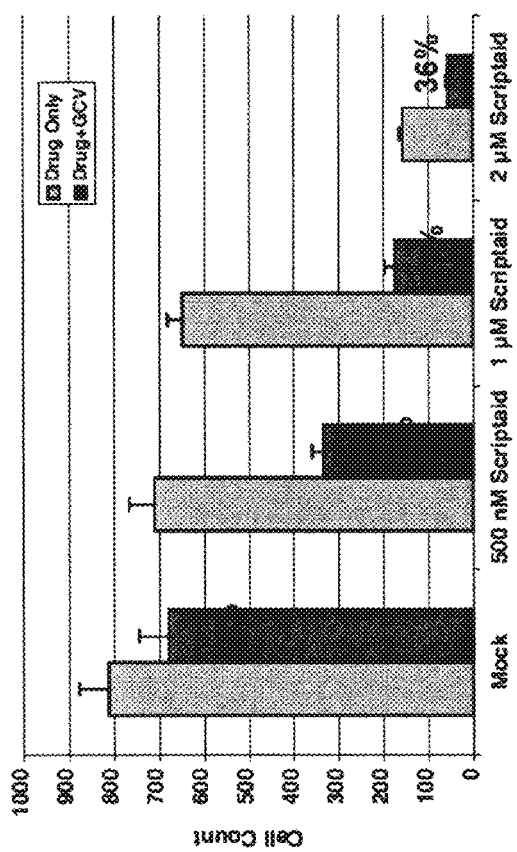
FIGS. 4A-4B illustrate results from analysis of efficacy of anti-virals using hydroxamic acids as inducing agents.
Figure 4B:
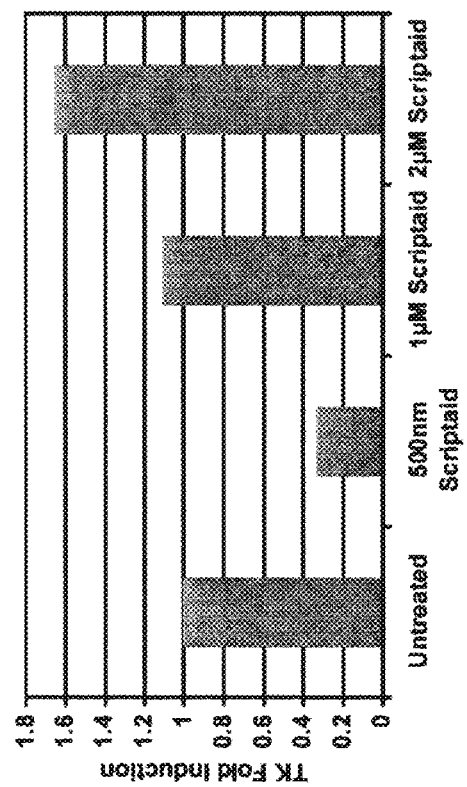

Scriptaid: Scriptaid showed strong synergistic effect with GCV in reducing cell growth of P3HR1 cells, especially at 500 nM and 1 µM concentrations (FIG. 4A).

Figure 5B:
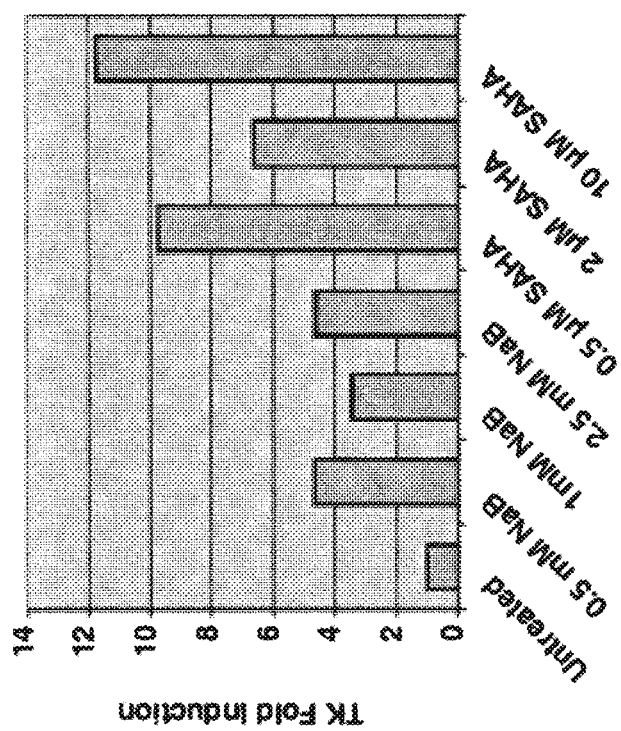
FIGS. 5A-5B illustrate results from analysis of efficacy of anti-virals using SAHA (Vorinostat) as an inducing agent.
Figure 5A:
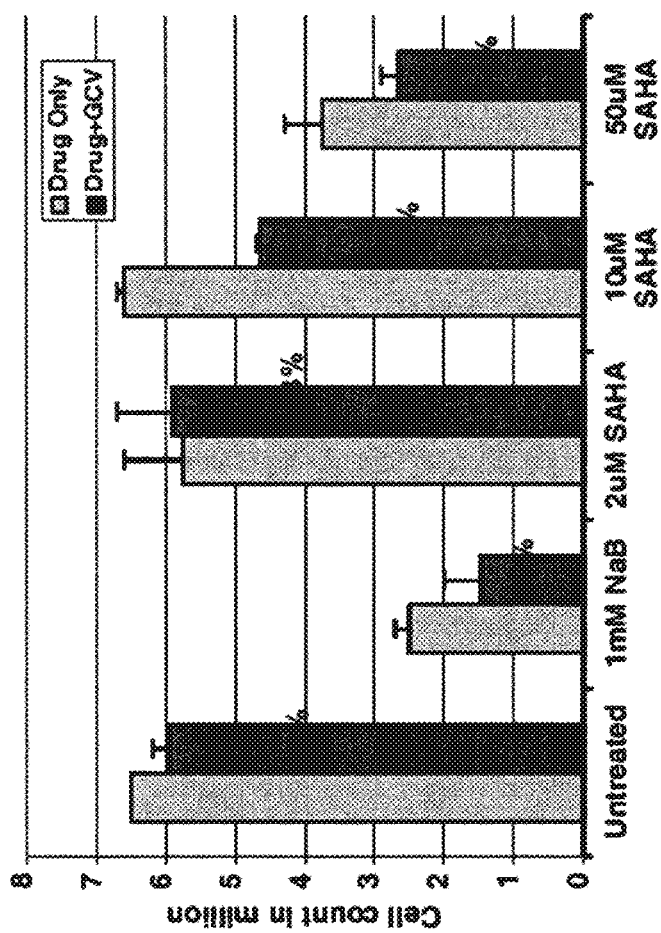

SAHA-Vorinostat: The combination treatment experiment with SAHA showed that it was less effective in reducing cell growth when combined with an antiviral agent compared to butyrate (FIG. 5A) although it did induce TK expression at a higher level than that seen with efficient concentrations of butyrate (1.0 mM) (FIG. 5B).

LHB589-Panobinostat: The growth inhibitory activity of LHB589 at a 50 nM concentration was comparable to that of NaB at 1.0 mM (FIG. 6A). When the cells were treated for 3 days or longer, LHB589 was extremely toxic to the cells at any concentrations 100 nM or above. Although when treated for 24 h only, cells survived well even at a concentration of 5 µM. TK expression level in presence of LHB589 was quite high compared to optimum concentration of NaB (2.5 mM) (FIG. 6B).

Figure 7:
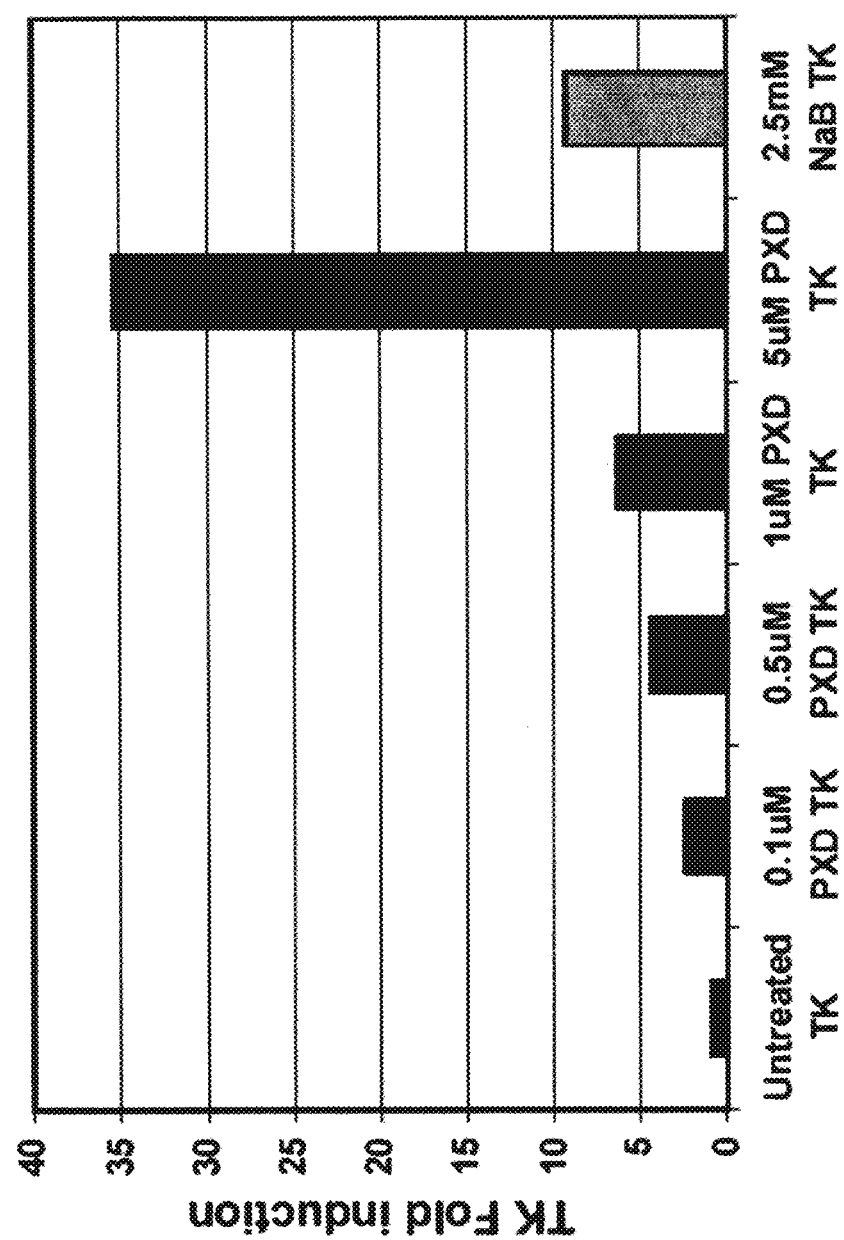
FIG. 7 illustrates results from analysis of efficacy of anti-virals using PXD101 which induced a high level of TK expression at the 5 µM concentration.

PXD101-Belinostat: PXD101 induced high level of TK expression at the 5 µM concentration. (FIG. 7).

Figure 8:
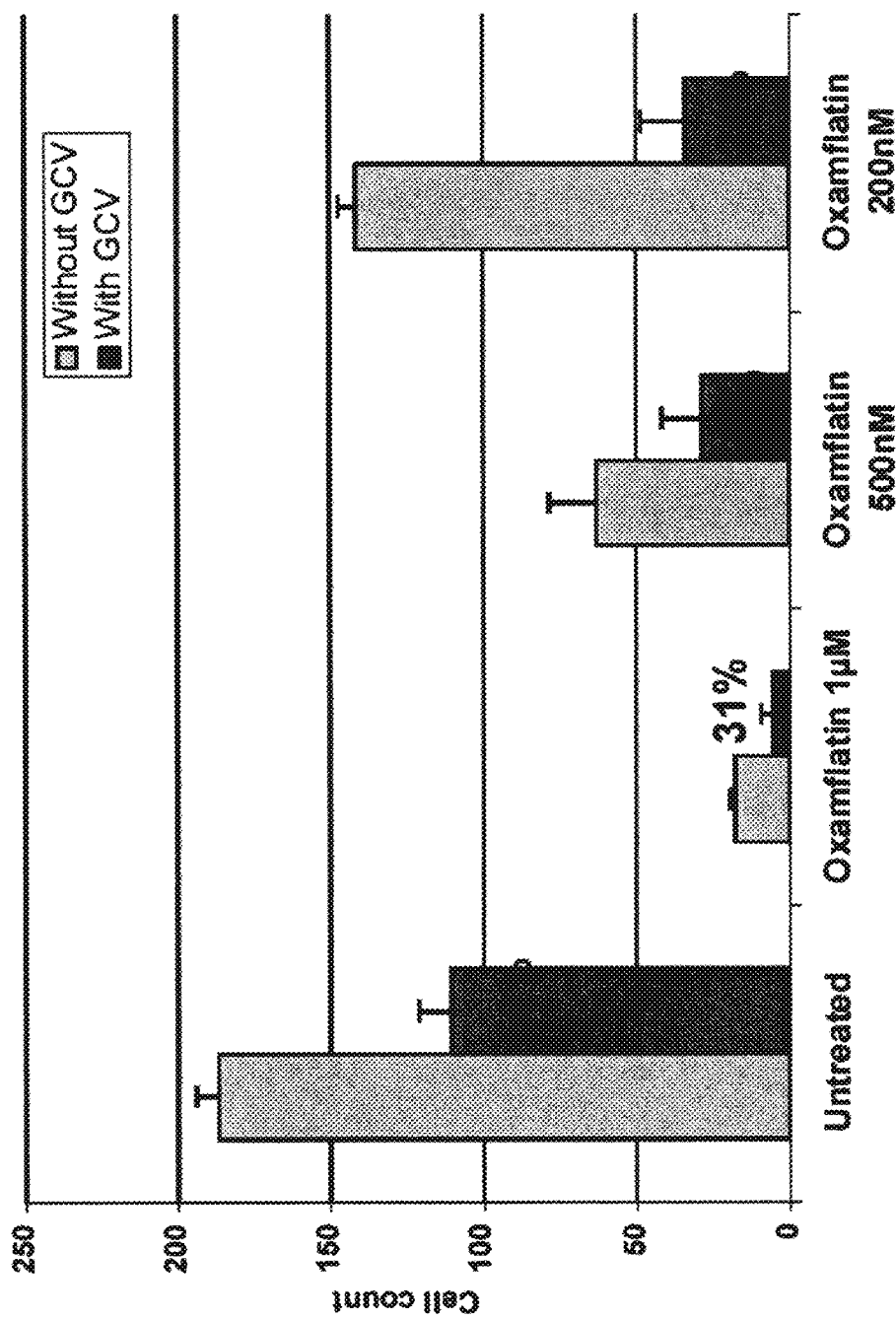
FIG. 8 illustrates results from analysis of efficacy of anti-virals using oxamflatin as an inducing agent.

Oxamflatin: Oxamflatin showed synergistic activity with GCV towards reducing cell growth. At a 200 nM concentration, the activity level (growth suppression) was more than what typically seen with 1.0 mM NaB. (FIG. 8)

C. Cyclic Tetrapeptide

Figure 9:
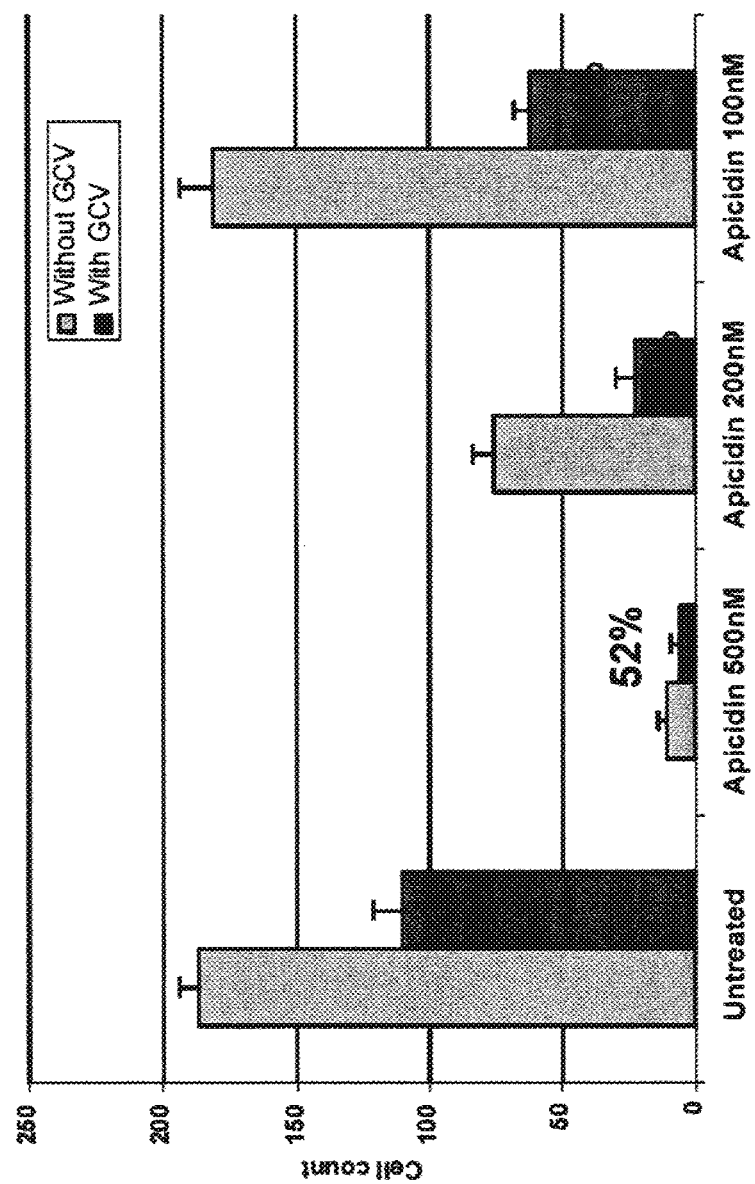
FIG. 9 illustrates results from analysis of efficacy of anti-virals using a cyclic tetrapeptide as an inducing agent.

Apicidin: The cyclic tetrapeptide group of HDACi examined was apicidin. A toxicity assay with apicidin alone showed that concentrations of apicidin higher than 200 nM was quite toxic to the cells. The combination treatment assay (FIG. 9) showed that at 100 nM and 200 nM concentrations, apicidin reduced cell growth by 40-50% over cells treated with apicidin alone. However, the 200 nM concentration cell growth was significantly retarded without any GCV and a 500 nM concentration was very toxic to the cells.

D. Benzamide

Figures 10A, 10B:
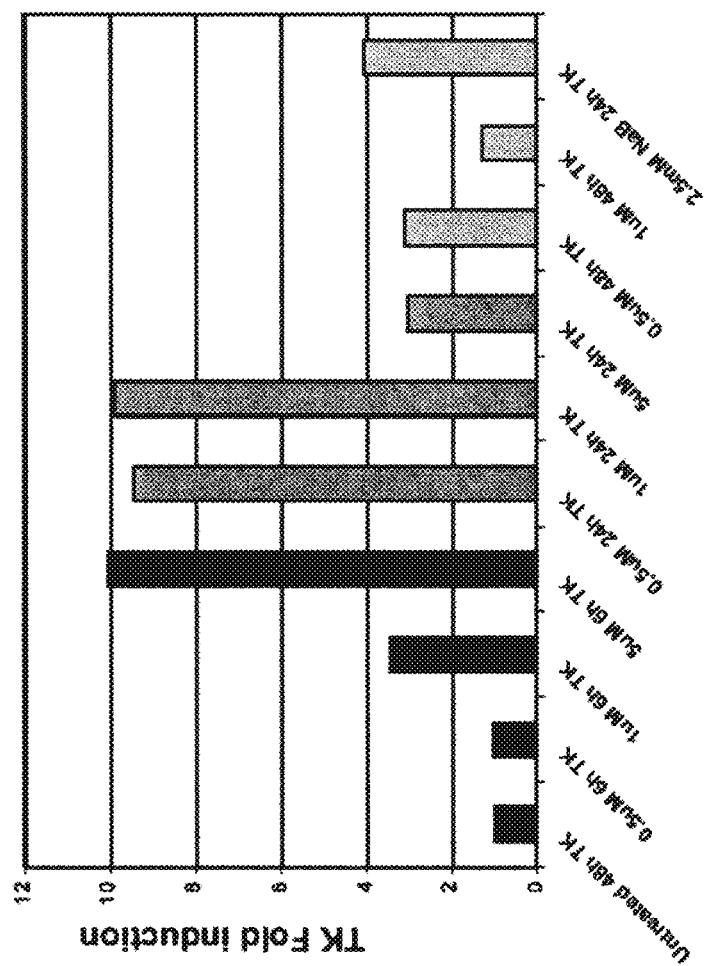
FIGS. 10A-10C illustrate results from analysis of efficacy of anti-virals using a benzamide (MS-275) as an inducing agent.

Experiments show that the benzamide class of HDAC inhibitors were extremely potent in sensitizing P3HR1 cells to GCV-mediated effects. As shown below (FIG. 10A) a 500 nM concentration of MS-275 was as efficient as 1.0 mM NaB. Higher concentrations were extremely toxic to the cells. Interestingly, MS-275 also strongly induced TK expression at 500 nM and higher concentrations (FIG. 10B). TK expression was also induced at only 6 hr post treatment.

Figure 10C:
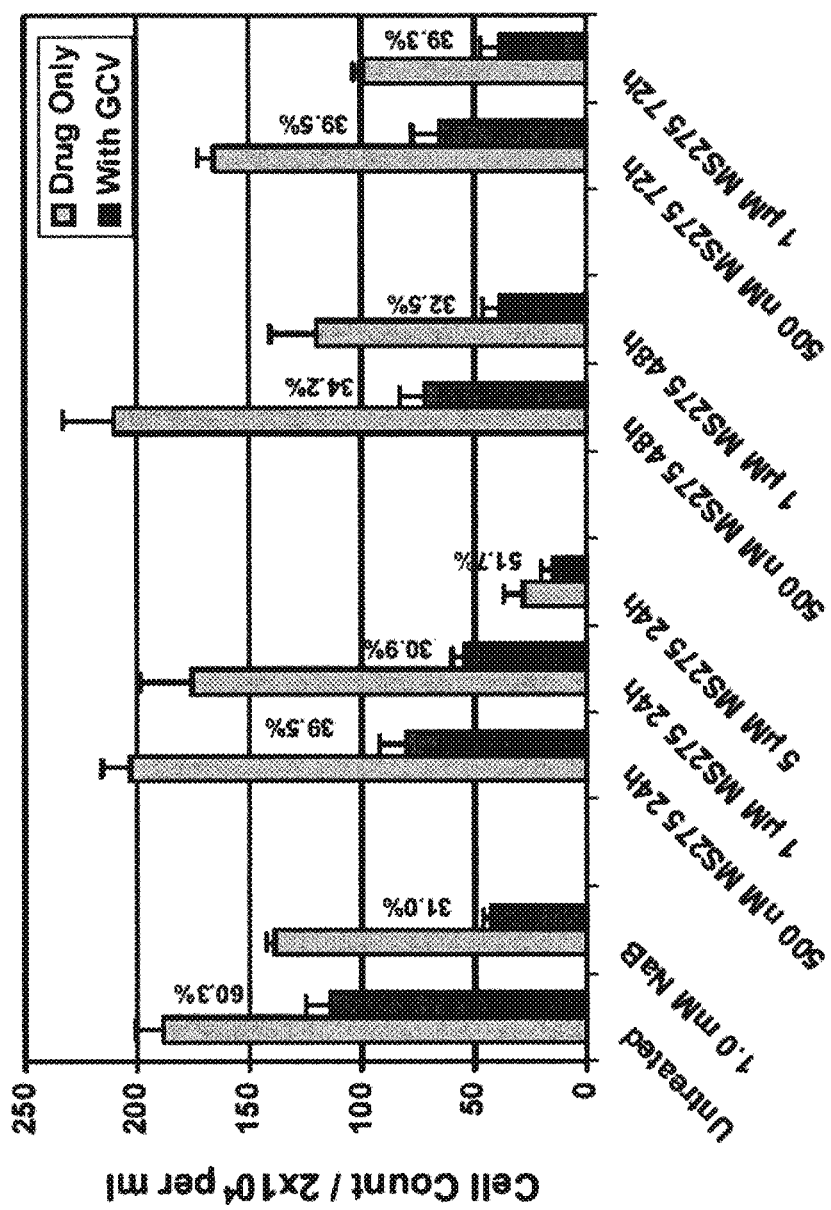
Figure 11A:
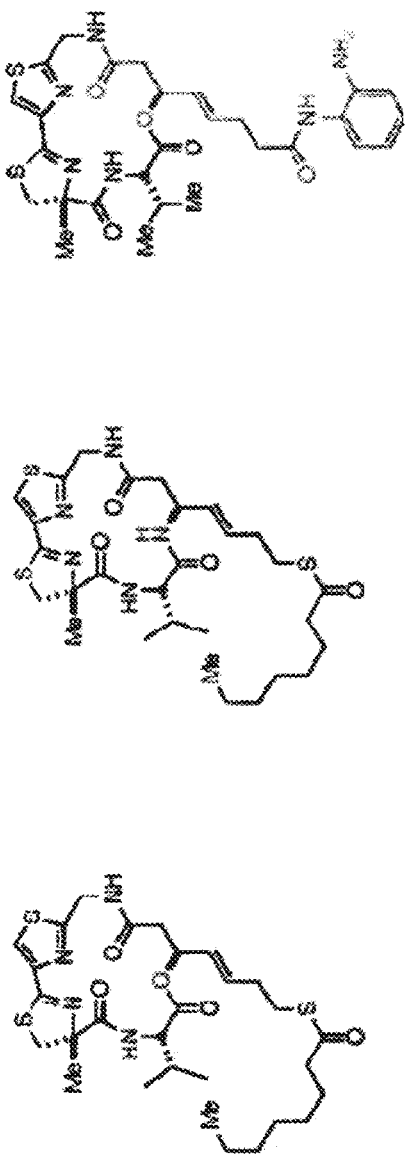
FIGS. 11A-11B illustrate chemical structures of largazole compounds used. Shown in both FIGS. 11A and 11B.
Figure 11B:
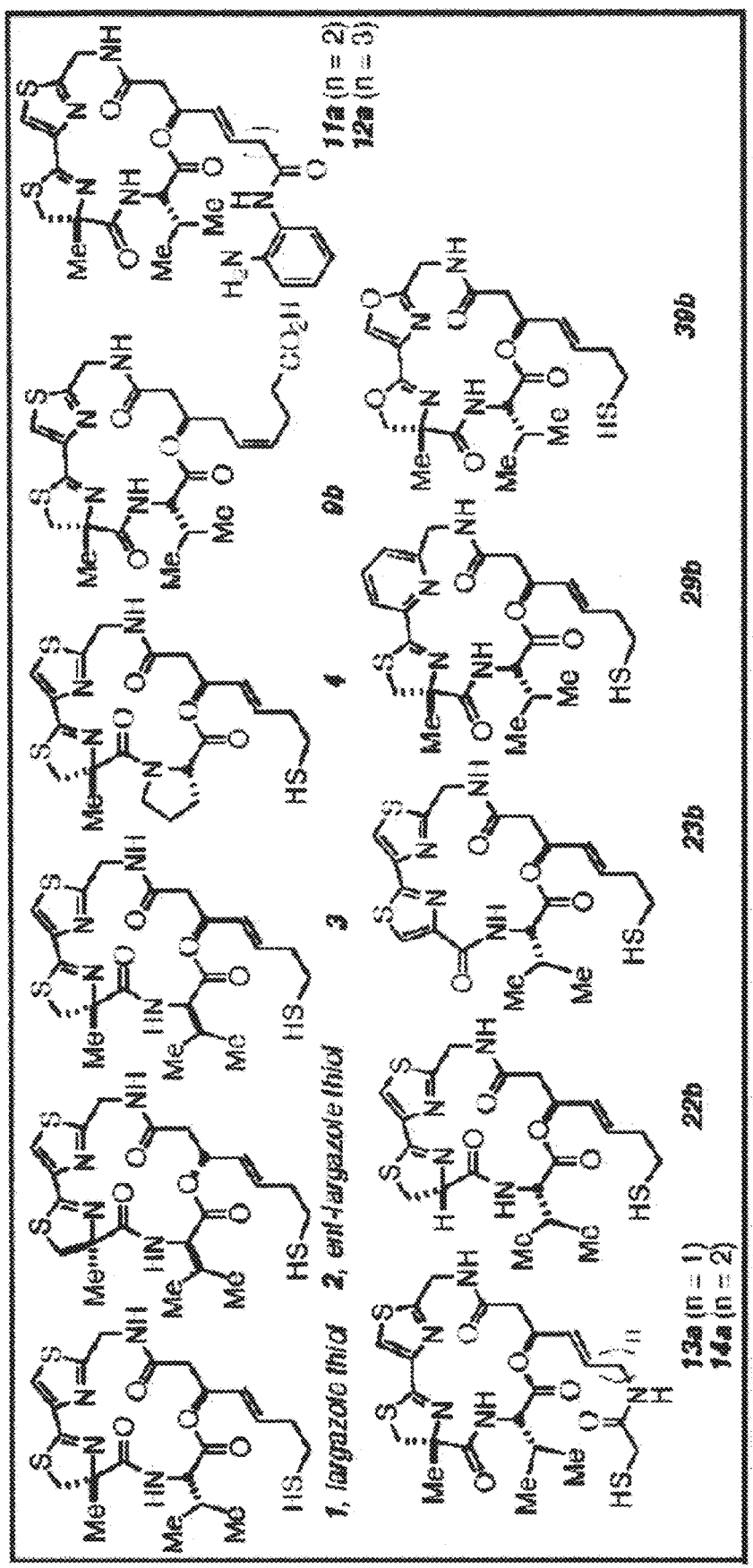

Based on these results, an even shorter exposure to MS-275 was examined to see if it would be sufficient to sensitize P3HR1 cells to GCV-mediated killing. Cells with were treated with MS-275+GCV for shorter time periods of 24 hr or 48 hr (as opposed to 72 hr) and then further incubated in presence of GCV for up to 6 days, at which time the viable cell counts were enumerated. As shown in FIG. 10C, even at just 24 hr exposure to MS-275 sensitized the cells to GCV-mediated effects as efficiently as a 72 hr continuous treatment. This further demonstrates that MS-275 is very effective sensitizing agent for combination treatment studies.

E. Largazole

Figure 12A:
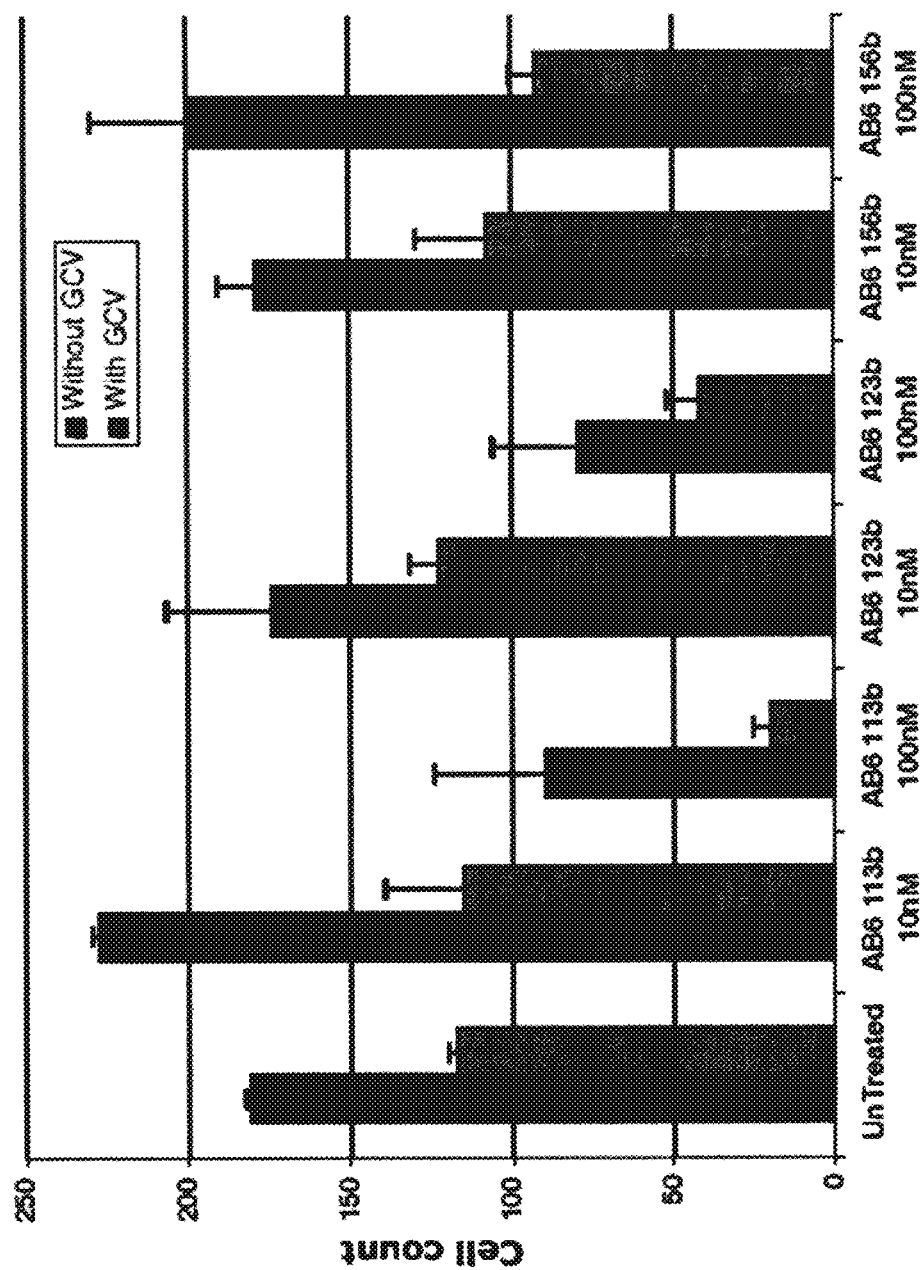
FIGS. 12A-12F illustrate results from analysis of efficacy of anti-virals using largazoles as an inducing agent.
Figure 12B:
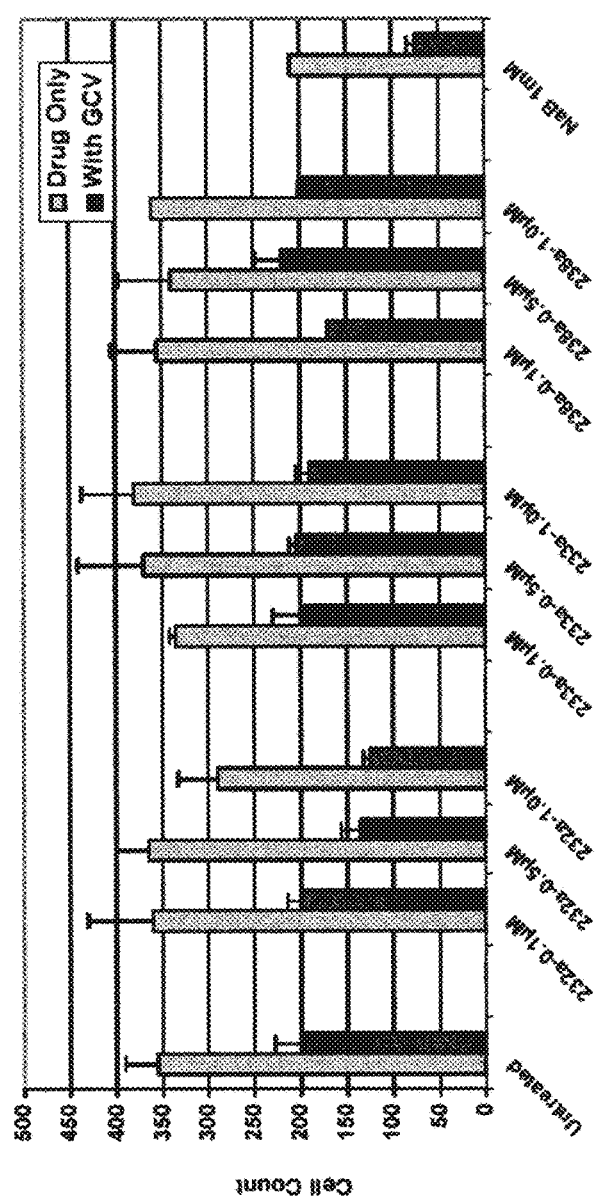
Figure 12C:
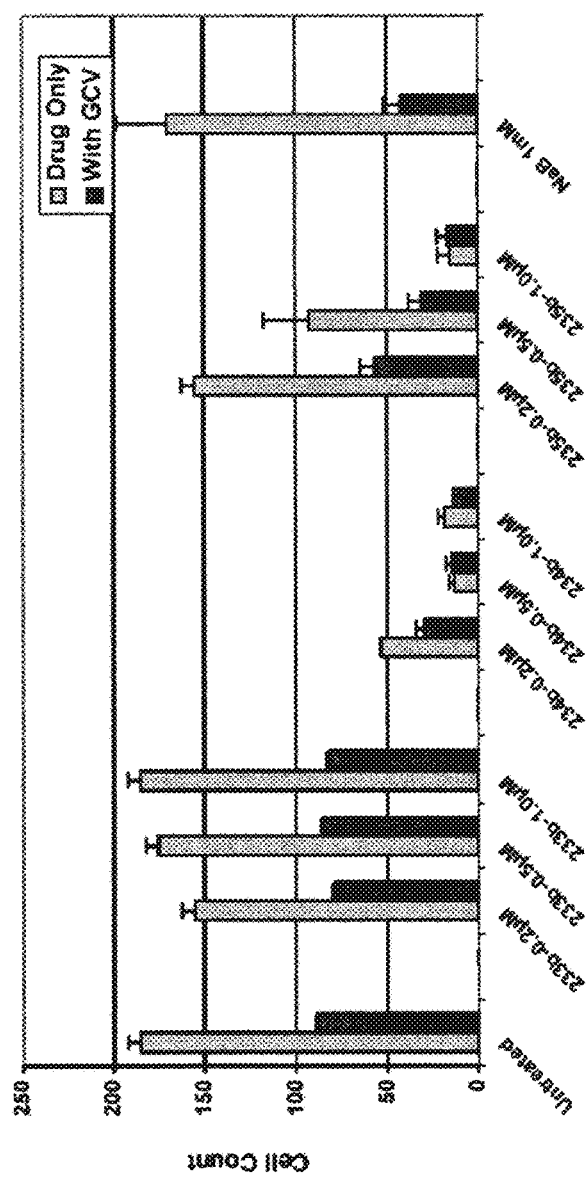
Figure 12D:
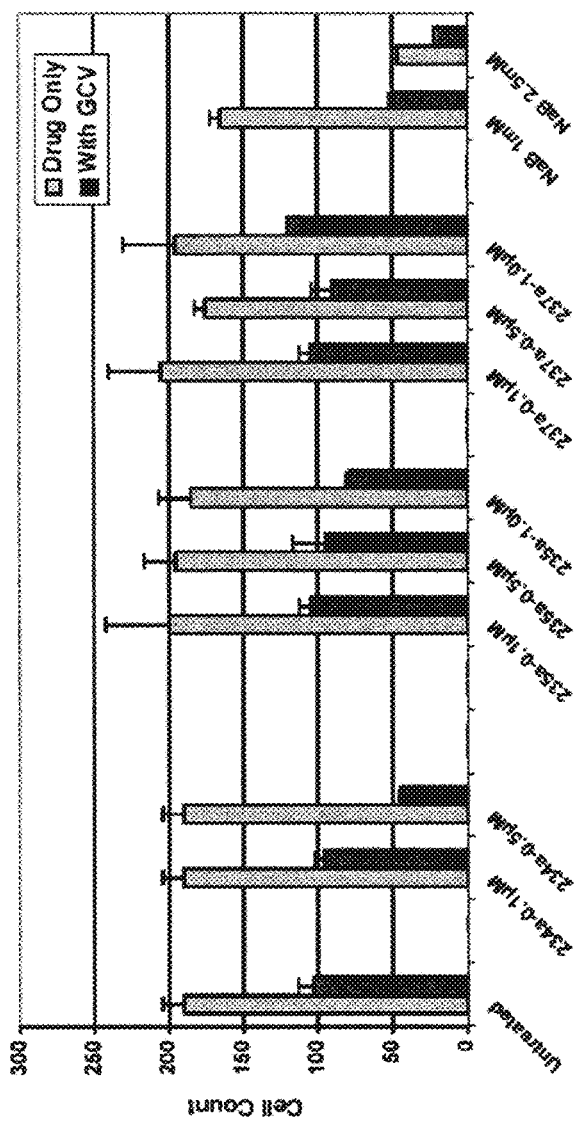
Figure 12E:
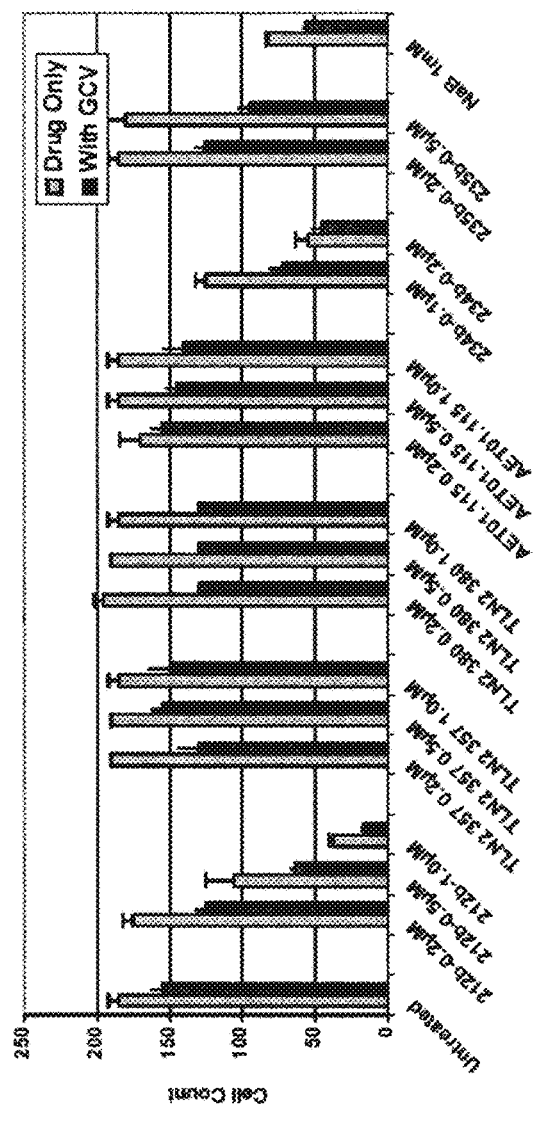
Figure 12F:
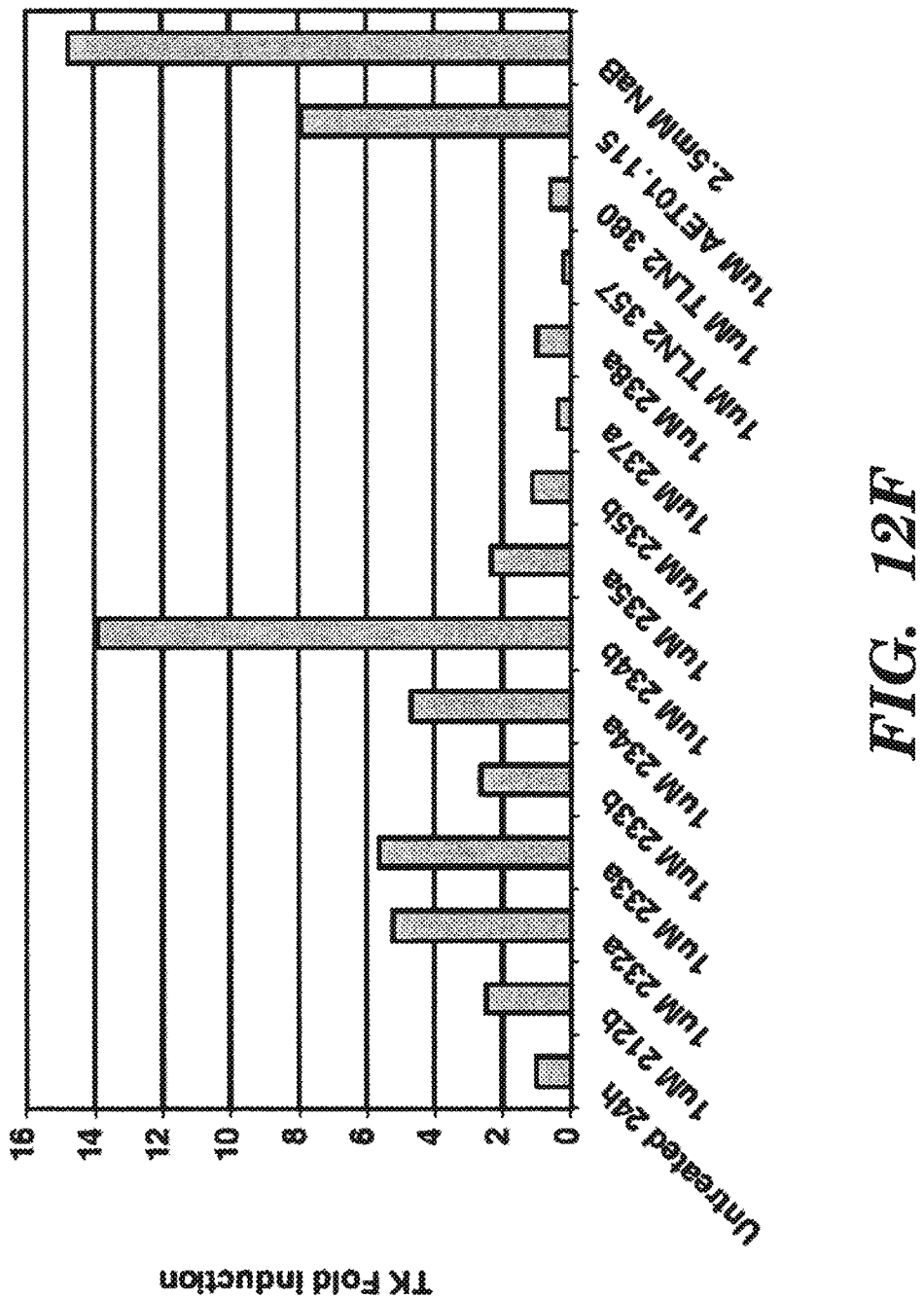

Largazole is a member of macrocyclic depsipeptide that was originally isolated from coral reef cyanobacteria. Largazole is a potent HDAC inhibitor with specificity towards HDAC class 1 and 2 only. Additionally, largazole has very low IC 50 and HDAC isozyme specificity. 16 different analogs of the largazole were tested (ab6-113b, ab6-113a, ab6-123a, ab6-123b, ab6-164b, ab6-156b, 232a, 233a, 238a, 233b, 234b, 235b, 234a, 235a, 237a, 212b, TLN1 357, TNL2 380, ART01) for synergistic cell killing activity in combination with GCV (FIGS. 12A, 12B, 12C, 12D and 12E). 13 largazole derivatives were tested both in combination treatment approach and also for their ability to induce EBV TK (FIG. 12F). Several of the largazoles showed potent cell killing activity in combination with GCV.

Figure 13:
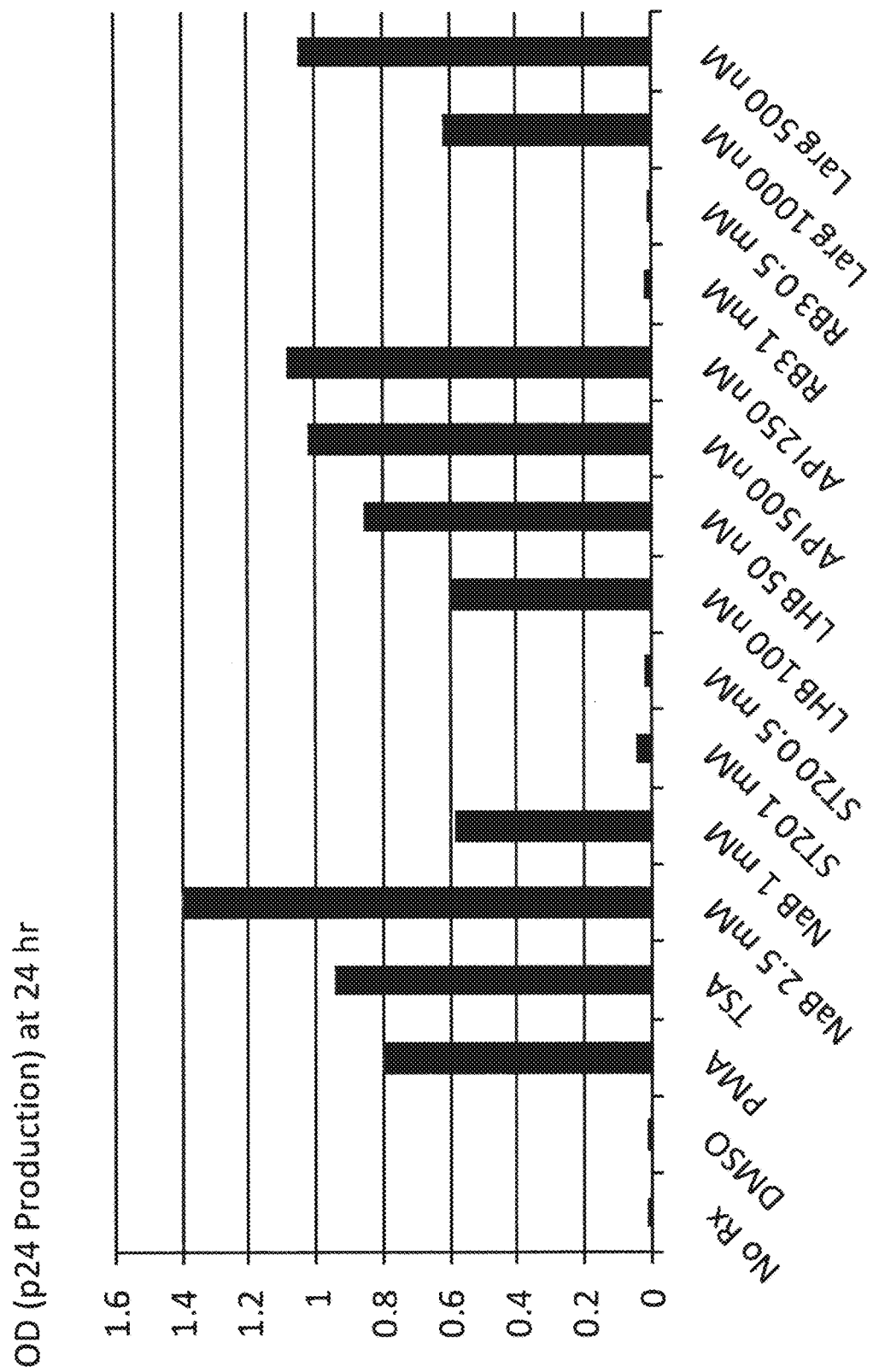
FIG. 13 illustrates results from treatment of an HIV-1-infected monocyte cell line with combination therapy. Viral release (p24 release) was measured through optical density (OD) measurement.
Figure 14:
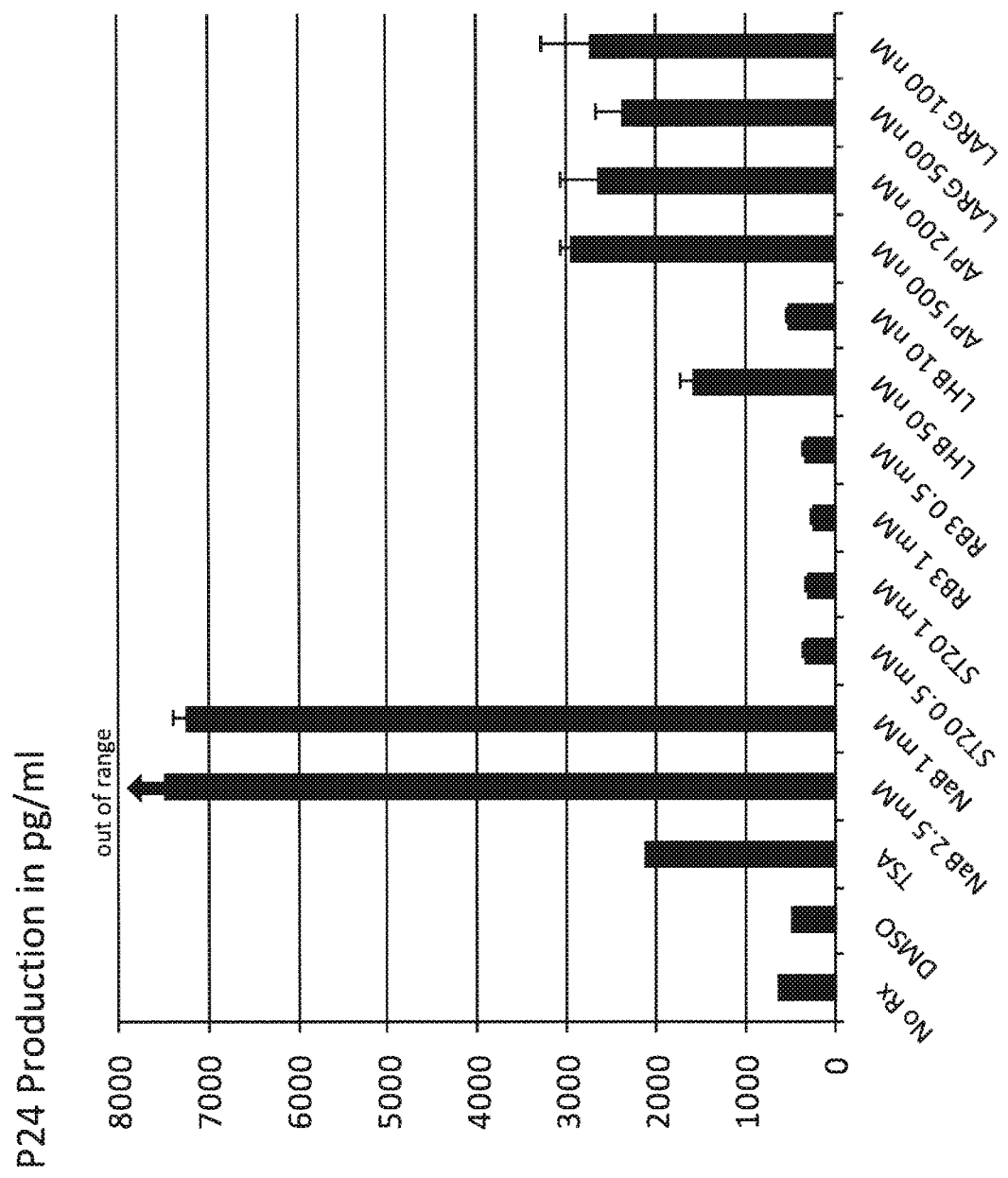
FIG. 14 illustrates results from treatment of an HIV-1-infected monocyte cell line with combination therapy. Viral release (p24 release) was measured through optical density (OD) measurement and then converted into pg of protein.

Example 5: Analysis of Efficacy of Combination Treatment with HIV-Infected Cells Virus production (p24 release) was examined in an HIV-1-infected monocyte line. Cells were treated or not treated with HDAC-inhibitors and other compounds. P24 release expressed as optical density ("OD") (FIG. 13), and then converted to pg of protein (FIG. 14). Arginine butyrate, phorbol myristate acetate (PMA), trichostatin A (TSA), LHB589, apicidin (API) and largazole (LARG) are shown to be active, whereas 2,2-dimethyl butyrate (ST20) and 2-(quinazolin-4-ylamino)butanoic acid (RB3) increased viral production at levels similar to the control of vehicle alone. DMSO was vehicle for some of the compounds tested.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A method for treating a viral associated lymphoproliferative disease associated with Epstein-Barr virus infection in a subject, comprising administering to the subject an inducing agent to induce expression of a viral gene product in a virus-infected cell of the subject and an anti-viral agent whose anti-viral activity is directed to the viral gene product expressed, wherein the anti-viral agent is a nucleoside analog selected from the group consisting of acyclovir (ACV), ganciclovir (GCV), valganciclovir, famciclovir, and penciclovir (PCV), wherein said inducing agent induces expression of the viral gene product in the virus-infected cell in less than six treatment cycles, wherein said inducing agent is an HDAC inhibitor, and wherein the HDAC inhibitor is a largazole.

2. The method of claim 1, wherein said viral associated lymphoproliferative disease associated with Epstein-Barr virus infection is a cancer associated with Epstein-Barr virus infection.

3. The method of claim 1, wherein said viral associated lymphoproliferative disease is lymphoma.

4. The method of claim 1, wherein the inducing agent induces expression of a viral gene product in a virus-infected cell of the subject, wherein the viral gene product is a viral enzyme, an oncogene or proto-oncogene, a transcription factor, a protease, a polymerase, a reverse transcriptase, a cell surface receptor, a structural protein, a major histocompatibility antigen, a growth factor, or a combination thereof.

5. The method of claim 4, wherein the viral gene product is a viral enzyme selected from a thymidine kinase (TK) or protein kinase (PK).

6. The method of claim 1, wherein said inducing agent induces viral TK expression.

7. The method of claim 1, wherein said inducing agent is administered at a dose of about 0.1 to about 2000 mg/kg/day or about 1 to about 100 mg/m²/day.

8. The method of claim 1, wherein said anti-viral agent is ganciclovir or valganciclovir.

9. The method of claim 1, wherein the inducing agent is an HDAC inhibitor capable of inducing TK expression at 500 nM.

10. The method of claim 1, wherein the inducing agent is an HDAC inhibitor capable of inducing TK expression within 6 hours of treatment.

11. The method of claim 1, wherein said inducing agent is administered orally.

12. The method of claim 1, wherein said inducing agent and said anti-viral agent are administered for at least one cycle of therapy, said cycle comprising:
  (i) administering the inducing agent and the anti-viral agent to the subject over a first period of time; and
  (ii) continuing the administration of the anti-viral agent to the subject for a second period; wherein said second period represents the remainder of the cycle.

13. The method of claim 12, wherein during the first period the anti-viral agent and inducing agent are administered in the same composition.

14. The method of claim 12, wherein said first period of time is less than or equal to one-half of the length of the cycle.

15. The method of claim 14, wherein said first period of time is less than or equal to about 5 days, and wherein said cycle is less than or equal to about 21 days.

* * * * *

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
agatgacgac ggcctctacc a                                             21

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cctccttctg tgcacgaagt                                               20

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gctcgtcgtc gacaacggct c                                             21

<210> SEQ ID NO 4
<211> LENGTH: 25
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
caaacatgat ctgggtcatc ttctc                                          25
```